United States Patent
Brueck et al.

(10) Patent No.: US 11,982,626 B2
(45) Date of Patent: May 14, 2024

(54) ENHANCEMENT STRUCTURES FOR SURFACE-ENHANCED RAMAN SCATTERING

(71) Applicant: ARMONICA TECHNOLOGIES, INC., Albuquerque, NM (US)

(72) Inventors: Steven Roy Julien Brueck, Albuquerque, NM (US); Xin Jin, Albuquerque, NM (US); Alexander Neumann, Albuquerque, NM (US); Victor C. Esch, Albuquerque, NM (US)

(73) Assignee: ARMONICA TECHNOLOGIES, INC., Albuquerque, NM (US)

( * ) Notice: Subject to any disclaimer, the term of this patent is extended or adjusted under 35 U.S.C. 154(b) by 0 days.

(21) Appl. No.: 17/588,148

(22) Filed: Jan. 28, 2022

(65) Prior Publication Data
US 2022/0244186 A1 Aug. 4, 2022

Related U.S. Application Data

(60) Provisional application No. 63/280,267, filed on Nov. 17, 2021, provisional application No. 63/191,252, filed on May 20, 2021, provisional application No. 63/168,730, filed on Mar. 31, 2021, provisional application No. 63/143,431, filed on Jan. 29, 2021.

(51) Int. Cl.
*G01N 21/65* (2006.01)
*G01N 21/64* (2006.01)
*G01N 33/543* (2006.01)

(52) U.S. Cl.
CPC ......... *G01N 21/658* (2013.01); *G01N 21/648* (2013.01); *G01N 21/6486* (2013.01); *G01N 33/54346* (2013.01)

(58) Field of Classification Search
None
See application file for complete search history.

(56) References Cited

U.S. PATENT DOCUMENTS

| | | | |
|---|---|---|---|
| 3,977,967 | A | 8/1976 | Trulson et al. |
| 5,234,594 | A | 8/1993 | Tonucci et al. |
| 5,750,415 | A | 5/1998 | Gnade et al. |
| 5,801,092 | A | 9/1998 | Ayers |
| 5,843,767 | A | 12/1998 | Beattie |
| 5,952,665 | A | 9/1999 | Bhargava |
| 6,074,893 | A | 6/2000 | Nakata et al. |
| 6,129,901 | A | 10/2000 | Moskovits et al. |
| 6,136,212 | A | 10/2000 | Mastrangelo et al. |
| 6,231,744 | B1 | 5/2001 | Ying et al. |
| 6,284,987 | B1 | 9/2001 | Al-Modiny |

(Continued)

OTHER PUBLICATIONS

Kaichen, Xu, et al. "Hybrid metal-insulator-metal structures on Si nanowires array for surface enhanced Raman scattering." Opto-Electronic Engineering 44.2 (2017): 185-191 (Year: 2017).*

(Continued)

*Primary Examiner* — Tarifur R Chowdhury
*Assistant Examiner* — Roberto Fabian, Jr.
(74) *Attorney, Agent, or Firm* — Withers Bergman LLP; Thomas C. Meyers

(57) ABSTRACT

The invention generally relates to improved enhancement structures for use in surface-enhanced Raman scattering (SERS) and/or surface-enhanced fluorescence-based analysis.

32 Claims, 37 Drawing Sheets

(56) References Cited

U.S. PATENT DOCUMENTS

| | | |
|---|---|---|
| 6,287,987 B1 | 9/2001 | Miller et al. |
| 6,300,640 B1 | 10/2001 | Bhargava et al. |
| 6,331,479 B1 | 12/2001 | Li et al. |
| 6,359,288 B1 | 3/2002 | Ying et al. |
| 6,452,184 B1 | 9/2002 | Taskar et al. |
| 6,610,593 B2 | 8/2003 | Kohl et al. |
| 6,616,821 B2 | 9/2003 | Broadley et al. |
| 6,685,810 B2 | 2/2004 | Noca et al. |
| 6,763,585 B2 | 7/2004 | Suzuki |
| 6,913,697 B2 | 7/2005 | Lopez et al. |
| 7,052,821 B2 | 5/2006 | Kohl et al. |
| 7,122,153 B2 | 10/2006 | Ho |
| 7,166,531 B1 | 1/2007 | Van et al. |
| 7,290,667 B1 | 11/2007 | Bakajin et al. |
| 7,335,395 B2 | 2/2008 | Ward et al. |
| 7,435,488 B2 | 10/2008 | Tomita et al. |
| 7,470,954 B2 | 12/2008 | Lee et al. |
| 7,476,501 B2 | 1/2009 | Chan et al. |
| 7,510,982 B1 | 3/2009 | Draeger et al. |
| 7,525,037 B2 | 4/2009 | Hansson et al. |
| 7,560,927 B2 | 7/2009 | Maguire et al. |
| 7,612,358 B2 | 11/2009 | Joo et al. |
| 7,629,224 B1 | 12/2009 | Van et al. |
| 7,641,863 B2 | 1/2010 | Doktycz et al. |
| 7,682,591 B2 | 3/2010 | Black et al. |
| 7,704,608 B2 | 4/2010 | Thies et al. |
| 7,745,101 B2 | 6/2010 | Tutt et al. |
| 7,790,234 B2 | 9/2010 | Ayers |
| 7,825,037 B2 | 11/2010 | Brueck et al. |
| 7,833,355 B2 | 11/2010 | Capizzo |
| 7,842,352 B2 | 11/2010 | Gemici et al. |
| 7,875,315 B2 | 1/2011 | Ayers |
| 7,883,742 B2 | 2/2011 | Ayers |
| 7,919,188 B2 | 4/2011 | Ayers |
| 7,955,614 B2 | 6/2011 | Martin et al. |
| 7,985,385 B2 | 7/2011 | Lincoln |
| 7,993,524 B2 | 8/2011 | Ratto et al. |
| 8,105,471 B1 | 1/2012 | Han et al. |
| 8,158,409 B2 | 4/2012 | Wei et al. |
| 8,163,154 B1 | 4/2012 | Hatch et al. |
| 8,293,193 B2 | 10/2012 | Ricoul et al. |
| 8,297,449 B2 | 10/2012 | Afzali-Ardakani et al. |
| 8,329,115 B2 | 12/2012 | Han et al. |
| 8,404,123 B2 | 3/2013 | Brueck et al. |
| 8,440,503 B1 | 5/2013 | Lin et al. |
| 8,514,398 B2 | 8/2013 | Pang et al. |
| 8,722,327 B2 | 5/2014 | Cao et al. |
| 8,810,788 B2 * | 8/2014 | Li ................... G01N 21/554 |
| | | 356/301 |
| 8,940,173 B2 | 1/2015 | Bakajin et al. |
| 9,156,004 B2 | 10/2015 | Brueck et al. |
| 9,778,183 B2 * | 10/2017 | Lin ................... G01N 21/554 |
| 9,927,397 B1 | 3/2018 | Brueck et al. |
| 10,060,904 B1 | 8/2018 | Brueck et al. |
| 10,184,930 B2 | 1/2019 | Brueck et al. |
| 2002/0072243 A1 | 6/2002 | Craighead et al. |
| 2002/0197618 A1 | 12/2002 | Sampson |
| 2003/0187237 A1 | 10/2003 | Chan et al. |
| 2004/0005258 A1 | 1/2004 | Fonash et al. |
| 2004/0132218 A1 | 7/2004 | Ho |
| 2004/0149568 A1 | 8/2004 | Huang et al. |
| 2005/0084980 A1 | 4/2005 | Koo et al. |
| 2005/0170670 A1 | 8/2005 | King et al. |
| 2005/0191774 A1 | 9/2005 | Li et al. |
| 2005/0196779 A1 | 9/2005 | Ho et al. |
| 2005/0244977 A1 * | 11/2005 | Drachev ............ G01N 33/553 |
| | | 436/518 |
| 2006/0015061 A1 | 1/2006 | Kuo et al. |
| 2006/0175653 A1 | 8/2006 | Joo et al. |
| 2006/0240974 A1 * | 10/2006 | Hongo .................. B01J 23/46 |
| | | 502/60 |
| 2006/0274230 A1 | 12/2006 | Shao et al. |
| 2006/0275911 A1 | 12/2006 | Wang et al. |
| 2006/0278580 A1 | 12/2006 | Striemer et al. |
| 2007/0122313 A1 | 5/2007 | Li et al. |
| 2007/0134939 A1 | 6/2007 | Brueck et al. |
| 2007/0264481 A1 | 11/2007 | DeSimone et al. |
| 2008/0032308 A1 | 2/2008 | Su et al. |
| 2008/0041733 A1 | 2/2008 | Hibbs et al. |
| 2008/0076670 A1 | 3/2008 | Sivan et al. |
| 2008/0134939 A1 | 6/2008 | Arpac et al. |
| 2008/0239307 A1 | 10/2008 | Talley et al. |
| 2008/0242556 A1 | 10/2008 | Cao et al. |
| 2008/0251382 A1 | 10/2008 | Han et al. |
| 2009/0214392 A1 | 8/2009 | Kameoka et al. |
| 2009/0224435 A1 | 9/2009 | Gogotsi et al. |
| 2009/0243428 A1 | 10/2009 | Qiao |
| 2009/0305278 A1 | 12/2009 | Hardin et al. |
| 2010/0085566 A1 * | 4/2010 | Cunningham ....... G01N 21/658 |
| | | 427/75 |
| 2010/0104650 A1 | 4/2010 | Lee et al. |
| 2010/0301462 A1 | 12/2010 | Sinha et al. |
| 2011/0011794 A1 | 1/2011 | Brueck et al. |
| 2011/0036994 A1 | 2/2011 | Frayling |
| 2011/0065207 A1 | 3/2011 | Ferrari et al. |
| 2011/0136676 A1 | 6/2011 | Greene |
| 2011/0168560 A1 | 7/2011 | Afzali-Ardakani et al. |
| 2011/0212512 A1 | 9/2011 | Wang et al. |
| 2011/0236984 A1 | 9/2011 | Sun et al. |
| 2012/0105853 A1 | 5/2012 | Pang et al. |
| 2012/0160687 A1 | 6/2012 | Akeson et al. |
| 2013/0021606 A1 | 1/2013 | Rigneault et al. |
| 2013/0164191 A1 | 6/2013 | Coursey |
| 2013/0176563 A1 | 7/2013 | Ozawa et al. |
| 2013/0193065 A1 | 8/2013 | Brueck et al. |
| 2013/0260472 A1 | 10/2013 | Holt |
| 2013/0270521 A1 | 10/2013 | Zhu et al. |
| 2014/0204372 A1 | 7/2014 | Pang et al. |
| 2014/0335269 A1 | 11/2014 | Bond et al. |
| 2015/0136601 A1 | 5/2015 | Austin et al. |
| 2016/0146736 A1 * | 5/2016 | Chen ................... G01N 21/658 |
| | | 356/301 |
| 2016/0377590 A1 | 12/2016 | Brueck et al. |
| 2017/0253910 A1 | 9/2017 | Brown et al. |
| 2017/0299548 A1 | 10/2017 | Yoshida et al. |
| 2019/0227050 A1 | 7/2019 | Brueck et al. |
| 2019/0310398 A1 * | 10/2019 | Salomon .............. G02B 5/3025 |

OTHER PUBLICATIONS

Kinkhabwala, Anika, et al. "Large single-molecule fluorescence enhancements produced by a bowtie nanoantenna." Nature photonics 3.11 (2009): 654-657 (Year: 2009).*

Kheyraddini Mousavi, Behnam. "Selected Applications of Silicon Nanopillar Arrays." (2018) (Year: 2018).*

Nam, Wonil, et al. "Refractive-index-insensitive nanolaminated SERS substrates for label-free Raman profiling and classification of living cancer cells." Nano letters 19.10 (2019): 7273-7281 (Year: 2019).*

Fischbein, et al., "Electron beam nanosculpting of suspended graphene sheets", Appl. Phys. Lett. 2008, 93: 113107-1-3.

Garaj, et al., "Graphene as a subnanometre trans-electrode membrane", Nature 2010, 467:190-193.

Venkatesan, et al., "Highly sensitive, mechanically stable nanopores for parallel DNA analysis", Adv. Mater. 2009, 21: 2771-2776.

Wanunu, et al., "Chemically modified solid-state nanopores", Nano Lett. 2007, 7:1580-1585.

Reisner, et al., "Nanoconfinement-enhanced conformational response of single DNA molecules to changes in ionic environment", Phys. Rev. Lett. 2007, 99: 058302-1-4.

Levy, et al., "Entropic unfolding of DNA molecules in nanofluidic channels", Nano Lett. 2008, 8:3839-3843.

Xia, et al., "DNA transport in hierarchically structured colloidal nanoparticle porous-wall nanochannels", Nano Lett. 2008, 8:1610-1618.

Xia, et al., "Nanostructures and functional materials fabricated by interferometric lithography", Adv. Materials 2011, 23: 147-179.

Chen, et al., "DNA translocation through an array of kinked nanopores", Nat. Matis. 2010, 9: 667-675.

Osborne, et al., "Single-molecule LATE-PCR analysis of human mitochondrial genomic sequence variations", PLoS ONE 2009, 4(5):e5636.

(56) References Cited

OTHER PUBLICATIONS

Jia, et al., "Construction of a microfluidic chip, using dried-down reagents, for LATE-PCR amplification and detection of single-stranded DNA", Lab on a chip 2013, 4635-4641.
Pettinger, "Single-molecule surface- and tip-enhanced Raman spectroscopy", Mol. Phys. 2010, 108: 2039-2059.
Le Ru, et al., "Single-molecule surface-enhanced Raman spectroscopy", Annu. Rev. Phys. Chem. 2012, 63: 65-87.
Li, et al., "Single cell Raman spectroscopy for cell sorting and imaging", Cur. Opin. in Biotechnol. 2012, 23: 56-63.
Steuwe, et al., "Surface enhanced coherent anti-Stokes Raman scattering on nanostructured gold surfaces", Nano Lett. 2011, 11: 5339-5343.
Steuwe, et al., "Molecular imaging with surface-enhanced CARS on nanostructures", Proc. SPIE 2012, 8234:82340E-1-7.
Rasmussen, et al., "Surface- and tip-enhanced Raman scattering of DNA components", Jour. Raman Spectrosc. 2006, 37, 311-317.
McNally, et al., "Optical Recognition of Converted DNA Nucleotides for single-molecule DNA sequencing using nanopore arrays", Nano Lett. 2010, 10: 2237-2244.
Fort, et al., "Surface enhanced fluorescence", Jour. Phys. D: Appl. Phys. 2008, 41: 013001-1-31.
Heinrich, et al., "Wide-field coherent anti-Stokes Raman scattering microscopy", Appl. Phys. Lett. 2004, 84: 616-818.
Toytman, et al., "Wide-field coherent anti-Stokes Raman scattering microscopy with non-phase-matching illumination", Opt. Lett. 2007, 32:1941-1943.
Toytman, et al., "On illumination schemes for wide-field CARS microscopy", Opt. Exp. 2009, 17: 7339-7347.
Mendoza et al., Electrophoretic plasmonic nanopore biochip genome sequencer, 2019, Optics and Laser Technology, 109, 199-211, publicly available on Aug. 10, 2018. (Year: 2019).
Belkin et al., Plasmonic Nanopores for Trapping, Controlling Displacement, and Sequencing of DNA, ACS Nano, Nov. 24, 2015, 9(11):10598-10611.
International Search Report and Written Opinion issued in International Application No. PCT/US2020/013325, dated May 14, 2020, 17 pages.
Rand et al., Mapping DNA Methylation with High Throughput Nanopore Sequencing, Nat Methods, Feb. 20, 2017, 14(4):411-413.
Chang Chen, et al. "Detection of DNA Bases and Oligonucleotides in Plasmonic Nanoslits Using Fluidic Sers." IEEE Journal of Selected Topics in Quantum Electronics, vol. 19, No. 3, 2013, pp. 4600707-4600707, https://doi.org/10.1109/jstqe.2012.2226564. (Year: 2013).
Chen, Zhu, et al. "DNA Translocation through an Array of Kinked Nanopores." Nature Materials, vol. 9, No. 8, 2010, pp. 667-675, doi:10.1038/nmat2805. (Year: 2010).
Dukhyun Choi et al., "Self-Organized Hexagonal-Nanopore SERS Array", Small, vol. 6, No. 16, Jul. 2010, pp. H41-H1744.
International Search Report and Written Report dated May 27, 2015 from International Application No. PCT/US2014/067764, pp. 1-14.
Nam et al., "Sub-10-nm Nanochannels by Self-Sealing and Self-Limiting Atomic Layer Deposition," American Chemical Society, Nano Letters 2010, 10, 3324-3329.
Colilla, Montserrat et al., "Mesoporous silica nanoparticles for the design of smart delivery nanodevices", Biomaterials Science, Sep. 21, 2012, pp. 114-134.
Mahurin, Shannon et al., "Atomic layer deposition of TiO2 on mesoporous silica", Journal of Non-crystalline Solids 352 (2006), pp. 3280-3284.
Bentley, et al., "Accurate whole human genome sequencing using reversible terminator chemistry", Nature 2008, 456(7218):53-59.
McKernan, et al., "Sequence and structural variation in a human genome uncovered by short-read, massively parallel ligation sequencing using two-base encoding", Genome research 2009, 19(9):1527-1541.
Shearer, et al., "Comprehensive genetic testing for hereditary hearing loss using massively parallel sequencing", Proceedings of the National Academy of Sciences of the United States of America 2010, 107(49):21104-21109.
Margulies, et al., "Genome sequencing in microfabricated high-density picolitre reactors", Nature 2005, 437 7057):376-380.
Eid, et al., "Real-time DNA sequencing from single polymerase molecules", Science 2009, 323(5910):133-138.
Flusberg, et al., "Direct detection of DNA methylation during single-molecule, real-time sequencing" Nature methods 2010, 7(6):461-465.
Korlach, et al., "Real-time DNA sequencing from single polymerase molecules", Methods in enzymology 2010, 472:431-455.
Schadt, et al., "Computational solutions to large-scale data management and analysis", Nature reviews Genetics 2010, 11(9):647-657.
Schadt, et al., "A window into third-generation sequencing", Human molecular genetics 2010, 19(R2):R227-240.
Rothberg, et al., "An integrated semiconductor device enabling non-optical genome sequencing", Nature 2011, 475(7356):348-352.
Kroll, et al., "Starvation-associated genome restructuring can lead to reproductive isolation in yeast", PLoS ONE 2013, 8(7):e66414.
Aragon, et al., "Genomic analysis of *Saccharomyces cerevisiae* isolates that grow optimally with glucose as the sole carbon source" Electrophoresis 2012, 33(23):3514-3520.
Luan, et al, "Control and reversal of the electrophoretic force on DNA in a charged nanopore", J Phys Condens Matter 2010, 22(45):454123.
Clarke, et al., "Continuous base identification for single-molecule nanopore DNA sequencing", Nat Nanotechnol 2009, 4(4):265-270.
McNally, et al., "Optical recognition of converted DNA nucleotides for single-molecule DNA sequencing using nanopore arrays", Nano Lett 2010, 10(6):2237-2244.
Das, et al., "Single molecule linear analysis of DNA in nano-channel labeled with sequence specific fluorescent probes", Nucleic acids research 2010, 38(18):e177.
Leem, et al., "Closing the gaps on human chromosome 19 revealed genes with a high density of repetitive tandemly arrayed elements", Genome research 2004, 14(2):239-246.
Consortium IHGS, "Finishing the euchromatic sequence of the human genome", Nature 2004, 431(7011):931-945.
Cole, et al., "Finishing the finished human chromosome 22 sequence", Genome biology 2008, 9(5):R78.
Church, et al., "Modernizing reference genome assemblies", PLoS biology 2011, 9(7):e1001091.
Frazer, et al., "A second generation human haplotype map of over 3.1 million SNPs", Nature 2007, 449(7164):851-861.
Eichler, et al., "A haplotype map of the human genome", Nature 2005, 437(7063):1299-1320.
Consortium GP, "A map of human genome variation from population-scale sequencing", Nature 2010, 467(7319):1061-1073.
Venter, et al., "The sequence of the human genome", Science 2001, 291 (5507):1304-1351.
Lander, et al., "Initial sequencing and analysis of the human genome", Nature 2001, 409(6822):860-921.
Suk, et al., "A comprehensively molecular haplotype-resolved genome of a European individual", Genome research 2011, 21(10):1672-1685.
Kitzman, et al., "Haplotype-resolved genome sequencing of a Gujarati Indian individual", Nature Biotechnology 2011, 29(1):59-63.
Peters, et al., "Accurate whole-genome sequencing and haplotyping from 10 to 20 human cells", Nature 2012, 487(7406):190-195.
Kaper, et al., "Whole-genome haplotyping by dilution, amplification, and sequencing", Proceedings of the National Academy of Sciences of the United States of America 2013, 110(14):5552-5557.
Burgess, "Genomic instability: Shattered details", Nature reviews Genetics 2012, 13(3):150.
Rausch, et al., "Genome sequencing of pediatric medulloblastoma links catastrophic DNA rearrangements with TP53 mutations", Cell 2012, 148(1-2):59-71.
Crasta, et al., "DNA breaks and chromosome pulverization from errors in mitosis", Nature 2012, 482(7383):53-58.

(56) References Cited

OTHER PUBLICATIONS

Branton, et al., "The potential and challenges of nanopore sequencing", Nat. Biotech. 2008, 26:1146-1153.
Venkatesan, et al., "Nanopore sensors for nucleic acid analysis", Nat. Nanotech. 2011, 6:615-624.
Manrao, et al., "Reading DNA at single-nucleotide resolution with a mutant MspA nanopore and phi29 DNA polymerase", Nature biotechnology 2012, 30(4):349-353.
Meller, et al., "Single Molecule measurements of DNA transport through a nanopore", Electrophoresis 2002, 23:2583-2591.
Derrington, et al., "Nanopore DNA sequencing with MspA", Proc. Natl. Acad. Sci. USA 2010, 107:16060-16065.
Brenner, et al., "Sequence-specific detection of individual DNA polymerase complexes in real time using a nanopore", Nat. Nanotech. 2007, 2:718-724.
Rincon-Restrepo, et al., "Controlled translocation of individual DNA molecules through protein nanopores with engineering molecular brakes", Nano Lett. 2011, 11 :746-750.

\* cited by examiner inverted nanopyramids

ENHANCEMENT STRUCTURES FOR SURFACE-ENHANCED RAMAN SCATTERING

CROSS-REFERENCE TO RELATED APPLICATIONS

This application claims priority to, and the benefit of, U.S. Provisional Application No. 63/143,431, filed Jan. 29, 2021, U.S. Provisional Application No. 63/168,730, filed Mar. 31, 2021, U.S. Provisional Application No. 63/191,252, filed May 20, 2021, and U.S. Provisional Application No. 63/280,267, filed Nov. 17, 2021, the content of each of which is incorporated by reference herein in its entirety.

FIELD OF THE INVENTION

The invention relates to enhancement structures for use in surface-enhanced Raman scattering (SERS) and/or surface-enhanced florescence-based analysis.

BACKGROUND

Raman scattering, also referred to as the Raman effect, is the inelastic scattering of photons by matter, meaning that there is an exchange of energy between the material and the energy of the scattered photon is either larger or smaller than that of the incident photon. This effect involves vibrational energy being gained by a molecule as incident photons from a visible laser are shifted to lower energy. This is called normal Stokes Raman scattering. The opposite case in which the photon gains energy from the molecule is called anti-Stokes Raman scattering. The spectrum of the Raman-scattered light depends on the molecular constituents present and their state, allowing the spectrum to be used for material identification and analysis. Accordingly, the effect is exploited by chemists and physicists to gain information about materials for a variety of purposes by performing various forms of Raman spectroscopy, which employs the Raman effect for substances analysis In electrical engineering terms, Raman scattering is the mixing of a carrier frequency, the pump laser at frequency $\omega_P$ and wavelength $\lambda_p = 2\pi c/\omega_p$ (c is the vacuum speed of light) with intrinsic vibrations of the molecule or solid at frequency v to produce sidebands at $\omega_p - v$ (Stokes frequency) and $\omega_p + v$ (anti-Stokes frequency). The chemical specificity of a material undergoing analysis comes from the direct determination of the intrinsic vibrational frequencies. A common difficulty with Raman spectroscopy is that Raman scattering is a weak effect, typical scattering cross sections are between $10^{29}$ to $10^{31}$ cm$^2$ per molecule, which means that much Raman scattering has been restricted to laboratory settings with powerful lasers and sensitive detectors.

Surface-enhanced Raman scattering, or SERS, is emerging as a sensitive diagnostic technology with chemical specificity applicable to many chemical and solid-state materials. SERS strongly enhances the Raman signals as a result of the enhanced, localized near-fields near metal nanostructures and offers the promise of making Raman scattering a much more widely applicable tool. Accordingly, SERS is becoming a more commonly used sensing technique in which inelastic light scattering by molecules is greatly enhanced (by factors up to $10^8$ or even larger) when the molecules are adsorbed onto corrugated metal surfaces such as silver or gold or to nanoparticles of these same materials. SERS was first observed on rough metal surfaces, and has been subsequently explored in both colloidal systems and patterned surfaces. Single molecule sensitivities have been demonstrated in so-called "hot-spots" that correspond to close approach (~1 nm) between two particles. In colloidal systems, this close approach is not well controlled and the density of such hot spots is uncertain and leads to difficulties in interpretation of the signals. In deliberately patterned structures, this scale remains beyond the reach of most lithography approaches and requires difficult and non-scalable fabrication such as combinations of e-beam lithography and atomic layer deposition. Notwithstanding this extensive effort, inexpensive and manufacturable, reproducible, well-characterized SERS substrates are not readily available.

SUMMARY

The present invention provides various electromagnetic-field enhancement structures for use in surface-enhanced Raman scattering (SERS) and/or surface-enhanced fluorescence-based analysis. In particular, the present invention provides various embodiments of an enhancement structure that has been optimized to provide significant signal enhancement, including enhanced electromagnetic fields and near-field nanoscale resolution. Accordingly, the enhancement structures of the present invention are particularly useful for long-read nucleic acid sequencing, including providing optical resolution in nanopore sequencing methods, thereby allowing for identification of single molecules. One feature of the SERS phenomena, as well as surface-enhanced coherent anti-stokes Raman spectroscopy (SE-CARS), is that enhancement extends to both the excitation and the emitted signal wavelengths. Thus, the enhancement structures of the present invention have been designed in order to optimize the enhancement at the wavelengths of interest without requiring lithographic patterning at a molecular size scale of about 1 nm.

The enhancement structures of this invention include a periodic array of nanoscale metallic structures fabricated on a surface of a dielectric substrate. The enhancement factor of a given enhancement structure is increased based on: adjustments to the structural design of the nanoscale metallic structures; inclusion of dielectric film layers; adjustments to structural design of dielectric film layers; inclusion of different materials for the dielectric substrate, the dielectric film layers, and/or the nanoscale metallic structures; and combinations thereof.

In one embodiment, the enhancement structure includes a periodic array of nanoscale metallic structures, generally in the form of single discs, arranged on a top surface of a substrate. The use of discs allows for relatively simple fabrication with low costs. The discs may include a metal, including, but not limited to, as least one of gold (Au), silver (Ag), aluminum (Al), and one or more alloys thereof. The dimensions of the discs (i.e., x-, y-, and z-dimensions) can be tuned so as to place the resulting resonance within the vicinity of the wavelength of interest. In other words, at least a height and width of each disc can be varied so as to place an electric dipole resonance at a desired pump wavelength.

In some embodiments, enhancement may be increased based, at least in part, on the shape of the discs. In particular, in some embodiments, the discs have an elliptical shape which can be used to shift an electrical dipole resonance to the desired pump wavelength, as compared to the resonance when the discs have a substantially circular shape. This provides further concentration of the field at the narrow ends of the ellipse and increases the extent and the localization of the field enhancement.

Alternatively, in some embodiments, each nanoscale metallic structure includes a pair of concentric discs, including an outer annular disc and an inner annular disc coaxially aligned with one another. Such as a design allows for setting the electric dipole resonance by providing a narrow gap between the pair of discs to enhance the field intensity. The width of this gap can be set by deposition processes without the need for nanometer scale lithography.

Alternatively, in some embodiments, each nanoscale metallic structure comprises a metal-insulator-metal (MIM) structure. In some embodiments, the metal of the MIM structure comprises at least one of one of gold (Au), silver (Ag), aluminum (Al), and one or more alloys thereof and the insulating layer comprises at least one of silicon dioxide ($SiO_2$), silicon nitride ($Si_3N_4$), aluminum oxide ($Al_2O_3$), titanium dioxide ($TiO_2$) and hafnium dioxide $HfO_2$. In some embodiments, the electric dipole resonance of the array of nanoscale MIM structures is tuned to match a Raman pump wavelength. In some embodiments, the magnetic dipole resonance of the array of nanoscale MIM structures is tuned to match a Raman Stokes wavelength.

The present invention recognizes that enhanced single molecule detection depends on the detailed structure near the electromagnetic hot spot which is localized and occurs at the interface of the bottom surface of the nanoscale metallic structure. For example, certain materials, including gold (Au), do not adhere well to certain substrate materials, such as fused silica ($SiO_2$) or the like. In conventional structures, most often a thin layer of titanium (Ti), nickel (Ni), or chromium (Cr) is deposited immediately before adding the gold layer. The use of these materials can result in significant loss at the pump and Stokes wavelengths. Since the electromagnetic hot spot is localized just at the layer interface, such a loss can have a significant effect on the enhancement. Accordingly, in some embodiments, a dielectric adhesion layer is deposited between the top surface of the substrate and the array of nanoscale metallic structures to thereby adhere the array of nanoscale metallic structures to the top surface of the substrate. In particular, the dielectric layer may include a metal oxide material, including at least one of silicon dioxide ($SiO_2$), magnesium oxide (MgO), and aluminum oxide ($Al_2O_3$), which generally reduces the amount of loss at Raman pump and Raman Stokes wavelengths, as compared to other materials commonly used in coupling metallic structures to a substrate. Simulation testing shows that the dielectric sticking layer material, such as $SiO_2$, leads to a significant improvement as compared with a metal such as Ti, Ni, or Cr, by reducing the amount of loss.

In some embodiments, the dielectric adhesion layer that adheres the nanoscale metallic structures to the substrate results in improved performance if portions of the adhesion layer extend beyond the bottom surface of the metallic structures. In particular, in some embodiments, each of the array of nanoscale metallic structures is adhered to the top surface of the substrate via a separate dielectric adhesion layer. In such an embodiment, at least some of the adhesion layers have a surface area that is greater than a surface area of a bottom surface of a respective nanoscale metallic structure such that a portion of a dielectric layer extends beyond a perimeter of a bottom surface of a respective nanoscale metallic structure and is exposed on the top surface of the substrate. Accordingly, the dielectric adhesion layer may include an overhanging configuration.

Yet still, in some embodiments in which the enhancement structure comprises MIM structures, one or more additional dielectric layers may be deposited around at least a periphery of one or more respective MIM structures. In particular, at least one of the MIM structures may include an additional dielectric layer (in addition to the dielectric adhesion layer) deposited around a periphery thereof, wherein the additional dielectric layer has a varying thickness. The additional dielectric layer may include a variable thickness that is greater than a thickness of the underlying dielectric adhesion layer in some portions of the circumference of the disk (in the event that the adhesion layer has a portion that is extending beyond the bottom surface of the MIM) and a second thickness that is less than a thickness of the underlying dielectric adhesion layer in other portions of the disc circumference. For example, in one embodiment, the additional dielectric layer may include a wedge-shaped profile that tapers from the first thickness to the second thickness, wherein the additional dielectric layer is deposited at an angle relative to the top surface of the substrate. Accordingly, the additional dielectric layer has a tilted orientation. Simulation testing shows that the tilted dielectric layer improved single molecule sensitivity and localized detection.

The present invention further provides methods of fabricating the various embodiments of the enhancement structures described herein.

BRIEF DESCRIPTION OF THE DRAWINGS

FIGS. 19A and 19B illustrate enhancement structures including a disc or pillar, but mainly differ in that the disc of FIG. 19A is adhered to the surface of a glass substrate via a titanium layer while the disc of FIG. 19B is adhered to the surface of a glass substrate via a silicon dioxide layer. FIGS. 19C-19E illustrates enhancement structures that include a MIM structure. The MIM structure of FIG. 19C is adhered to the surface of a glass substrate via a titanium layer, while the MIM structures of 19D and 19E are adhered to the surface of a glass substrate via a silicon dioxide layer. Furthermore, the dimensions of the layers of the MIM structures of FIGS. 19D and 19E differ.

FIG. 34A is a side view, partly in section, showing a chromium (Cr) mask with holes to define pattern. FIG. 34B shows inverted pyramids that result from KOH etching. FIG. 34C shows further etching to form nanopores at the bottom of the inverted pyramids. FIG. 34D shows coating with a thin sacrificial resist layer. FIG. 34E shows silica nanoparticles are spun into the inverted pyramids. FIG. 34F shows the wafer is sintered (~800° in air/oxygen ambient) to remove the resist and sinter the nanoparticles for stability. FIG. 34G shows a thin film is added to trap the nanoparticles if necessary and the storage chambers are defined. FIG. 34H shows handle wafer is added. FIG. 34I is a top view showing the spatial relationship between the sticking layer (i.e., dielectric adhesion layer), the open area, and the enhancement structure. FIG. 34J shows operation.

FIG. 41A illustrates encoding of data in multiple emission colors to thereby facilitate more bits per single data block feature. FIG. 41B illustrates the use of multiple colors and/or mixtures of colors on each single data block.

DETAILED DESCRIPTION

Figure 1:
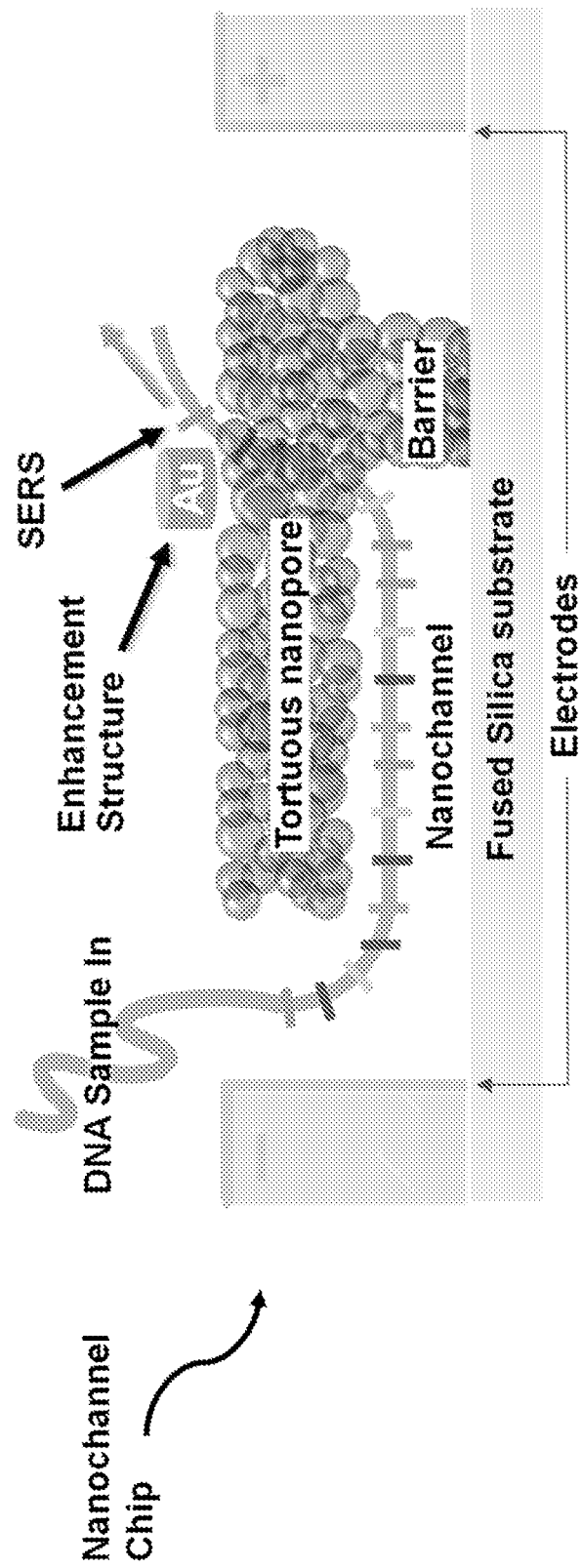
FIG. 1 shows an exemplary nanochannel chip, partly in section, with which the various embodiments of the enhancement structures of the present invention can be used.

By way of overview, the present invention is directed to various embodiments of enhancement structures and methods of fabricating such enhancement structures. More specifically, the enhancement structures of the present invention are electromagnetic-field enhancement structures for use in surface-enhanced Raman scattering (SERS) and/or surface-enhanced fluorescence-based analysis.

Significant research effort has been performed to develop systems in the SERS technology, to include optimization of structures that provide very significant signal enhancement. One feature of the SERS phenomena, as well as SECARS, is that the enhancement extends to both the excitation and the emitted signal wavelengths, and thus enhancement structure optimization is performed in order to optimize the enhancement at the wavelengths of interest. SERS enhancements of up to $10^{12}$ have been reported, and single molecule sensitivity can be achieved using SERS and enhancement structures with enhancements of $10^9$ as has been reported in the literature. These single-molecule observations have been largely restricted to systems with characteristic dimensions on the molecular scales (~1 nm or less) which are difficult to manufacture in high volumes.

In order to improve S/N, which also improves potential for measuring more single molecules/sec, maximal enhancement is desired. This is commonly limited by a variety of factors, including damage of the target molecule and/or enhancement structure as a result of the enhanced fields which sets limits on the allowable intensity of the pump laser beam.

The present invention provides various embodiments of an enhancement structure that has been optimized to provide significant signal enhancement, including enhanced electromagnetic fields and near-field nanoscale resolution. One feature of the SERS phenomena, as well as surface-enhanced coherent anti-stokes Raman spectroscopy (SECARS), is that enhancement at both the excitation and the emitted signal wavelengths plays a role in the observation. Thus, the enhancement structures of the present invention have been optimized in order to optimize the enhancement at the wavelengths of interest. Accordingly, the enhancement structures of the present invention are suitable for DNA sequencing and other applications. The enhancement structures are particularly useful for long-read nucleic acid sequencing, including providing optical resolution in nanopore sequencing methods, thereby allowing for identification of single molecules.

Nanopore sequencing is a third generation approach used in the sequencing of biopolymers, specifically polynucleotides in the form of DNA or RNA. Most embodiments of nanopore sequencing work by monitoring changes to an electrical current as nucleic acids are passed through a protein nanopore. The resulting signal is decoded to provide the specific DNA or RNA sequence. This current change is not intrinsic to the nucleotide and is in fact influenced by several (4 to 6) nearest neighbors, making the interpretation of the current signals difficult and resulting in inaccuracies in the sequencing. An optical readout, such as SERS is preferable since it provides a molecularly specific signature. This requires both sufficient sensitivity to measure single nucleotides and sufficient spatial resolution to monitor the sequence as the long-chain molecule passes through the electromagnetic "hot-spot."

FIG. 1 shows an exemplary nanochannel chip, partly in section, with which the various embodiments of the enhancement structures of the present invention can be used. The nanochannel chip can be used in nanopore sequencing methods. Such nanopore sequencing analysis may involve passing DNA (or related long-chain molecules such as RNA and proteins), through a nanoscopic opening (i.e., a nanopore) while monitoring a signal to detect signatures of the various DNA components: adenine (A), cytosine (C), guanine (G), and thymine (T). A nanopore may be designed to have a size that allows the polymeric molecule to pass only in a sequential, single file order. As the polymeric molecule passes through the nanopore, various techniques may be used to obtain signature signals that allow for the identification of the various bases of a DNA molecule (i.e., sequence), most often nonspecific electrical measurements (e.g. current blockage or capacitance) have been reported. The various components of a nanochannel chip are described in greater detail in U.S. Publication No. 2020/0224263 to Suryanaraya et al., incorporated by reference herein in its entirety.

Figures 2A, 2B, 2C:
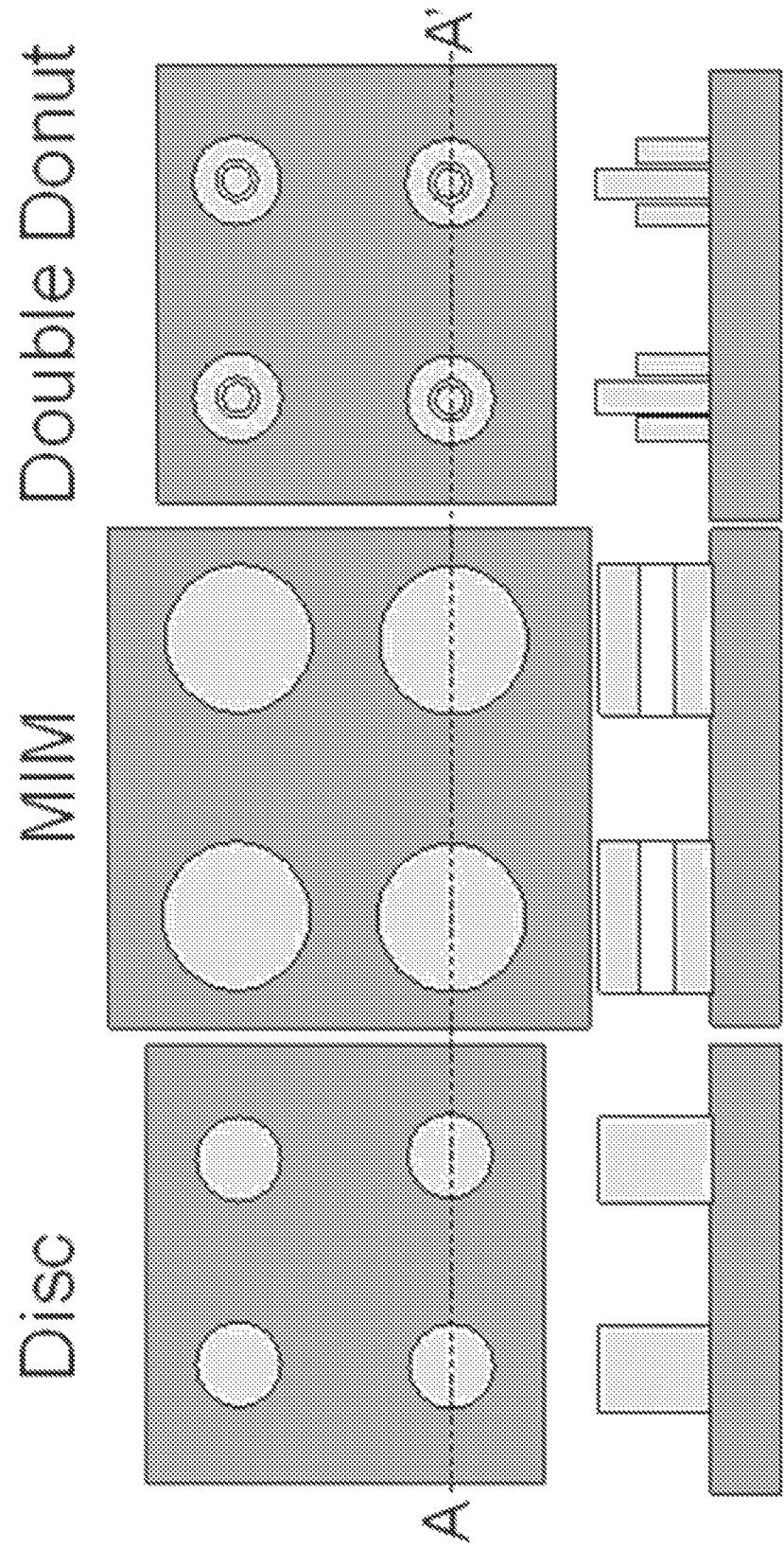
FIGS. 2A, 2B, and 2C illustrate various embodiments of the nanoscale metallic structures consistent with the present disclosure, including
Figure 3B:
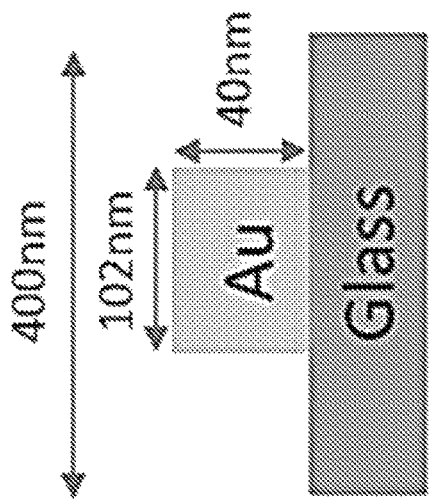
FIGS. 3A, 3B, 3C, and 3D are side views of four designs of nanoscale metallic structures, respectively, wherein each design has a different dimensioned structure (individual discs)
Figure 3D:
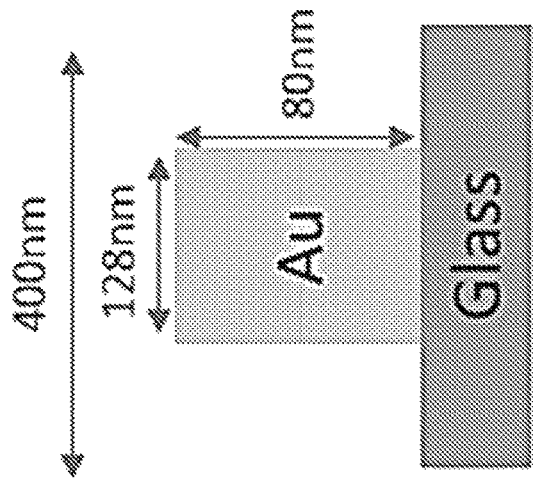
Figure 3A:
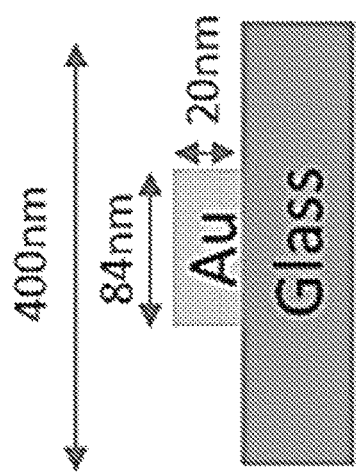
Figure 3C:
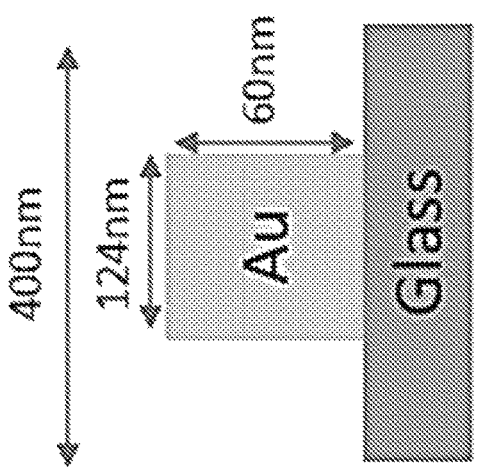

FIGS. 2A, 2B, and 2C illustrate various embodiments of the nanoscale metallic structures consistent with the present disclosure. Each of the embodiments of enhancement structures illustrated in FIGS. 2A, 2B, and 2C include a substrate and a periodic array of nanoscale metallic structures arranged on the top surface of the substrate. The array of nanoscale metallic structures comprises at least one of gold (Au), silver (Ag), aluminum (Al), and one or more alloys thereof. As shown in FIG. 2A, the metallic structures may include discs or pillars, while FIG. 2B illustrates nanoscale metal-insulator-metal (MIM) structures, and FIG. 2C illustrates pairs of concentric discs, including an outer annular disc and an inner annular disc coaxially aligned with one another. Such as a design allows for setting the electric dipole resonance by providing a narrow gap between the pair of discs to enhance the field intensity. As detailed below, this narrow gap can be defined by deposition and etching processes and does not require lithography at the dimensions of the gap.

FIGS. 3A, 3B, 3C, and 3D are side views of four designs of nanoscale metallic structures, respectively, wherein each design has a different dimensioned structure (individual discs). This is perhaps the simplest structure to fabricate. A systematic study of this design was performed as a result of localized surface plasmonic resonances (LSPR).

It should be noted that all of the simulations and experimental results described herein utilized gold structures because of its superior environmental stability. It should be noted that gold has interband transistions starting at yellow wavelengths that impact the dielectric properties, so the results are all presented for a 633 nm excitation wavelength (HeNe laser) and assume a Raman shift of 1000 cm$^{-1}$, putting the Stokes wavelength at 666 nm. Experimentally, a 633-nm pump laser was used for simulation and experimental results. As such, tuning structural dimensions of the discs was performed so as to put the resonance in the vicinity of this wavelength. Furthermore, normal incidence excitation was used and the resulting fields were calculated using commercial finite difference time domain (FDTD) software (Lumerical™).

For some applications, other (shorter) wavelengths may be desired, for example for experiments involving resonant Raman scattering which often require ultraviolet excitation. This will require the use of different metals such as Ag or Al. However, the overall profile of the field enhancement and the strategies for optimizing the enhancement will not be altered.

As illustrated in FIGS. 3A, 3B, 3C, and 3D, four designs were provided with the LSPR resonance near 633 nm. The thickness of each is the independent variable and the diameter of each is adjusted to maintain the resonance wavelength. In each case, the periodicity of the square array is 400 nm.

Figure 4:
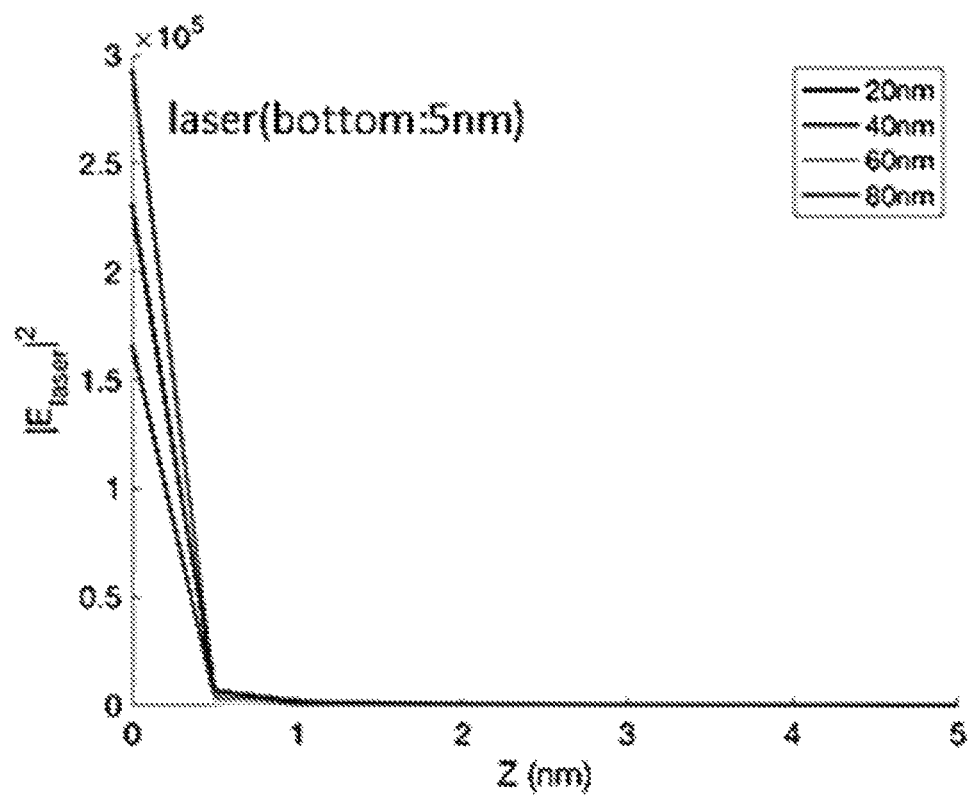
FIGS. 4, 5, and 6 are line graphs plotting intensity along the height of each disc at the peak intensity in the polarization direction.
Figure 5:
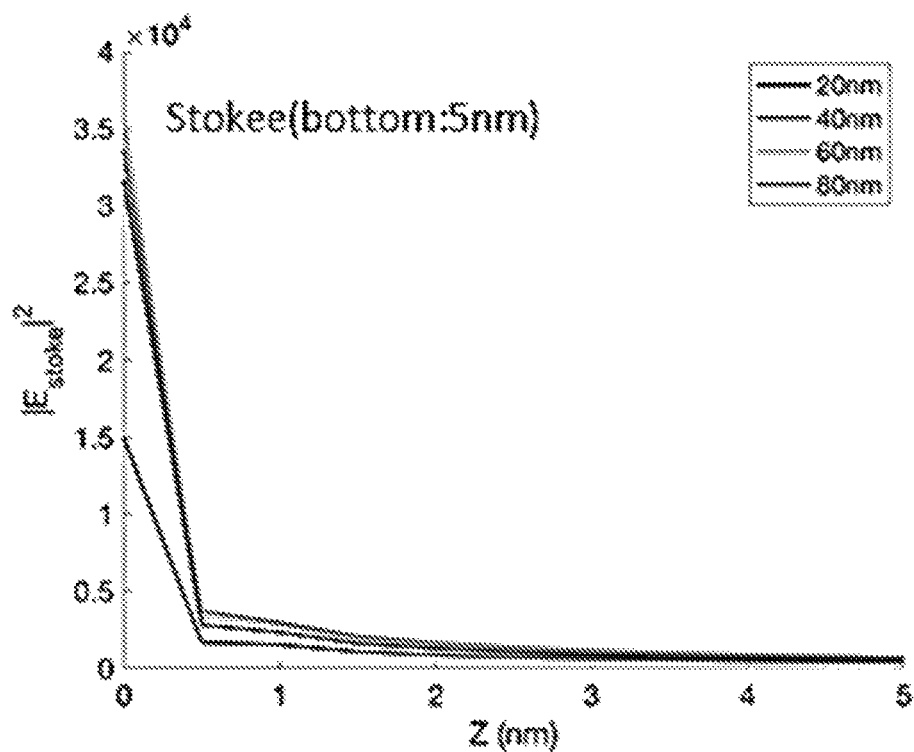
Figure 6:
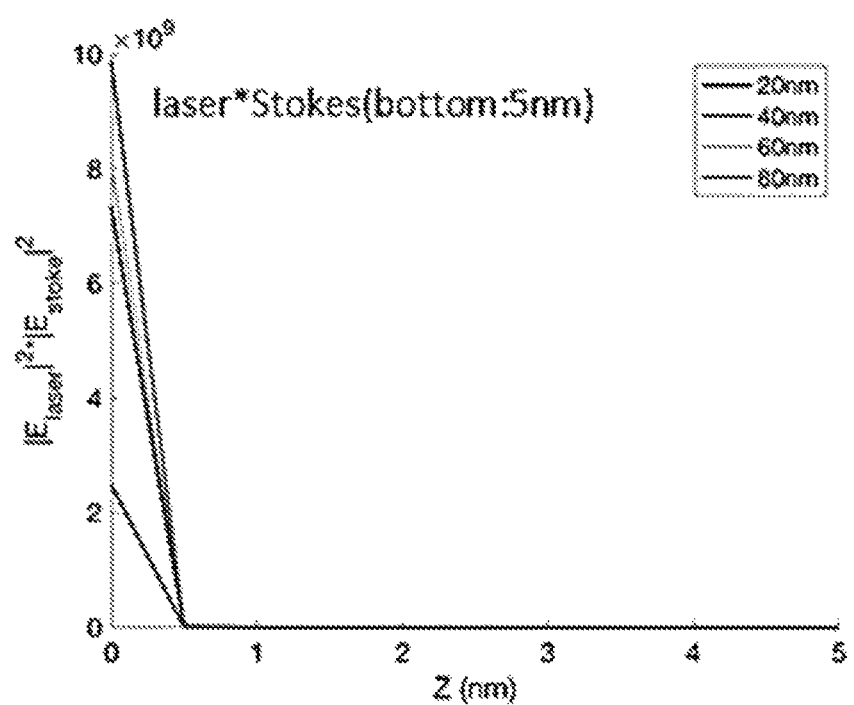
Figure 7:
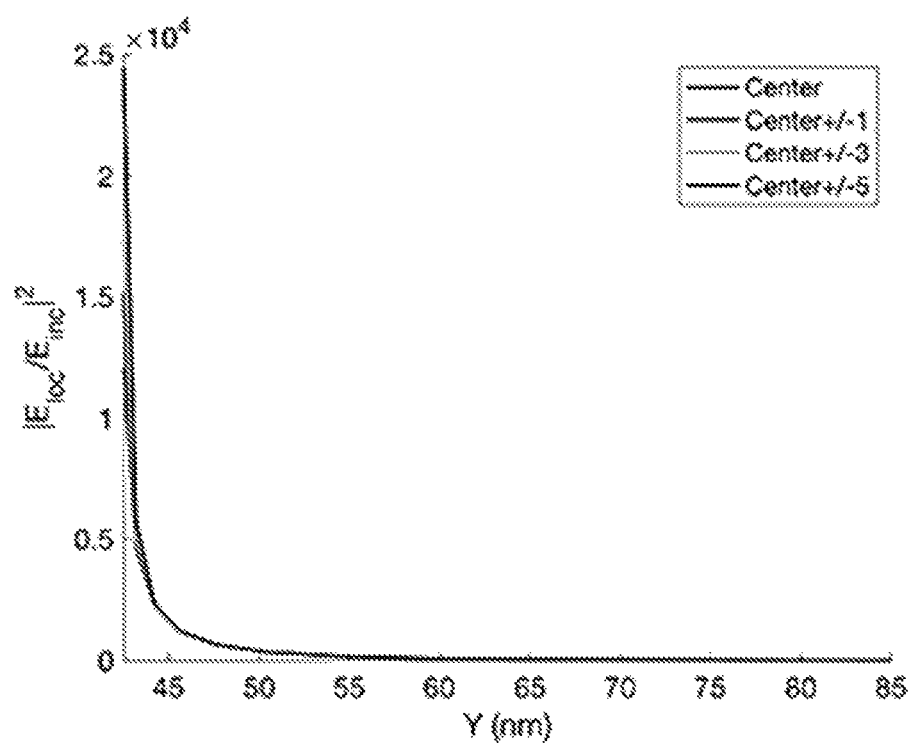
FIGS. 7, 8, 9, and 10 are line graphs plotting intensity at a 633 nm pump wavelength radially away from each disc just at a bottom surface of the disc.
Figure 8:
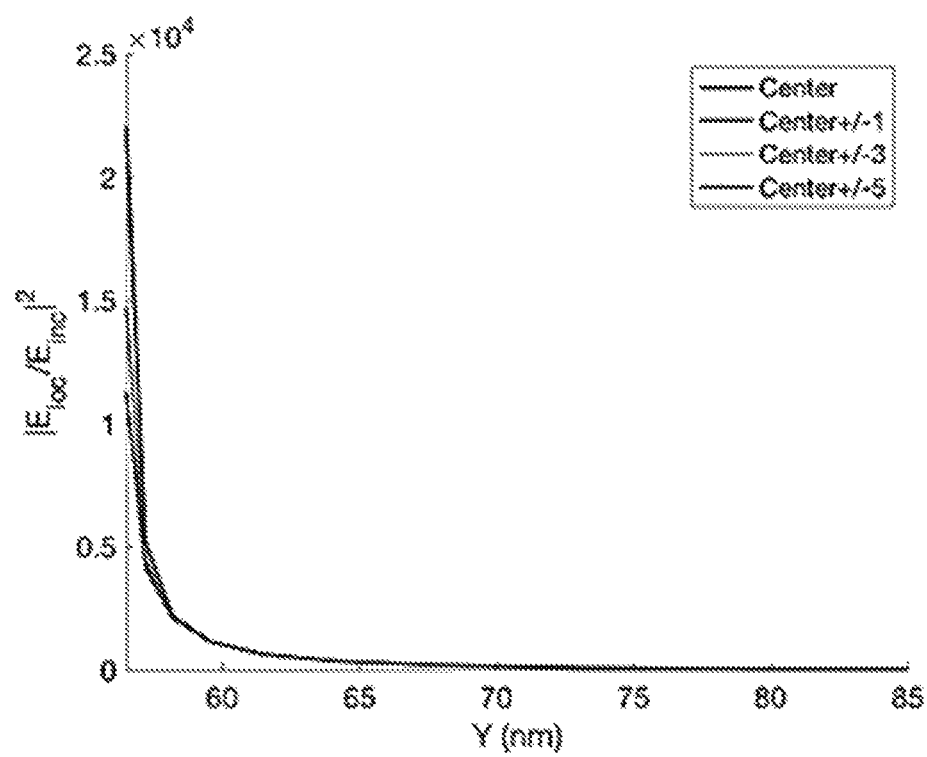
Figure 9:
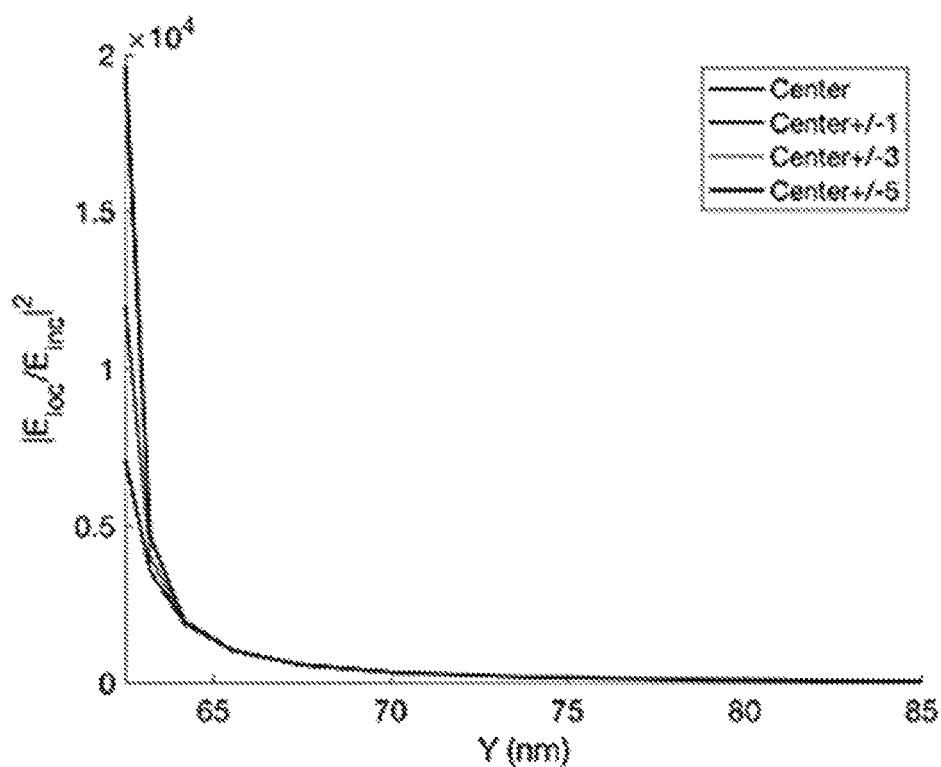
Figure 10:
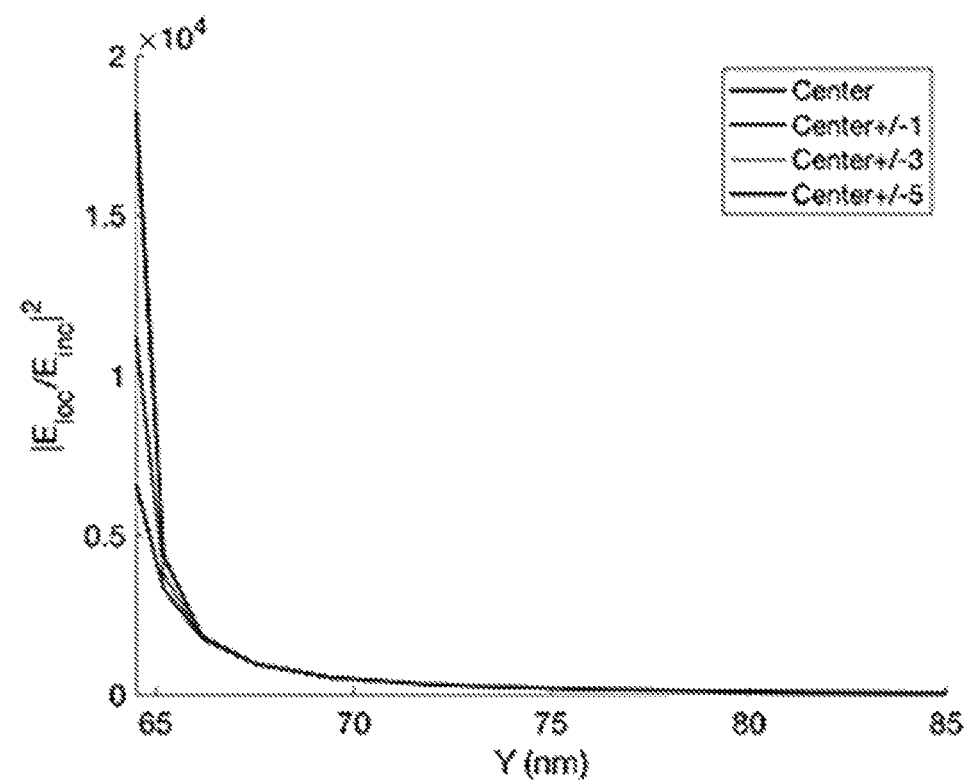

The hot spot is at the bottom of the disc, just at the interface with the glass substrate and is localized to a height of less than 1 nm along the direction of the laser polarization, as illustrate in FIGS. 4, 5, and 6 and to a comparable radial extent away from the disc, as shown in FIGS. 7, 8, 9, and 10. Around the disk, the intensity enhancement follows a $\cos^2(\theta)$ dependence where $\theta=0$ is defined along the laser polarization direction at normal incidence. In each of these plots, polarization direction of the pump laser beam is in the plane of the plot.

FIGS. 4, 5, and 6 are line graphs plotting intensity along the height of each disc at the peak intensity in the polarization direction. FIGS. 7, 8, 9, and 10 are line graphs plotting intensity at a 633 nm pump wavelength radially away from each disc just at a bottom surface of the disc.

Figure 11:
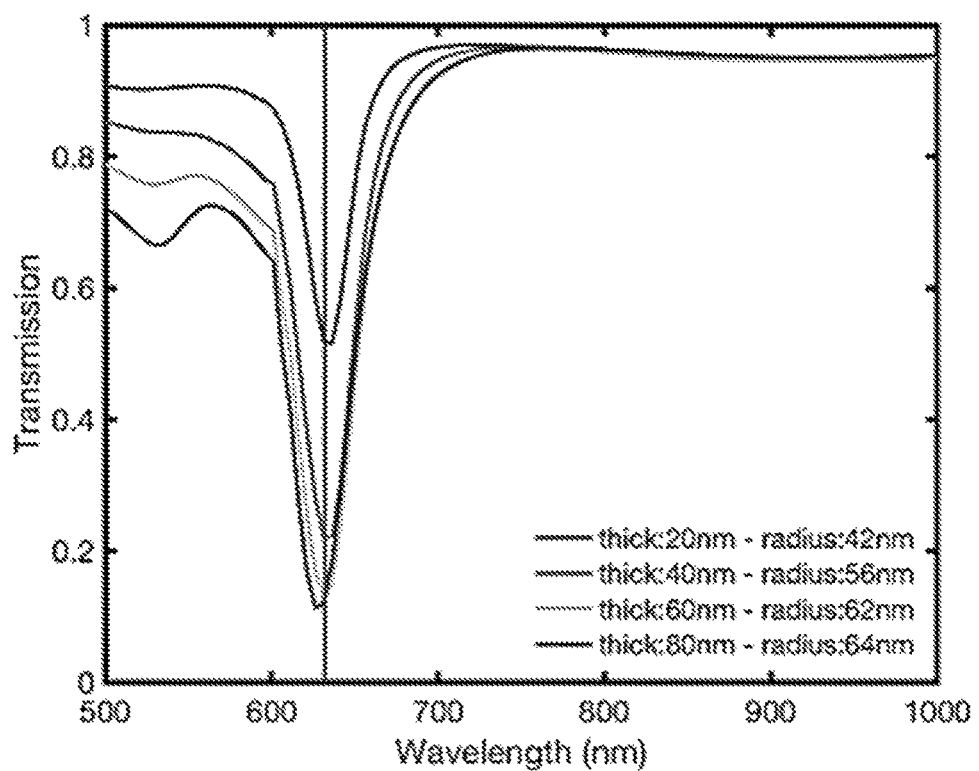
FIGS. 11 and 12 are lines graphs illustrating simulated transmission and field enhancements, respectively, for the four designs of FIGS. 3A-3D.
Figure 12:
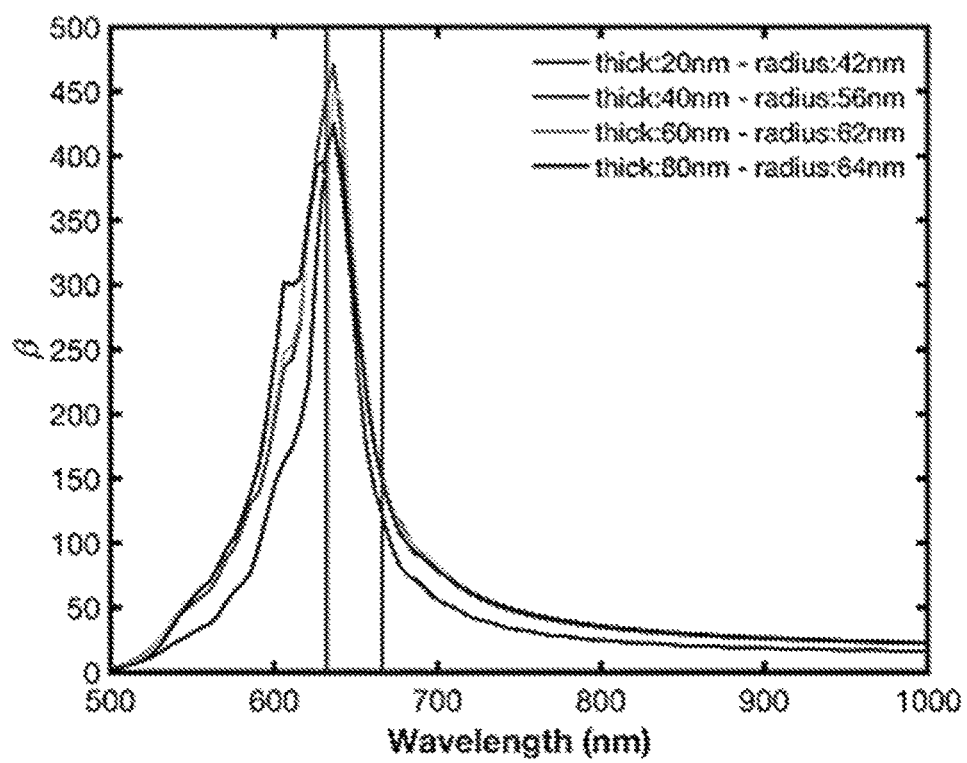

FIGS. 11 and 12 show the simulated transmission and peak field enhancement ($\beta=E_{disc}/E_{incident}$) for each of the four designs of FIGS. 3A-3D. As seen from the transmission curve, the resonance wavelength is maintained at 633 nm for all four structures. The maximum field enhancement at the hot spot is shown in the curve with the vertical axis labeled as $\beta$, the ratio of the maximum field to the applied field. As seen, this $\beta$ is independent of the thickness of the Au disk as long as the resonance position is adjusted. The vertical line at 633 nm corresponds to the pump wavelength, we assume a Raman shift of 1000 cm$^{-1}$ so the Stokes wavelength is 666 nm. The overall enhancement factor (EF) is $[\beta(\omega_P)\beta(\omega s)]^2$ Roughly, $\beta(\omega_P)$~450 and $\beta(\omega s)$~125 giving an overall EF~$3\times10^9$. This value is in the range that has been used to demonstrate single molecule sensitivity.

The present invention recognizes that enhanced single molecule detection depends on the detailed structure near the electromagnetic hot spot which is localized and occurs at the interface of the bottom surface of the nanoscale metallic structure.

Certain materials, including gold (Au) and silver (Ag), do not adhere well to certain substrate materials, such as SiO$_2$, glass or the like. In conventional fabrication, most often a thin layer of titanium (Ti), nickel (Ni), or chromium (Cr) is deposited immediately before adding the gold layer to provide adhesion between the metal and the substrate. The use of these materials can result in significant loss at the pump and Stokes wavelengths. Since the electromagnetic hot spot is localized just at the layer interface, such a loss can have a significant effect on the enhancement. Accordingly, in some embodiments, a dielectric adhesion layer is deposited between the top surface of the substrate and the array of nanoscale metallic structures to thereby adhere the array of nanoscale metallic structures to the top surface of the substrate. In particular, the dielectric layer may include a metal oxide material, including at least one of silicon dioxide (SiO$_2$), magnesium oxide (MgO), and aluminum oxide (Al$_2$O$_3$), which generally reduces the amount of loss at Raman pump and Raman Stokes wavelengths, as compared to other materials commonly used in coupling metallic structures to a substrate.

Figure 13:
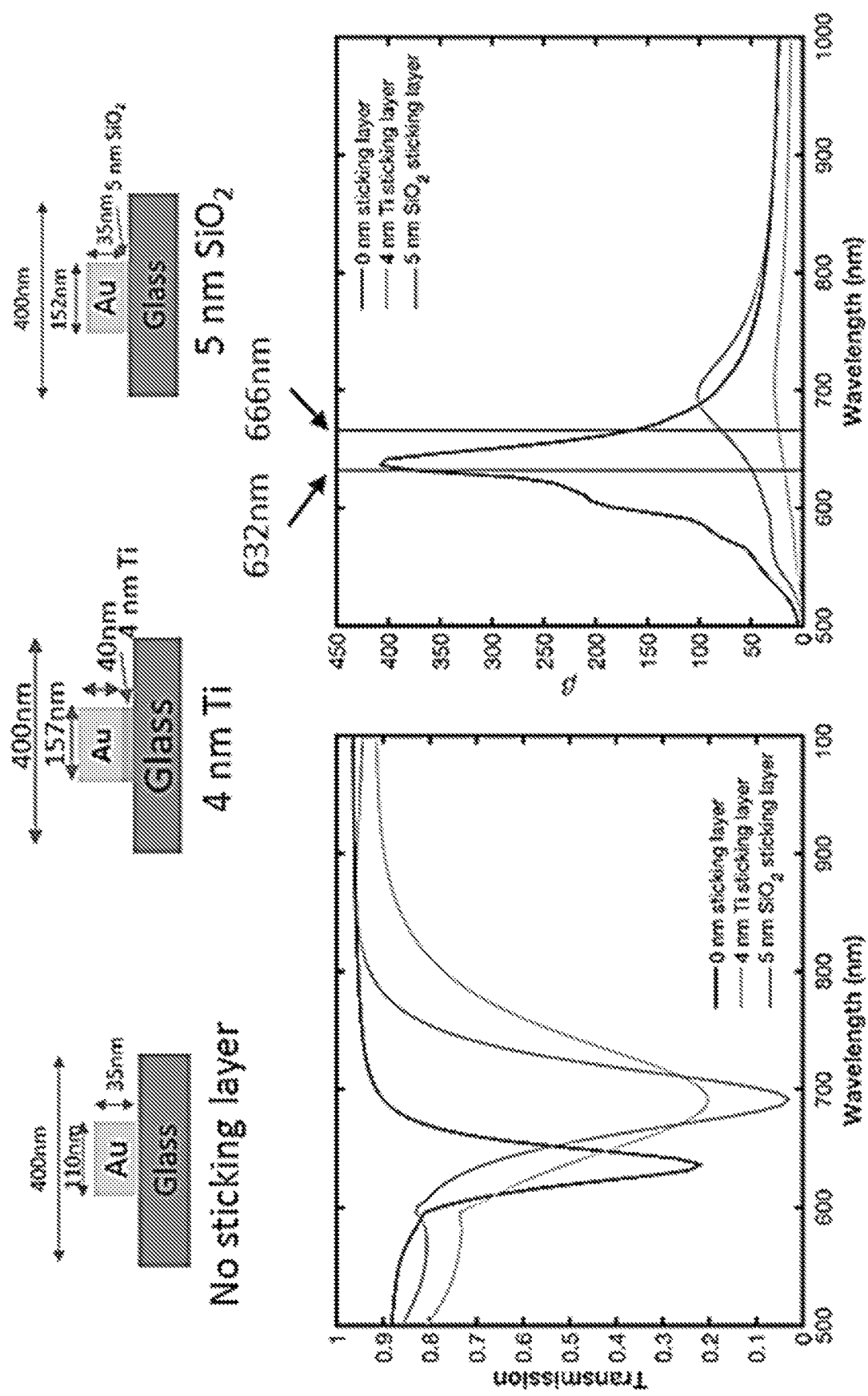
FIG. 13 illustrates the impact of utilizing a metal oxide material as an adhesion layer for adhering a metallic structure to the substrate of the enhancement structure of the present invention.

Simulation testing shows that the dielectric sticking layer material, such as SiO$_2$, leads to a significant improvement as compared with a metal such as Ti, Ni, or Cr, by reducing the amount of loss. FIG. 13 illustrates the impact of utilizing a metal oxide material as an adhesion layer for adhering a metallic structure to the substrate of the enhancement structure of the present invention.

Figure 14:
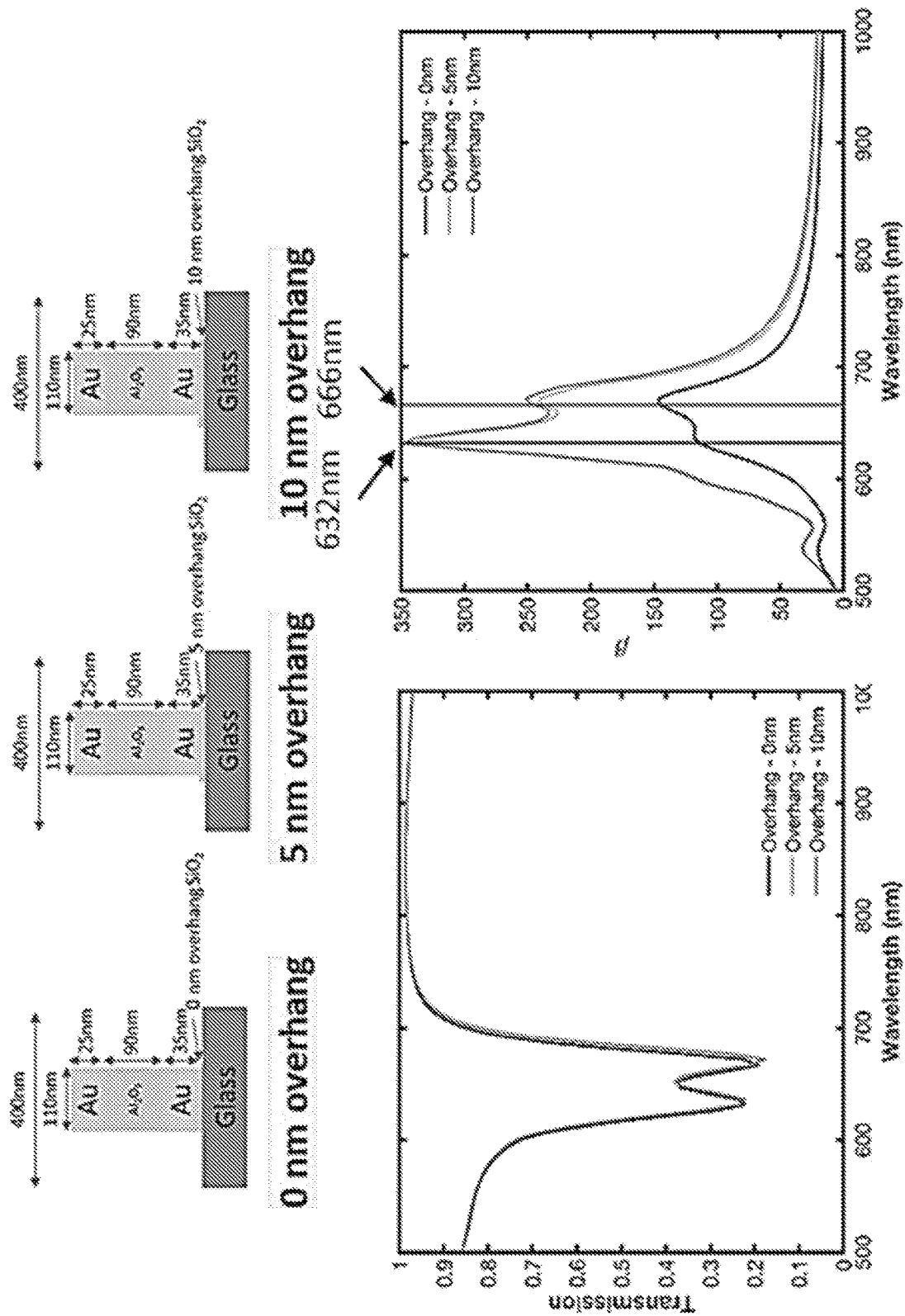
FIG. 14 illustrates the impact of extending the adhesion layer (sticking layer) beyond an MIM structure of the enhancement structure of the present invention.

FIG. 14 illustrates the impact of extending the adhesion layer (sticking layer) beyond an MIM structure of the enhancement structure of the present invention. For example, in some embodiments, the dielectric adhesion layer that adheres the nanoscale metallic structures to the substrate results in improved performance if portions of the adhesion layer extend beyond the bottom surface of the metallic structures. In particular, in some embodiments, each of the array of nanoscale metallic structures is adhered to the top surface of the substrate via a separate dielectric adhesion layer. In such an embodiment, at least some of the adhesion layers have a surface area that is greater than the bottom surface area of the nanoscale metallic structure such that a portion of a dielectric layer extends beyond a perimeter of the bottom surface of the respective nanoscale metallic structure. Accordingly, the dielectric adhesion layer may include an overhanging configuration. As illustrated in FIG. 14, it is clear that the enhancement is strongly increased by increasing the overhang of the sticking layer beyond the MIM structure. An object of this invention is to provide and demonstrate a fabrication sequence for realizing this enhancement. In particular, there is a factor of 3 improvement in $\beta(\omega_p)$ and a factor of 2 improvement in $\beta(\omega s)$ giving an overall improvement in the EF of $3^2\times2^2=36$ from this simple change in the structure.

Figure 15:
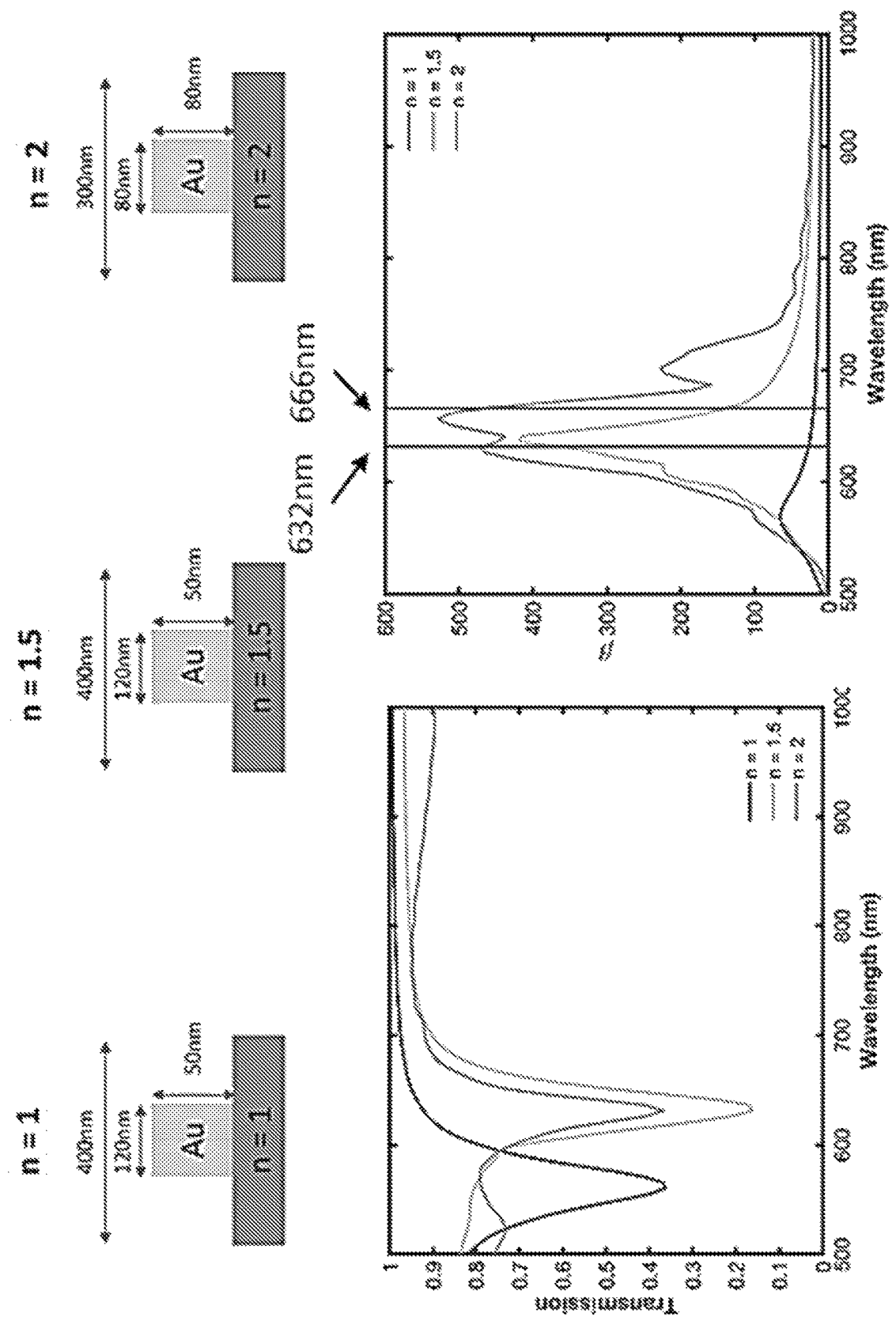
FIG. 15 illustrates the impact and variation in the enhancement when using substrates having different refractive indices.

FIG. 15 illustrates the impact and variation in the enhancement when using substrates having different refractive indices. The refractive index of the substrate also plays a major role in the enhancement. FIG. 15 includes calculations for substrate indices of 1 (air), 1.5 (glass) and 2.0 (Si3N4). The enhancement is roughly symmetric on the top and bottom surfaces of the Au disk for an air substrate, there is a small variation due to retardation effects associated with the finite thickness of the disc relative to the wavelength. For a glass substrate, the field strength is significantly higher at the bottom of the disc compared with the top surface. The field enhancement is slightly improved for the silicon nitride substrate, and is significantly broader, so that the overall SERS enhancement factor will be much higher.

Figure 16:
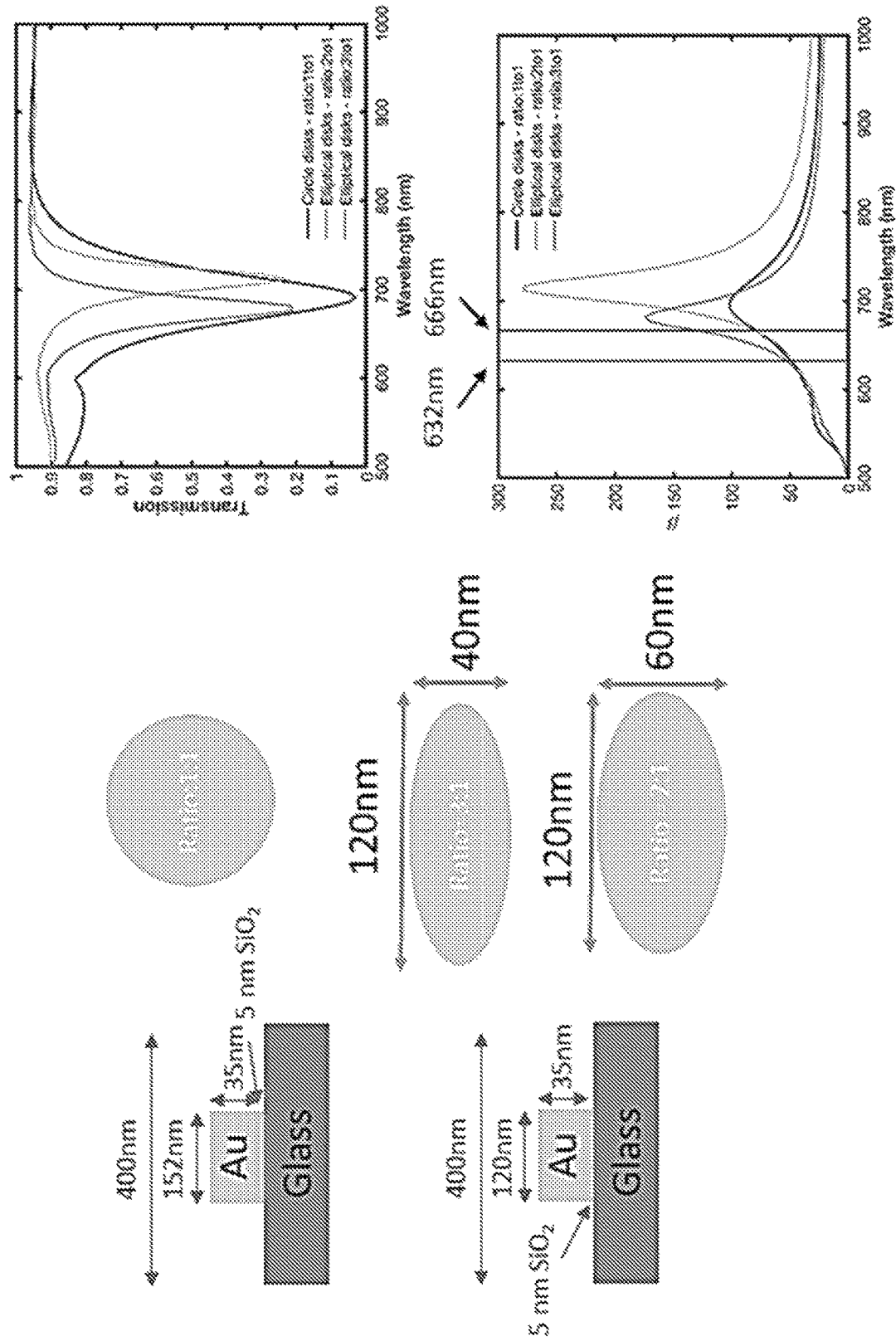
FIG. 16 illustrates the impact of utilizing an elliptical-shaped disc as opposed to a circular-shaped disc with the enhancement structure of the present invention.

It is also possible to increase the enhancement by changing the shape of the disc structure from circular to elliptical, as is shown in FIG. 16. The structures illustrated in FIG. 16 have not been adjusted to shift the resonances to the pump wavelength. However, it is clear that there is a substantial gain by increasing the curvature along the polarization direction. These results are for a 5-nm thick SiO$_2$ adhesion layer and can be increased by combining the extended dimensions of the adhesion layer as shown in FIG. 14.

Figure 17:
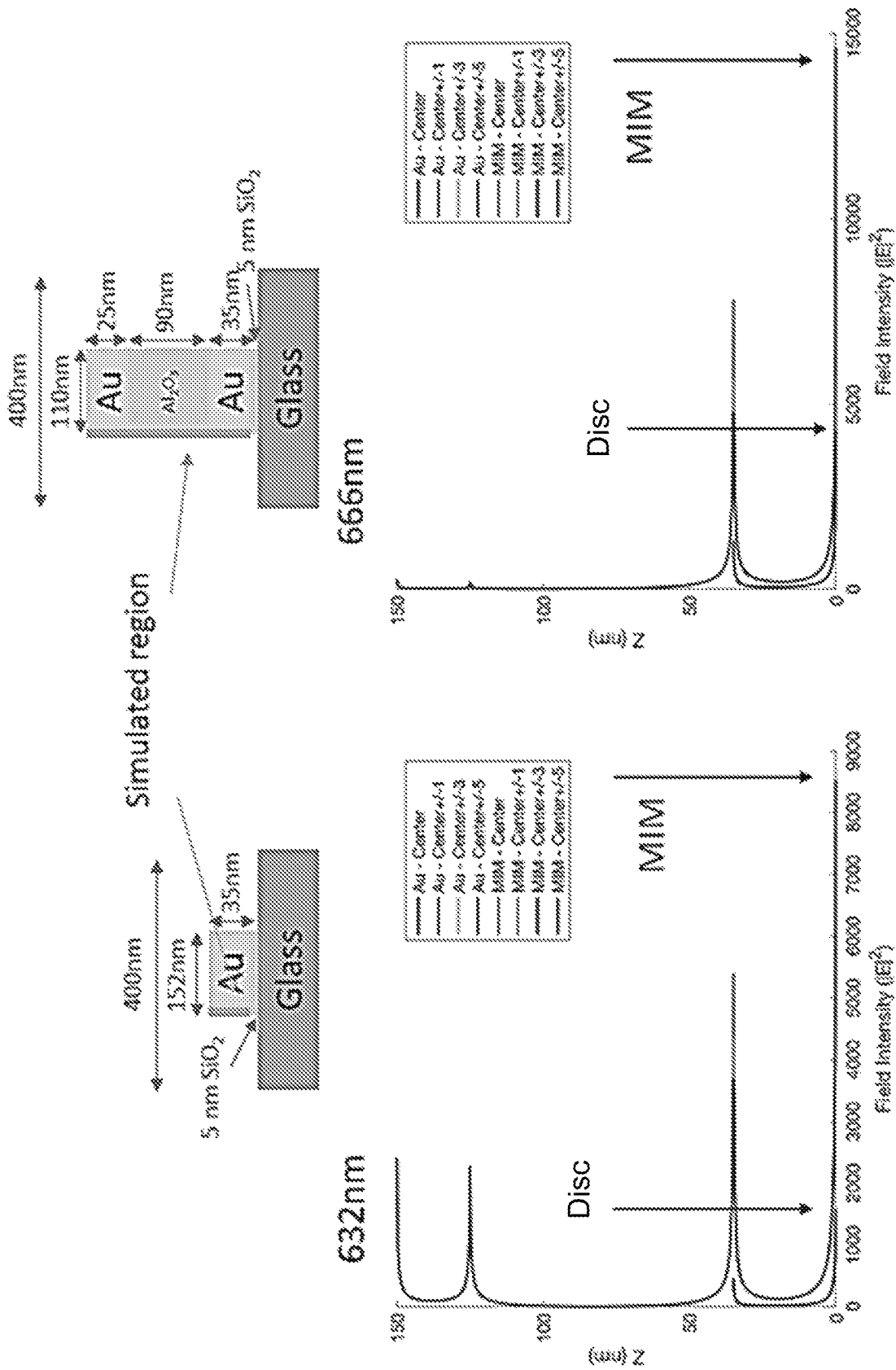
FIG. 17 illustrates a simulated field enhancement for both an individual disc and a MIM structure, each of which includes an adhesion layer of silicon dioxide, consistent with the present invention.
Figure 18A:
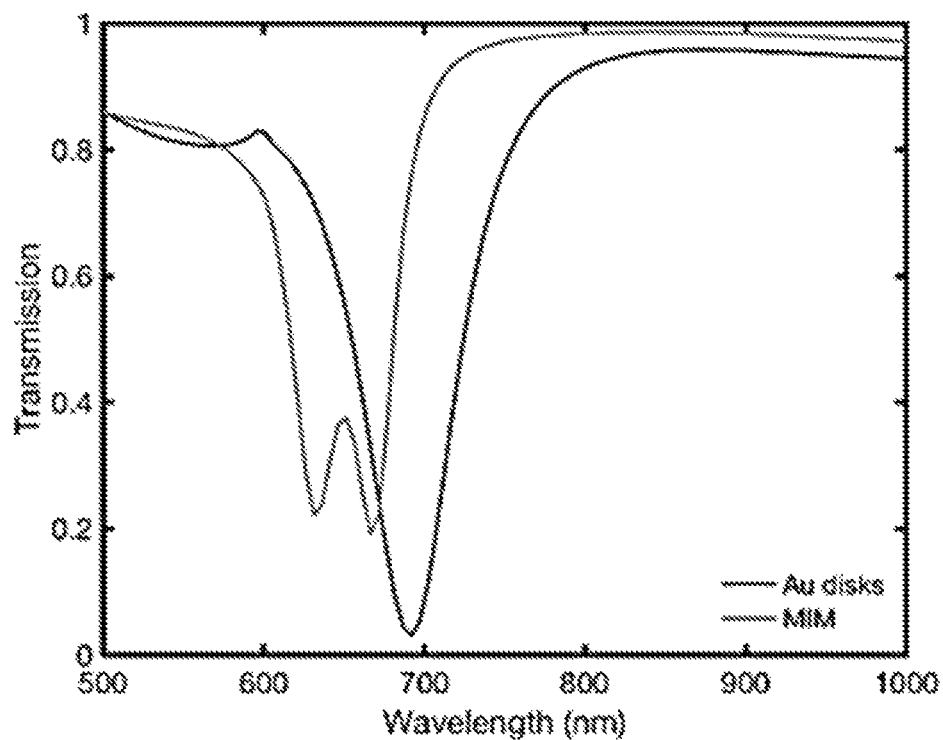
FIGS. 18A and 18B show simulated transmission and maximum enhancement, respectively, for individual disc and a MIM structures of FIG. 17.
Figure 18B:
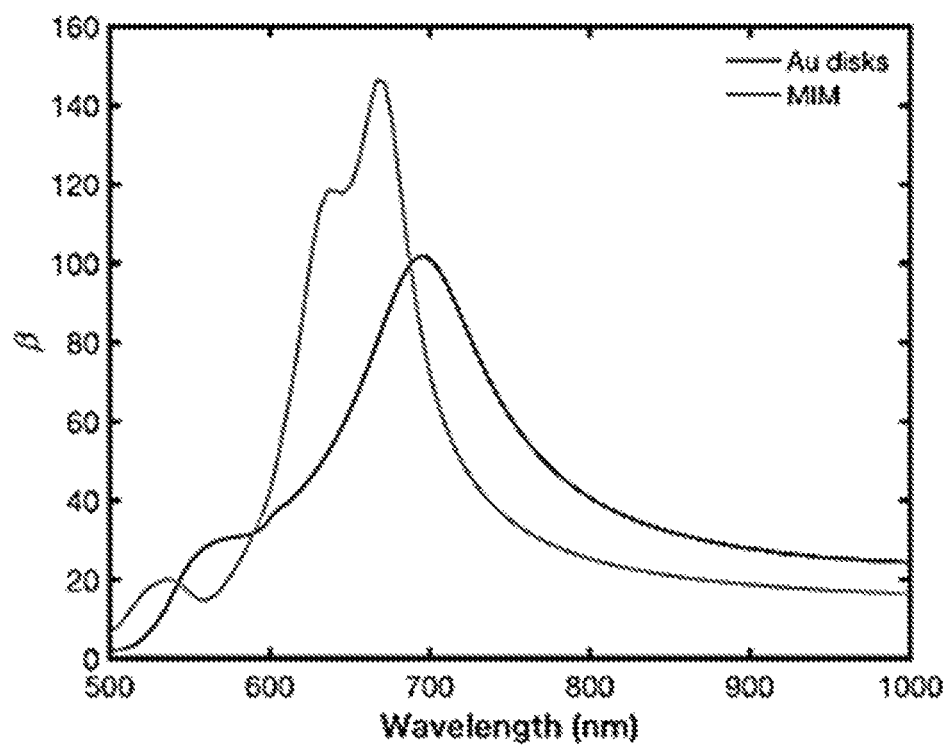

The field enhancement can be improved with more complex structures. In particular a metal-insulator-metal (MIM) structure adds a magnetic dipole resonance as a result of the current loop than can be sustained between the two metal discs. This can both add to the strength of the electric dipole resonance of the disk and provide a second resonance that can be tuned to be at the Stokes wavelength significantly adding to the enhancement. This is shown in FIG. 17, which compares the electric field enhancement along the height of the structure for a simple disc and an MIM structure. The disc geometry was adjusted to provide the electric dipole resonance and 633 nm. The thickness of the insulator in the MIM was adjusted to place the magnetic dipole resonance at the 666 nm Stokes wavelength. The simulated transmission and spectral enhancement ($\beta$) curves are shown in FIGS. 18A and 18B. As seen in FIG. 17, for both structures there is a strong enhancement of the field at each interface. The enhancements are significantly larger for the MIM as compared with the disc.

While the overhang shown in FIG. 14 provides significant improvement in the overall enhancement, it can be difficult to fabricate, requiring several extra fabrication steps. A simpler solution is to deposit a final SiO2 film over the MIM structure. The idea is to match the thickness of the dielectric sticking layer so that there is no dielectric discontinuity at the edge of the sticking layer. The top layer, above the MIM, is not expected to substantially affect the strength of the hot spot at the interface between the bottom metal and the sticking layer. This has been verified by simulation and experiment.

Figure 19A:
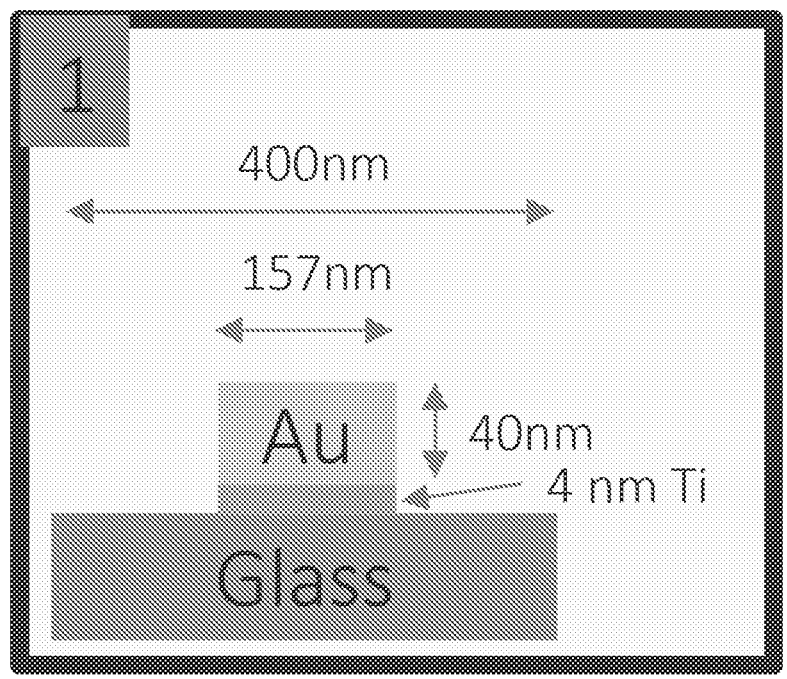
FIGS. 19A, 19B, 19C, 19D, and 19E illustrate various enhancement structure designs.
Figure 19B:
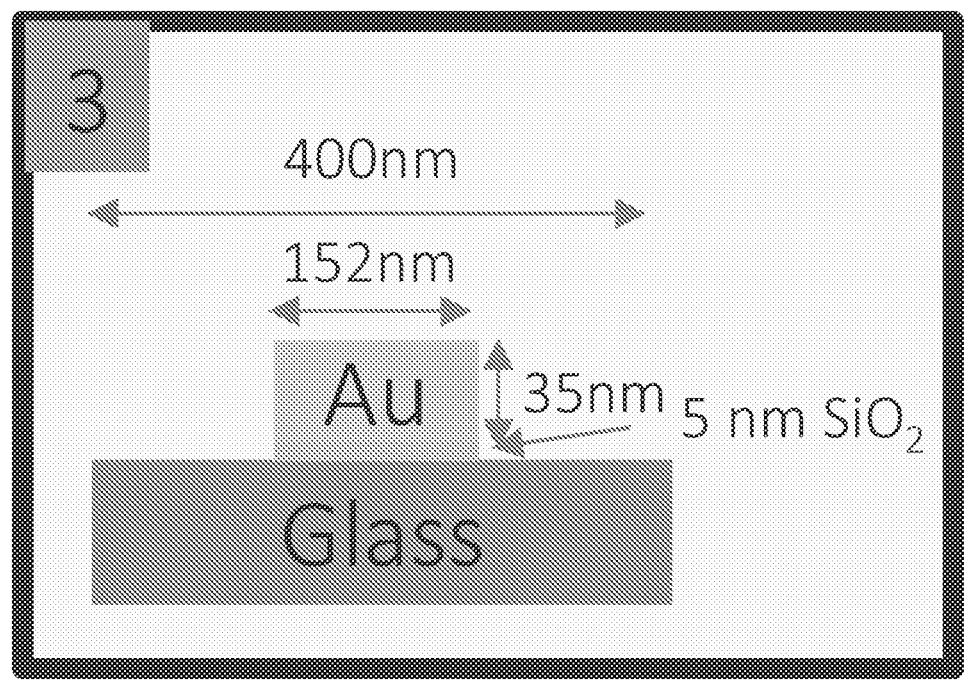
Figure 19E:
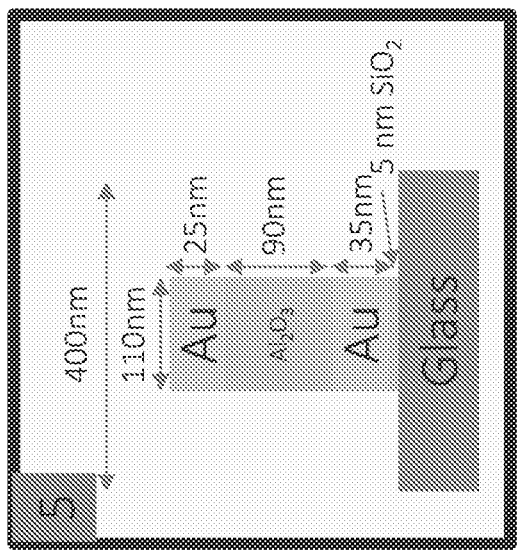
Figure 19D:
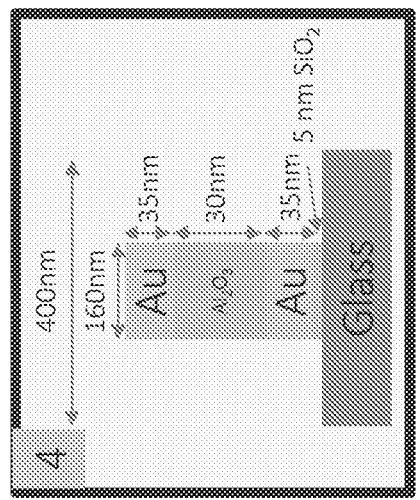
Figure 19C:
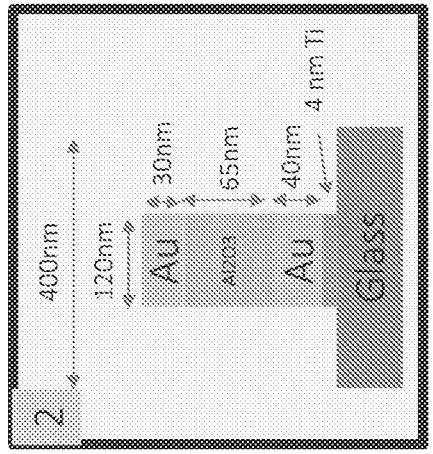
Figure 20A:
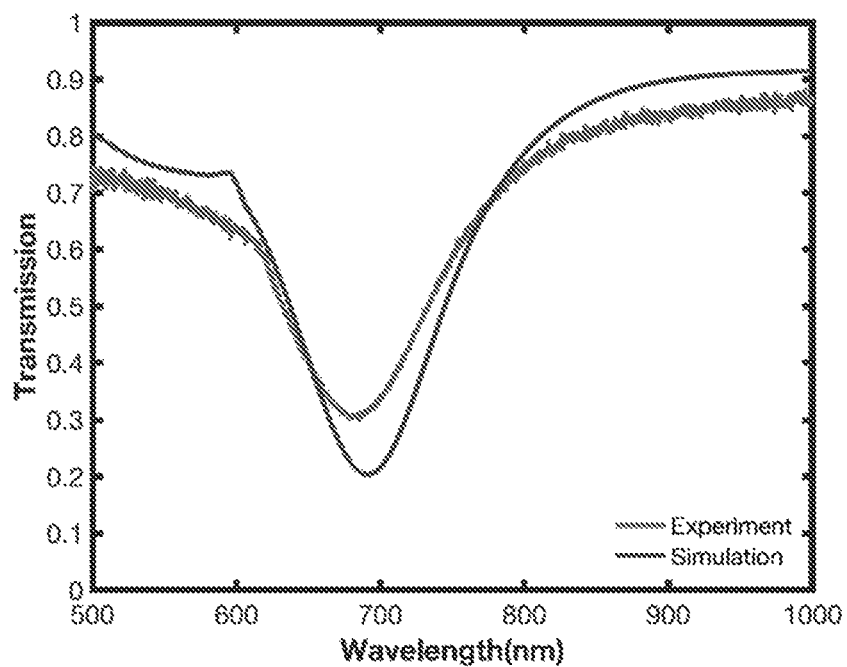
FIGS. 20A, 20B, 20C, 20D, and 20E show transmission analysis (both simulation and experimental) of each of the enhancement structure designs of FIGS. 19A-19E, respectively.
Figure 20B:
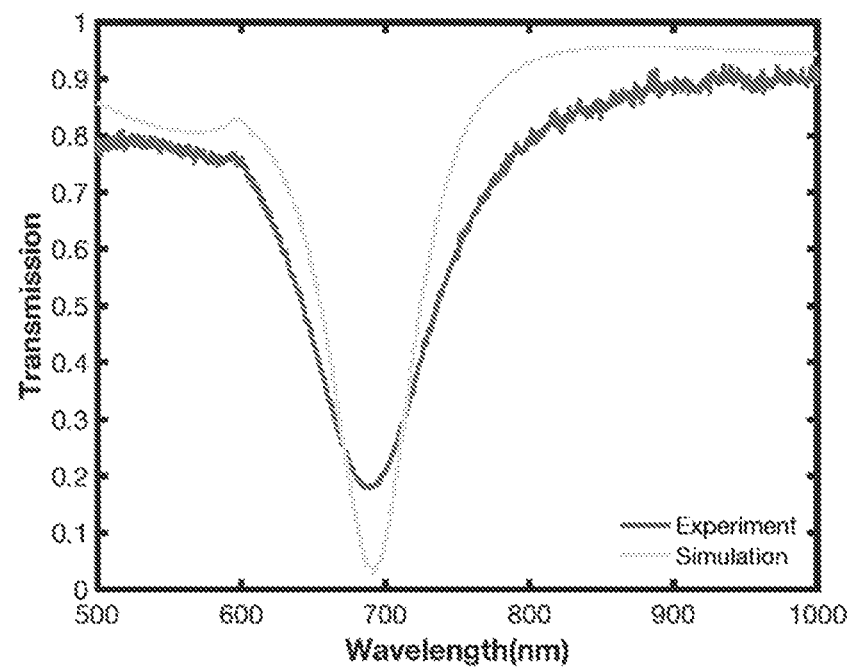
Figure 20C:
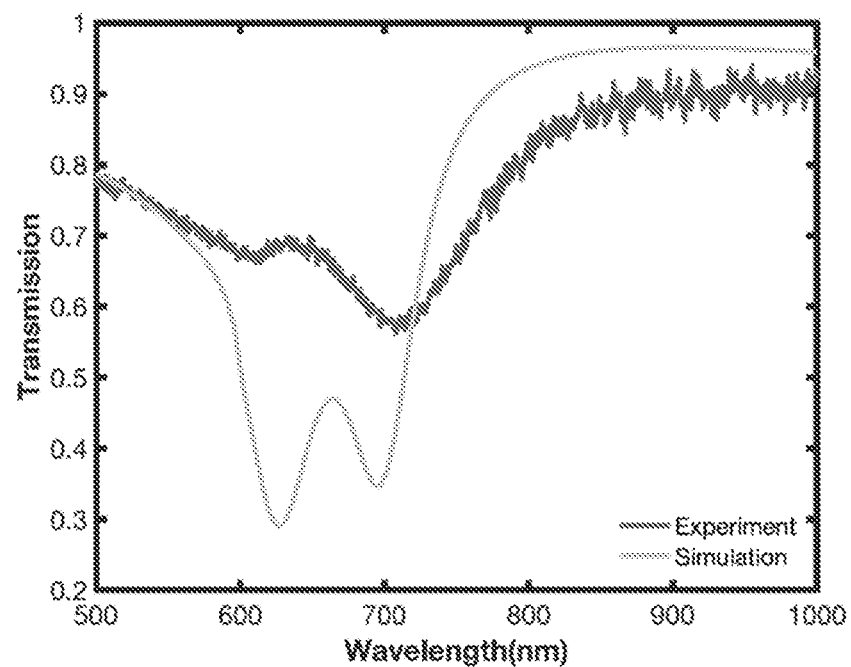
Figure 20D:
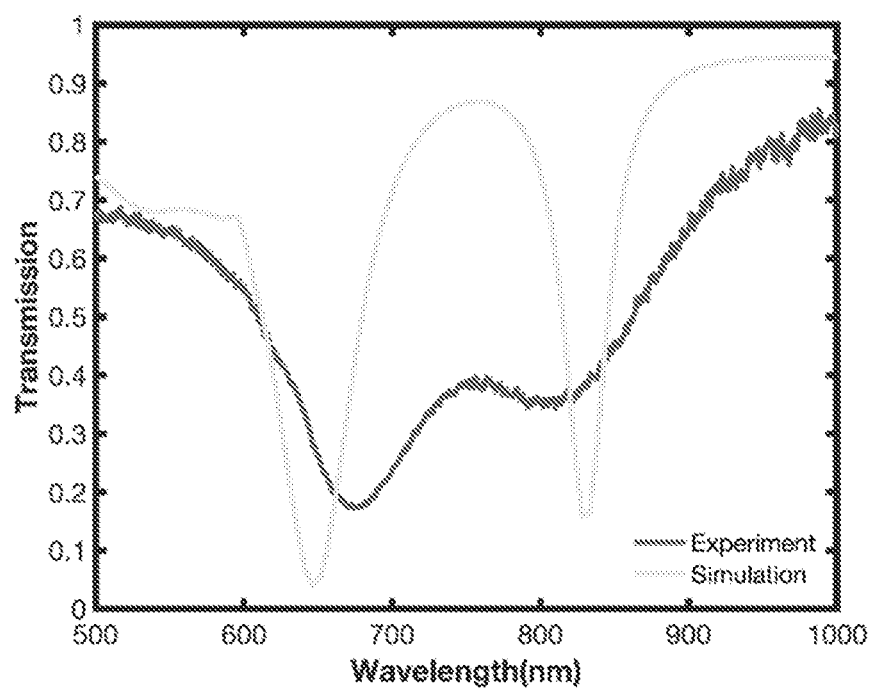
Figure 20E:
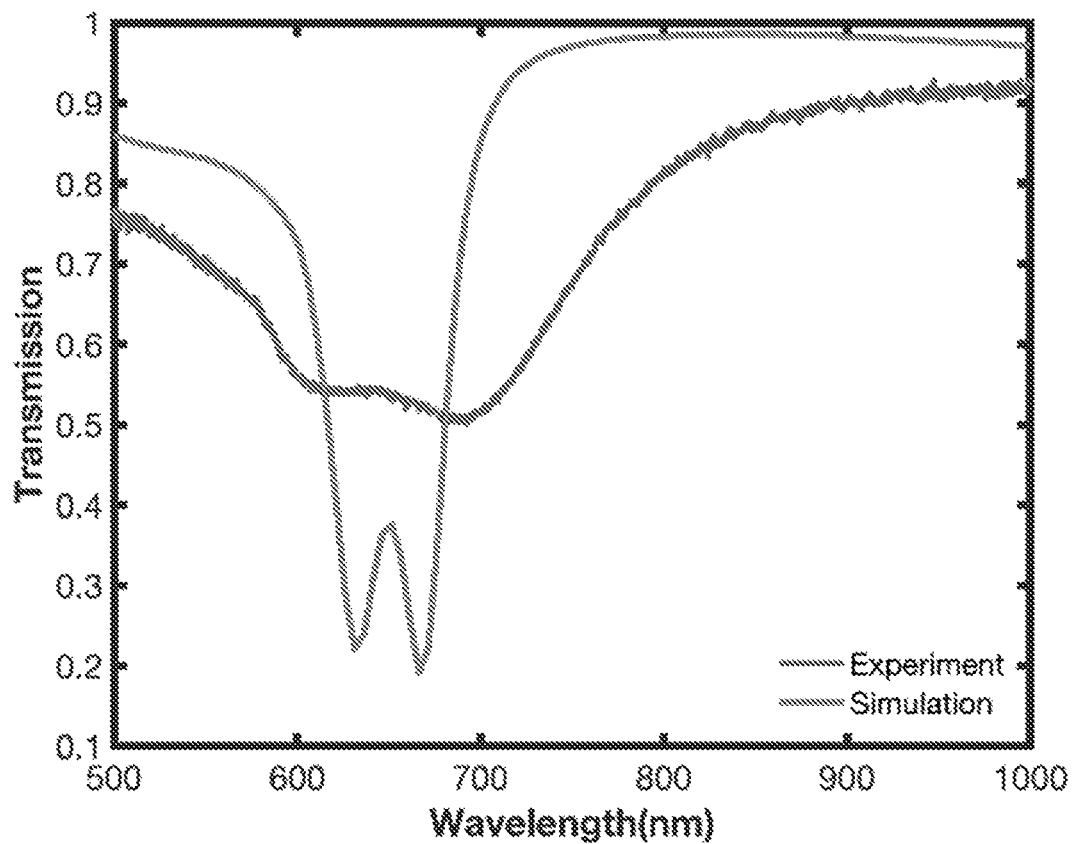
Figure 21:
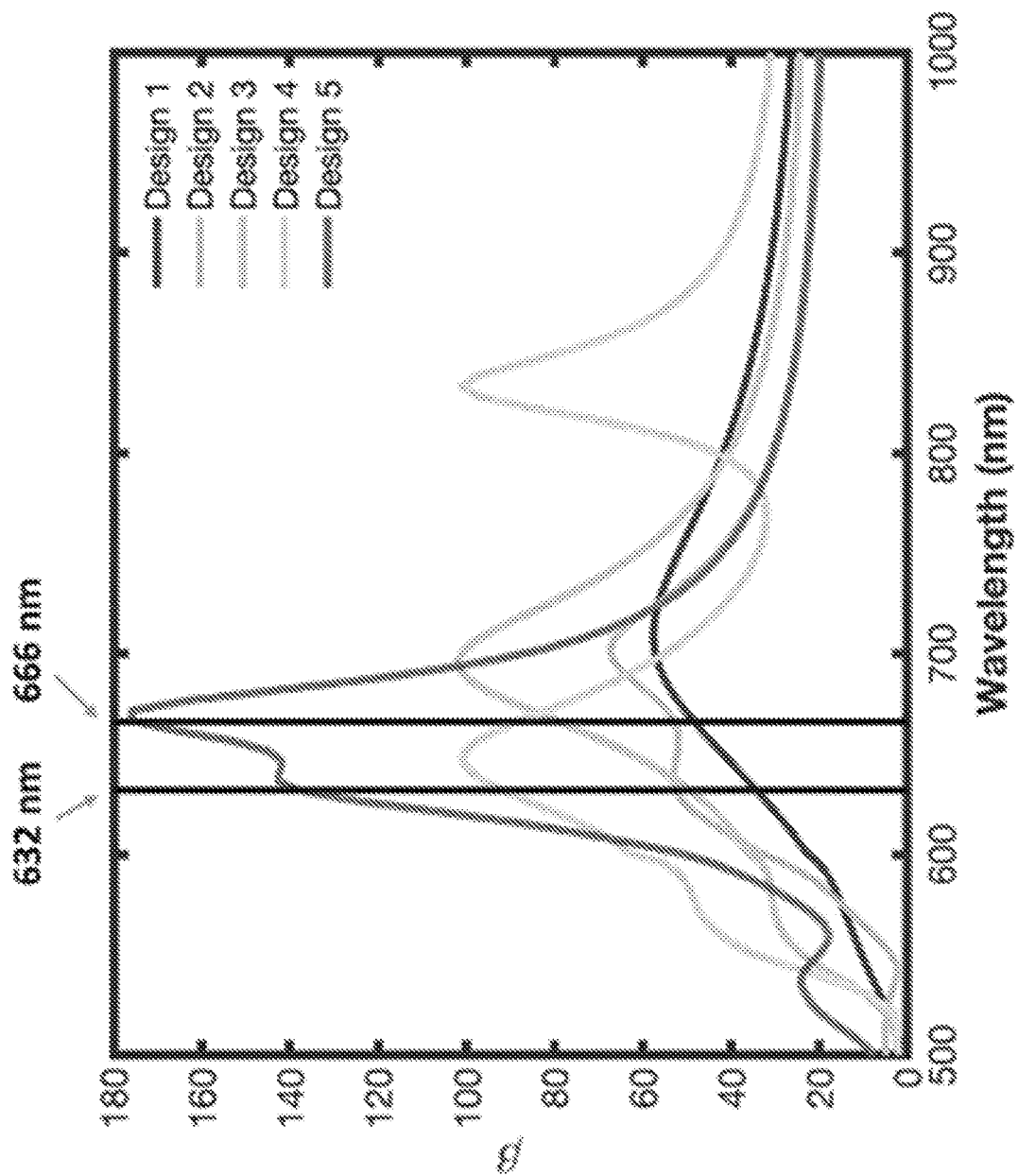
FIG. 21 shows simulated field enhancement of the enhancement structure designs of FIGS. 19A-19E.

FIGS. 19A, 19B, 19C, 19D, and 19E illustrate various enhancement structure designs. FIGS. 19A and 19B illustrate enhancement structures including a disc or pillar, but mainly differ in that the disc of FIG. 19A is adhered to the surface of a glass substrate via a titanium layer while the disc of FIG. 19B is adhered to the surface of a glass substrate via a silicon dioxide layer. FIGS. 19C-19E illustrates enhancement structures that include a MIM configuration. The MIM structure of FIG. 19C is adhered to the surface of a glass substrate via a titanium layer, while the MIM structures of 19D and 19E are adhered to the surface of a glass substrate via a silicon dioxide layer. Furthermore, the dimensions of the layers of the MIM structures of FIGS. 19D and 19E differ. FIGS. 20A, 20B, 20C, 20D, and 20E show transmission analysis (both simulation and experimental) of each of the enhancement structure designs of FIGS. 19A-19E, respectively. FIG. 21 shows simulated field enhancement of the enhancement structure designs of FIGS. 19A-19E. It is clearly important to benchmark these simulations against experimental results. The precise details of the structure just at the bottom interface with the substrate are important and somewhat variable with fabrication. Additionally, the simulation is based on a simple continuum models for the dielectric properties that are questionable at scales that are approaching chemical bond lengths. The simulated $\beta$ vs $\lambda$ curves are shown in FIG. 21. The experiment used a tri-phosphate DNA base (dCTP) that was spun onto the samples at 4000 rpm. Under these conditions, no Raman signal is observed for a clean glass substrate, so all of the experimentally observed signal is due to SERS enhancement.

Figure 22:
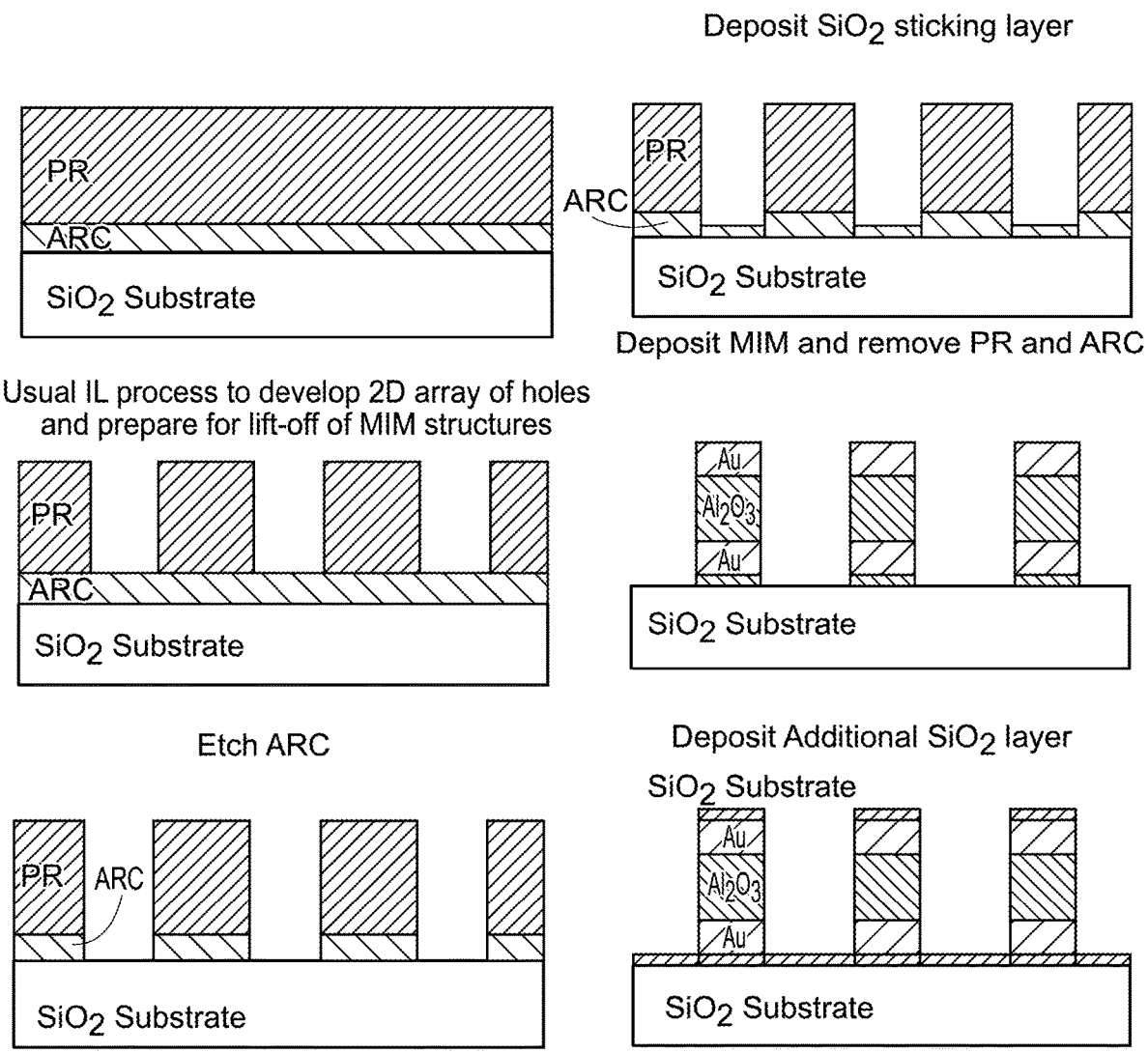
FIG. 22 illustrates a process for fabricating an embodiment of an enhancement structure including an array of MIM structures consistent with the present invention.

FIG. 22 illustrates a process for fabricating an embodiment of an enhancement structure including an array of MIM structures consistent with the present invention. The fabrication process begins with providing an $SiO_2$ substrate. The sample is cleaned in a piranha solution to remove all organic contaminants and dust particles. Then, an anti-reflection coating (such as i-CON-7) is spun on at 4000 rpm for 40 s and baked at 175 C for 1 min, followed by spin-coating with negative photoresist (PR; NR7-500P) at 4000 rpm for 40 s and baking at 150 C for 1 min. Use optical lithography to produce a 2D array of holes in the PR layer. This step can employ either optical lithography with an exposure tool with a resolution commensurate with the desired hole dimension, or interferometric lithography.

In the experiment described herein, interferometric lithography and development is used to produce a 2D array of holes in a developed photoresist layer with a hole size around 110 nm and a period of 400 nm. An $O_2$ plasma is used next to etch the anti-reflection coating (ARC) layer at the bottom of the holes to clear to the substrate, and also remove any residual PR. Alternatively, a developable ARC can be used. Deposit in sequence: a <10 nm thick sticking layer, which can be one of $SiO_2$, $Al_2O_3$ or $Si_3N_4$ or other suitable material, with a deposition rate of 0.1 A/s; and the Au—$Al_2O_3$—Au with the deposition rate of 0.3 A/s under the evaporation pressure of $2\times10^{-6}$ Torr. The sample is then soaked in acetone overnight to remove (lift-off) the PR, and then etched in an $O_2$ plasma to remove the remaining ARC. Finally, an additional $SiO_2$ layer of approximately the same thickness as the sticking layer is deposited across the substrate with the deposition rate of 0.1 A/s and the evaporation pressure of $2\times10^{-6}$ Torr. This processing sequence produces a MIM structure with a more or less continuous $SiO_2$ film at the substrate surface, and with an additional <10-nm thick $SiO_2$ layer over the top metal of the MIM.

Figure 23:
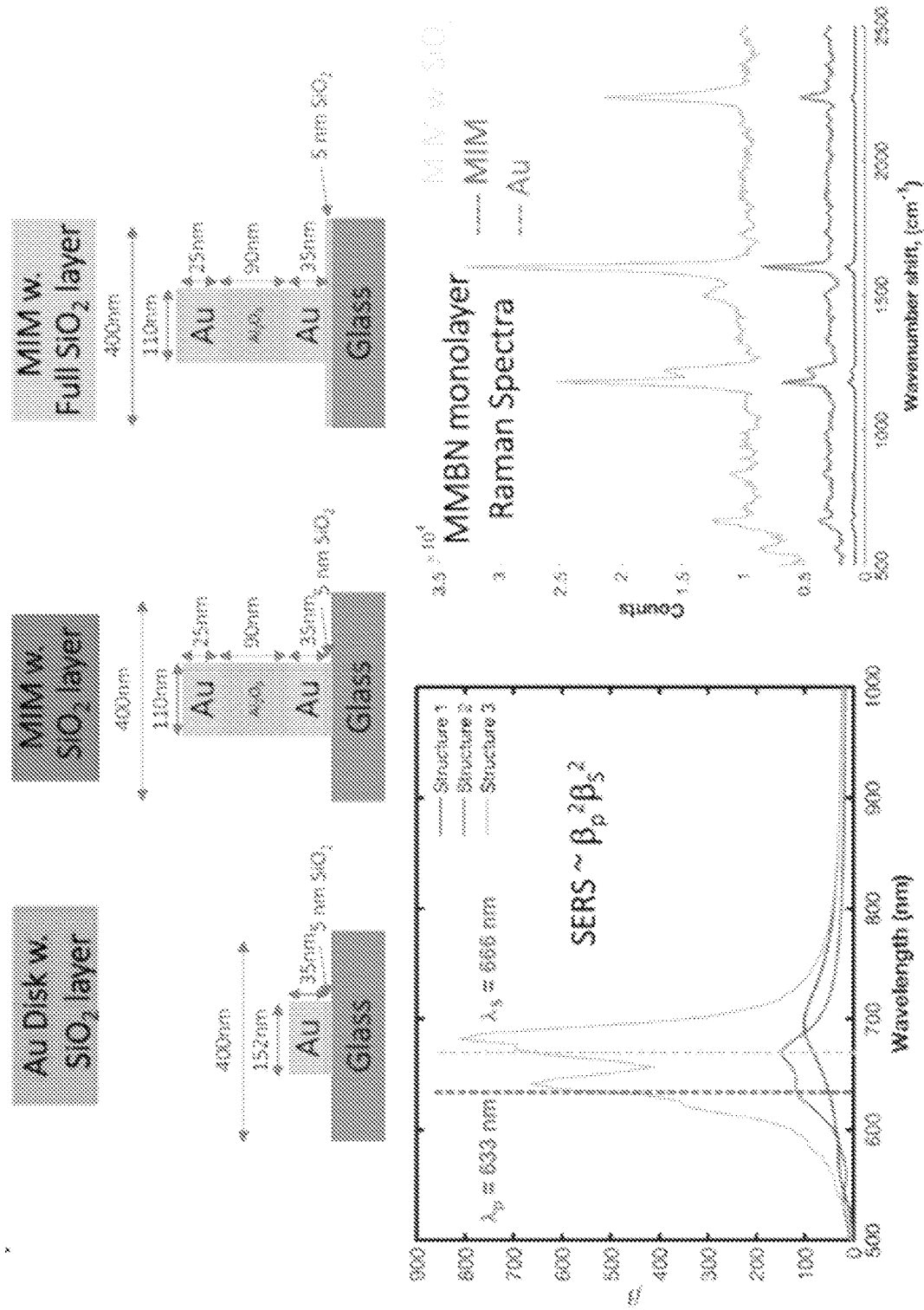
FIG. 23 shows simulated and experimental SERS results for a monolayer of MMBN (mercapto-methyl benzonitrile) molecules adsorbed onto three different enhancement structures consistent with the present invention.

FIG. 23 shows simulated and experimental SERS results for a monolayer of MMBN (mercapto-methyl benzonitrile) molecules adsorbed onto three different enhancement structures consistent with the present invention. In particular, FIG. 23 shows verification by simulation and experiment, and compares three structure arrays: a simple Au disk with a 5 nm $SiO_2$ sticking layer; a MIM structure with a 5 nm sticking layer; and the same MIM structure with the addition of a ~5 nm $SiO_2$ layer, to match the sticking layer and provide a more or less continuous bottom $SiO_2$ film, as illustrated in FIG. 22.

Also shown are the experimental Raman spectra of a self-assembled monolayer of 4-MMBN (mercapto-methyl benzonitrile, $C_8H_7NS$) adsorbed onto all Au surfaces. 4-MMBN is product #OTV000790 from Sigma-Aldrich. The monolayer is formed by soaking the sample in a 5 millimolar solution of 4-MMBN in ethanol for 24 hours and then extensively rinsing with ethanol to remove excess MMBN that is not bound to the Au surface through an Au-thiol bond. The experimental spectra were obtained at 0.2 mW laser power (HeNe) and 30 s collection time with the spot diameter (FWHM) of about 0.5 μm. Clearly, the SERS enhancement is larger for the MIM as compared with the Au disk and even larger with the additional $SiO_2$ deposition. Using a normalized metric of counts/mWs, the results are 84, 653, and 2793 for the 1200 $cm^{-1}$ Raman line, respectively. The nominal dimensions of the enhancement structures are given in the FIG. 23.

The excitation wavelength $\lambda_P$ was 633 nm and the Stokes wavelength was $\lambda_s$~685 nm for the 1200 $cm^{-1}$ Stokes Raman shift. The S/N of monolayer MMBN on these three structures are 9, 30, and 392, respectively. Clearly, the S/N has been improved from the Au disk to the MIM, and even further improved with the MIM that has full $SiO_2$ layer coverage across the sample. In the future work, a higher vacuum ($<1\times10^{-7}$ Torr) condition can be used for the $SiO_2$ layer deposition. This will improve the quality or uniformity of the $SiO_2$ layer coverage, and ultimately would further improve the S/N.

Figure 24:
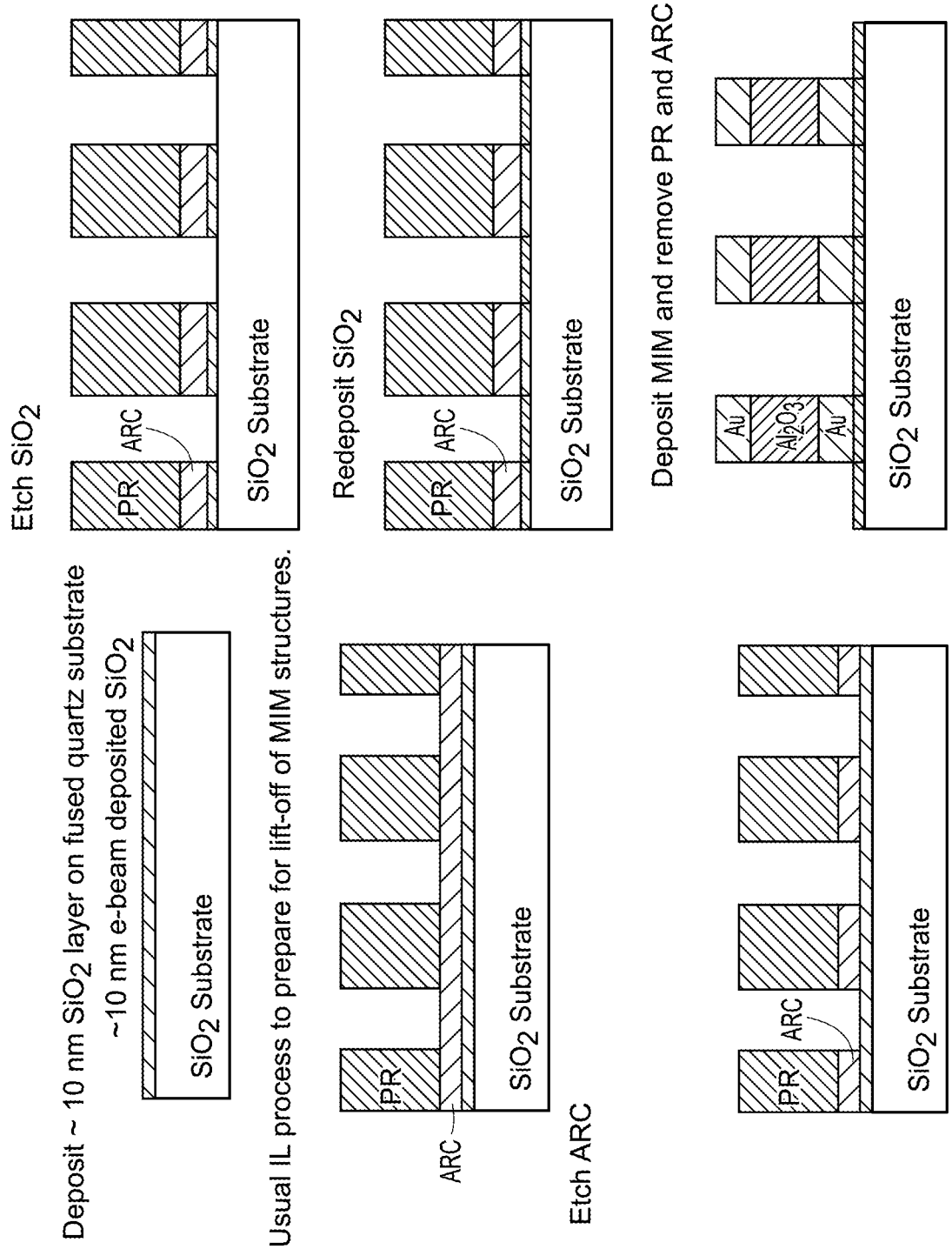
FIG. 24 illustrates another process for fabricating an embodiment of an enhancement structure including an array of MIM structures consistent with the present invention.

FIG. 24 illustrates another process for fabricating an embodiment of an enhancement structure including an array of MIM structures consistent with the present invention. In this embodiment, a thin, blanket layer of $SiO_2$ is deposited across the entire sample, followed by ARC and PR layers as in the description above. After developing the PR to produce a 2D array of holes, the ARC at the bottom of the holes is etched away, and $SiO_2$ is again deposited to form a sticking layer at the bottom of each hole. This is followed by deposition of the MIM structure and liftoff. The end result is a MIM structure with a continuous $SiO_2$ layer.

Figure 25:
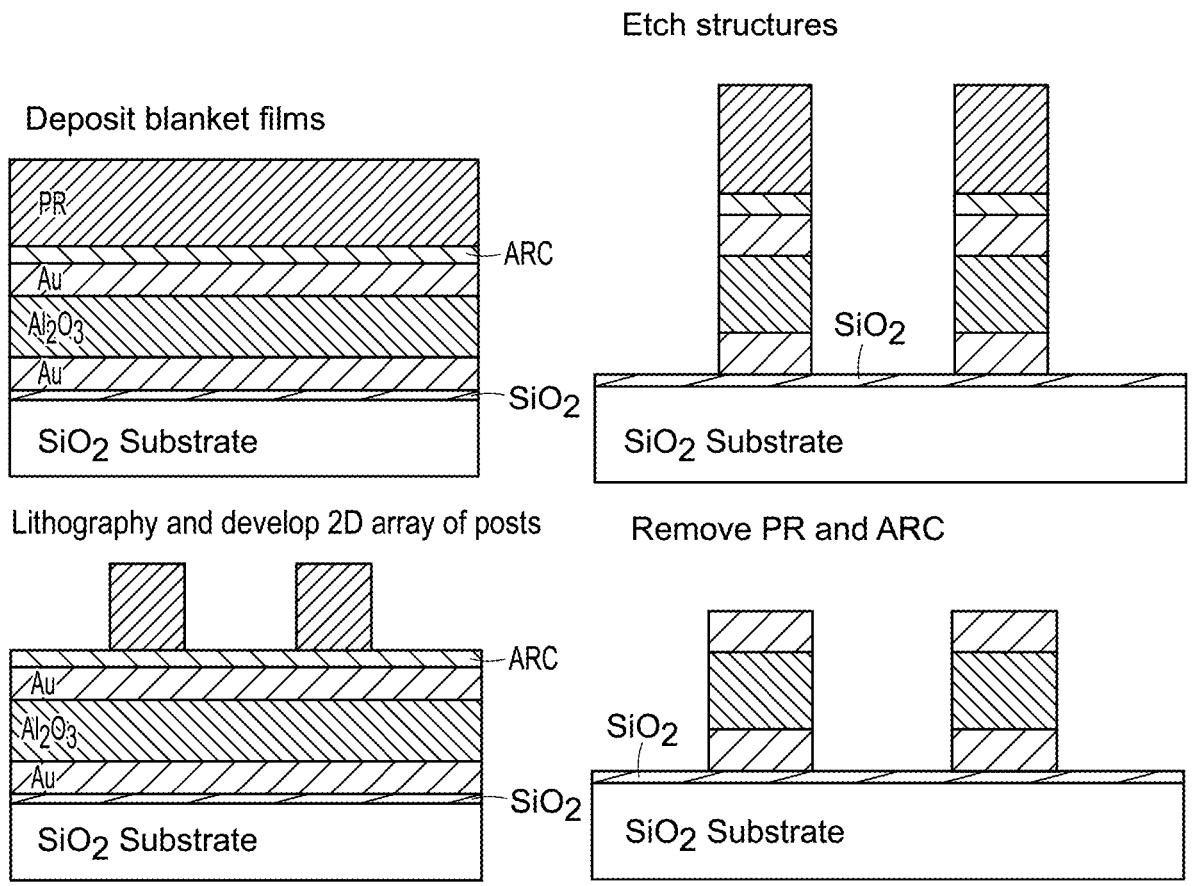
FIG. 25 illustrates a subtractive process for fabricating an embodiment of an enhancement structure including an array of MIM structures consistent with the present invention.

FIG. 25 illustrates a subtractive process for fabricating an embodiment of an enhancement structure including an array of MIM structures consistent with the present invention. In particular, FIG. 25 shows an embodiment where blanket films of $SiO_2$, Au, $Al_2O_3$, Au are deposited followed by a processing sequence to result in a 2D array of MIM posts atop a continuous sticking layer. It might be necessary to add a very thin $Al_2O_3$ layer atop the $SiO_2$ layer to serve as an etch stop. In other embodiments, the $Al_2O_3$ layer can be replaced with SiO$_2$ or Si$_3$N$_4$ and the dimensions adjusted to provide the optimum overlap with the pump and Stokes wavelengths.

It is apparent that there are several approaches to producing enhanced MIM structures. The lithography can be performed by conventional optical lithography (assuming a lithography tool with sufficient resolution), by interferometric lithography, or by nanoimprint lithography. Various optically transparent sticking layer materials including SiO$_2$, Si$_3$N$_4$, Al$_2$O$_3$, TiO$_2$, and HfO$_2$ among others, are available. Variations in process sequence will be evident to those skilled in the art. Different approaches will be readily apparent to those skilled in the art.

Yet still, in some embodiments in which the enhancement structure comprises MIM structures, one or more additional dielectric layers may be deposited around at least a periphery of one or more respective MIM structures. In particular, at least one of the MIM structures may include an additional dielectric layer (in addition to the dielectric adhesion layer) deposited around a periphery thereof, wherein the additional dielectric layer has a varying thickness. The additional dielectric layer may include at least a first thickness that is greater than a thickness of the underlying dielectric adhesion layer (in the event that the adhesion layer has a portion that is extending beyond the bottom surface of the MIM) and a second thickness that is less than a thickness of the underlying dielectric adhesion layer. For example, in one embodiment, the additional dielectric layer may include a profile that tapers from the first thickness to the second thickness, wherein the additional dielectric layer is deposited at an angle relative to the top surface of the substrate. Accordingly, the additional dielectric layer has a tilted orientation. Simulation testing shows that the tilted dielectric layer improved single molecule sensitivity and localized detection.

The enhancement is very sensitive to the thickness of the final SiO$_2$ deposition for the lift-off MIM structure. This is shown in FIGS. 26, 27, and 28, in which the enhancement is shown as the thickness of this layer is varied.

Figure 26:
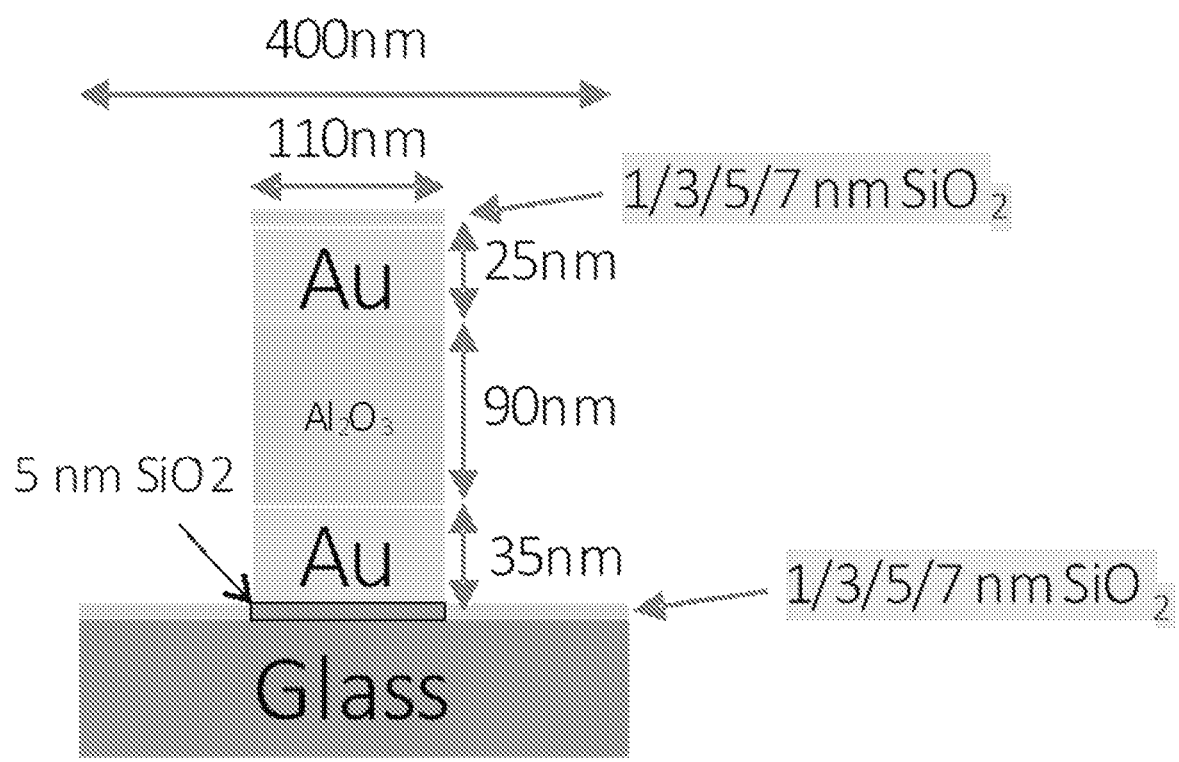
FIG. 26 is a side view, partly in section, of another embodiment of an enhancement structure comprising an additional dielectric layer, serving as the final layer, provided on at least the substrate and surrounding the MIM structure.

FIG. 26 is a side view, partly in section, of another embodiment of an enhancement structure comprising an additional dielectric layer, serving as the final layer, provided on at least the substrate and surrounding the MIM structure. In particular, a cross section of an MIM structure is shown, where the SiO$_2$ sticking layer is set at 5 nm and the additional final SiO$_2$ layer is varied from at 1-, 3-, 5-, and 7 nm. In each case, the polarization direction of the incident laser beam in in the plane of the figure.

Figure 27:
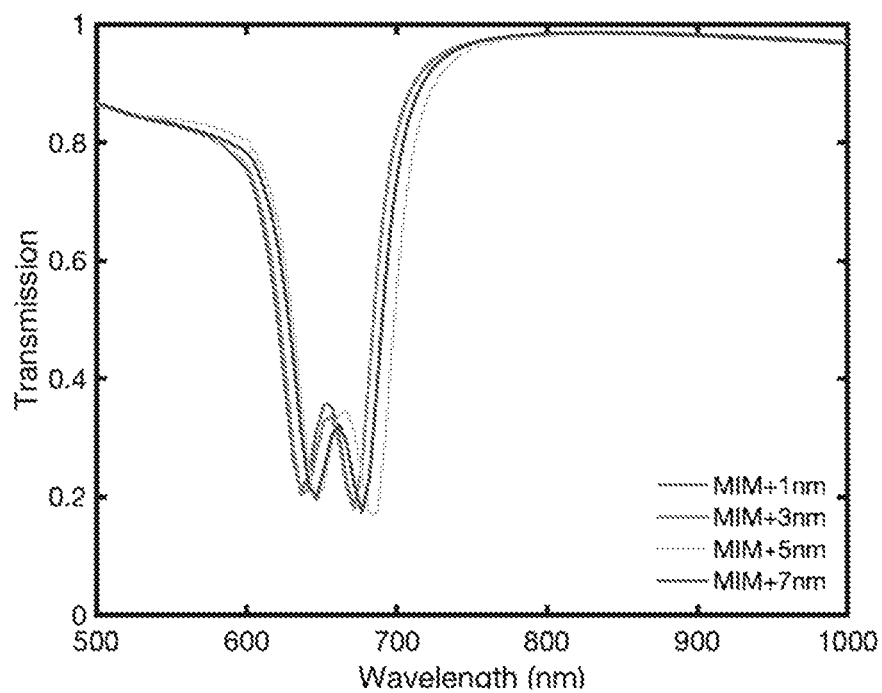
FIG. 27 is a line graph illustrating simulated transmission for different thicknesses of the final layer of the enhancement structure of FIG. 26.

FIG. 27 is a line graph illustrating simulated transmission for different thicknesses of the final layer of the enhancement structure of FIG. 26, showing that there are small changes in the resonance frequencies that can easily be compensated by dimensional changes.

Figure 28:
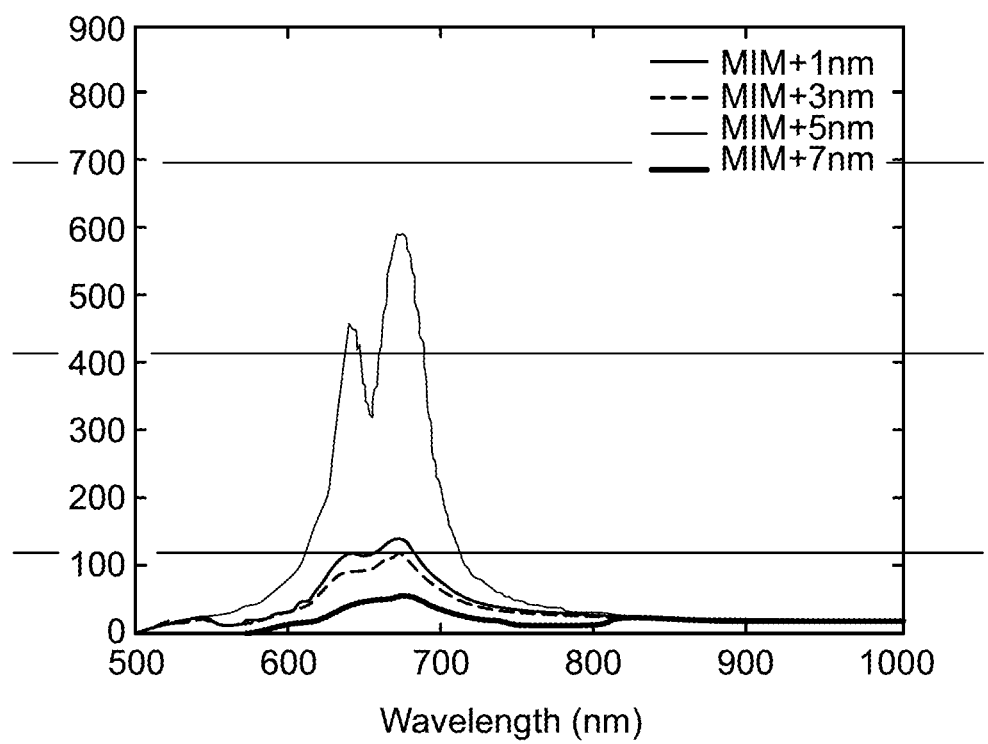
FIG. 28 is a line graph illustrating the corresponding peak enhancement factors vs. wavelength of each thickness of the final layer of the enhancement structure of FIG. 26.

FIG. 28 is a line graph illustrating the corresponding peak enhancement factors vs. wavelength of each thickness of the final layer of the enhancement structure of FIG. 26, showing the simulated enhancement factors (3 point smoothing). It should be noted that both the 3- and 7-nm simulations show a much weaker enhancement factor than the 5-nm simulation, but recall that the Raman signal scales as $\beta^2(\omega_P) \times \beta^2(\omega_S)$. It should be further noted that there is a dramatic increase in the enhancement factor when the final layer of SiO$_2$ just matches the thickness of the sticking layer (5 nm in this simulation).

Figure 29:
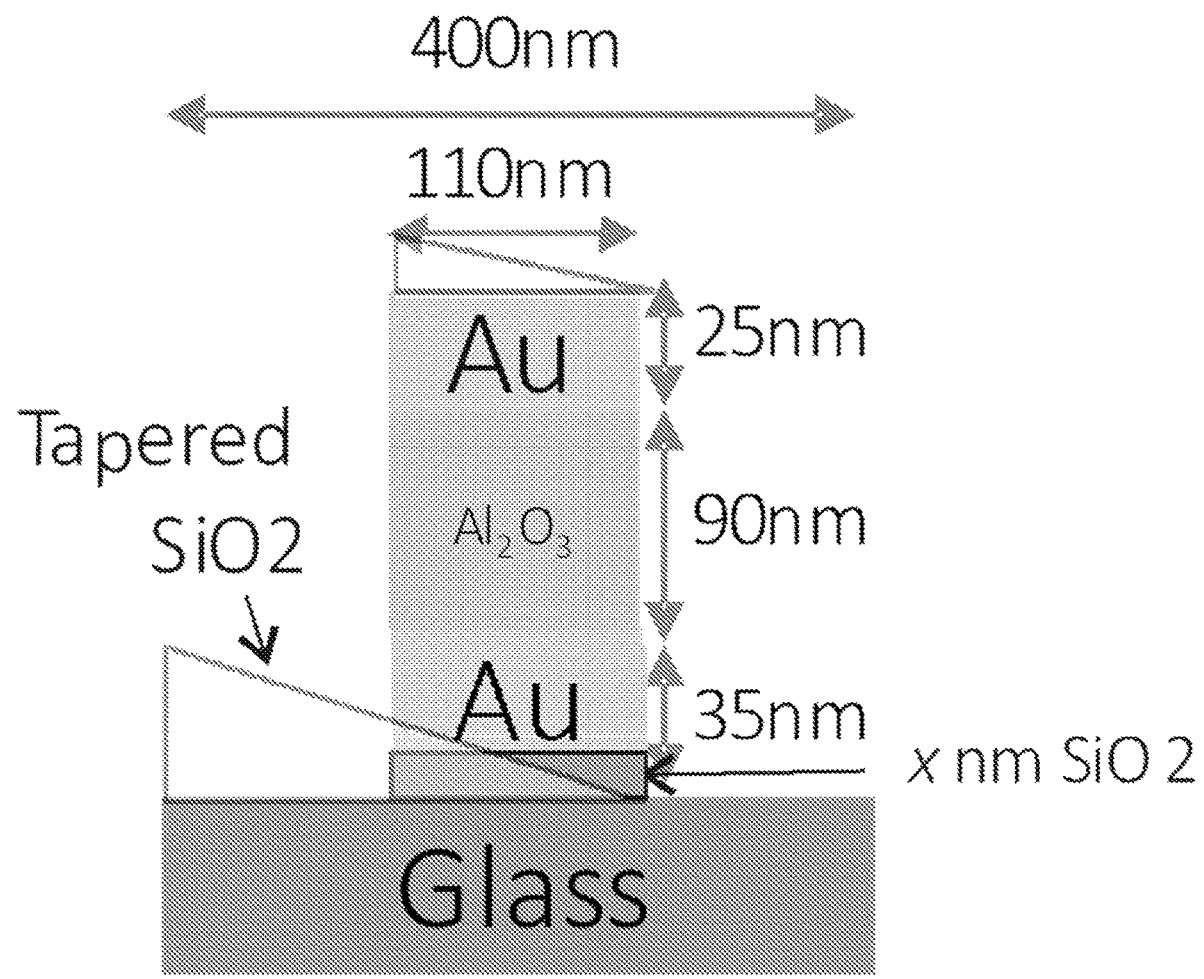
FIG. 29 is a side view, partly in section, of one embodiment of an enhancement structure consistent with the present disclosure including a MIM structure with an additional dielectric layer deposited on one or more portions thereof and having a tilted orientation.

This provides a mechanism for localizing the hot spot around the MIM structure by using an angled (shadow) deposition. FIG. 29 is a side view, partly in section, of one embodiment of an enhancement structure consistent with the present disclosure including a MIM structure with an additional dielectric layer deposited on one or more portions thereof and having a tilted orientation. As shown, the MIM structure with a sloped dielectric layer that crosses the level of the sticking layer. The dimensions are chosen for a pump wavelength of 633 nm and a Stokes or emission wavelength of 666 nm.

Figure 30:
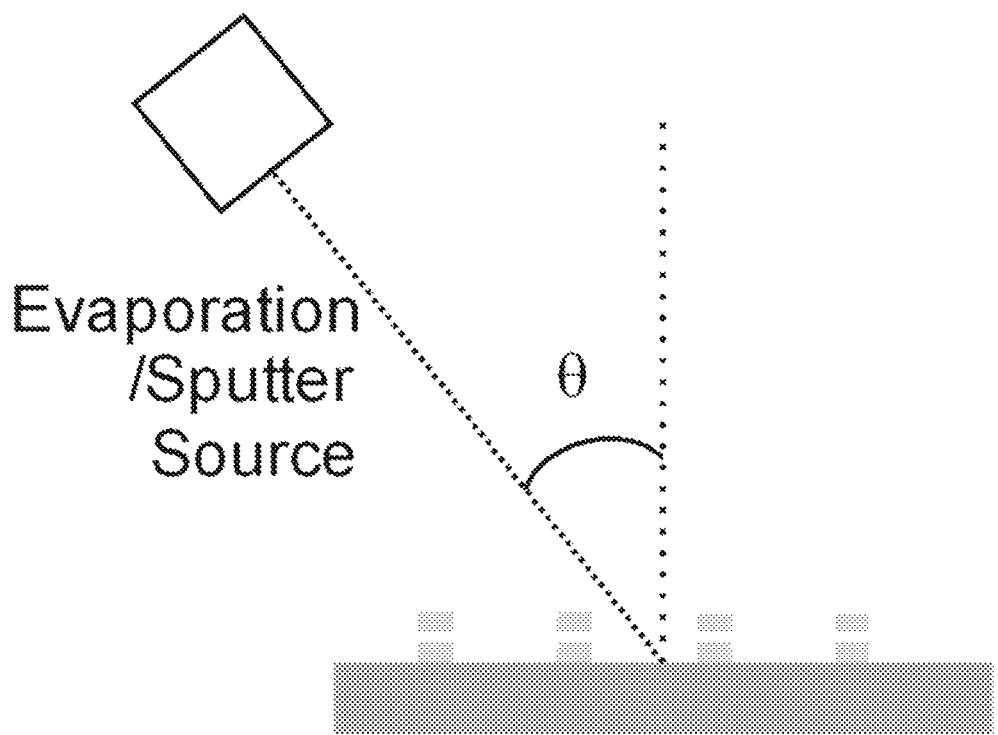
FIG. 30 shows a shadow evaporation/sputtering arrangement for use in fabrication of the titled or sloped layer(s) on the enhancement structure of FIG. 29.

FIG. 30 shows a shadow evaporation/sputtering arrangement for use in fabrication of the titled or sloped layer(s) on the enhancement structure of FIG. 29. Each post of a MIM structure blocks the evaporation behind the post, localizing the hot spot to the point along the circumference where the thickness of the tapered layer just matches the thickness of the sticking layer. Note that, since the refractive index of the sticking layer matches that of the glass substrate, a thicker layer than the ~5 nm layer that has been used to date can be used, easing the fabrication tolerances.

For the nanopore sequencing application, it is necessary to provide a mechanism to direct the long-chain molecule to pass through the electromagnetic hot-spot of the enhancement structure. Accordingly, embodiments of the present disclosure provide method for fabrication of an enhanced optical sensing platform. The method includes providing a substrate; defining a two-dimensional array of sticking-layer-metal-insulator-metal MIM structures atop the substrate; and depositing an additional layer of the same material as the sticking layer so that additional layer is thicker than the sticking layer at some positions around the periphery of the MIM and thinner than the sticking layer at other positions. The additional layer may be deposited at an angle to the surface of the substrate so that the MIM structures shadow the deposition resulting in an additional layer that is tilted relative to the substrate surface in the vicinity of each MIM structure.

Embodiments of the present disclosure further provide self-alignment of enhancement structure hot spot with a tortuous nanopore. In particular, there remains the problem that the tortuous nanopores are positioned randomly and are not registered to the enhancement structures. One possible solution is to block all of the pores except in a narrow anulus around each enhancement structure.

First Approach:

Rely on strain effects associated with the differential thermal expansion between Au and SiO$_2$ and on the compliance of the porous roof itself to shift the tortuous nanopores into the vicinity of the enhancement structures. Run structures through several thermal cycles to shift pores. It might be advantageous to use ellipsoidal MIM+ and to align the long axis of the ellipsoid along the direction of the nanochannel. There will be a larger strain gradient at the pointed end that will further encourage migration of the hot spot. This is a self-aligned approach that will provide the easiest solution.

Figure 31:
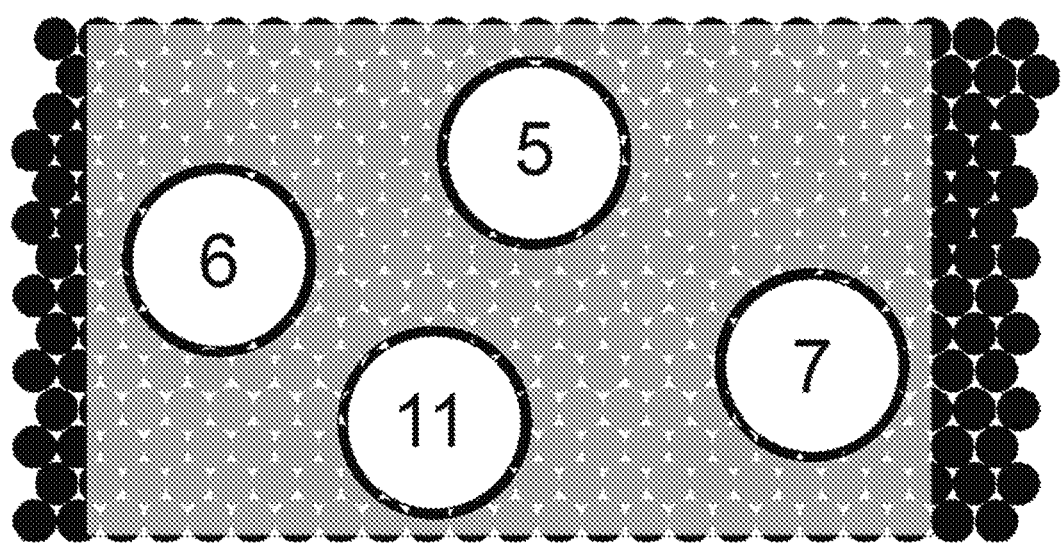
FIG. 31 is a top view of one embodiment of an enhancement structure in which tortuous nanopores of a nanochannel chip are registered with components of the enhanced structure, specifically showing random placement of metallic structures (illustrated as individual gold discs or pillars) and a dielectric film layer relative to tortuous nanopores formed by nanoparticles of a nanochannel chip, in which all pores are substantially blocked but form a narrow region of pores around the perimeter of each disc.

Second Approach:

FIG. 31 is a top view of one embodiment of an enhancement structure in which tortuous nanopores of a nanochannel chip are registered with components of the enhanced structure, specifically showing random placement of metallic structures (illustrated as individual gold discs or pillars) and a dielectric film layer relative to tortuous nanopores formed by nanoparticles of a nanochannel chip, in which all pores are substantially blocked but form a narrow region of pores around the perimeter of each disc. In particular, there are a number of possible nanopore sites within a ~10 nm annulus around each enhancement structure.

The method of fabrication may include:
1) Forming the nanochannels and nanopores by the usual process, IL, spin coating, sintering;
2) Depositing the layer structure for the enhancement, sticking layer, Au, insulator, Au; 3) Using negative resist and Cr lift-off to form a hard mask for etching the enhancement structures;
4) Etch to form enhancement structures aligned with the nanochannels;
5) Using ALD to coat the outsides of the enhancement structures with for example Al2O3 to a thickness of <~10 nm;
6) Deposit $Si_3N_4$ to seal the holes in the roof outside of the ALD protected annulus; and
7) Selectively remove the $Al_2O_3$ with a Cl based etch and remove the hard mask with a metal remover.

Figure 32:
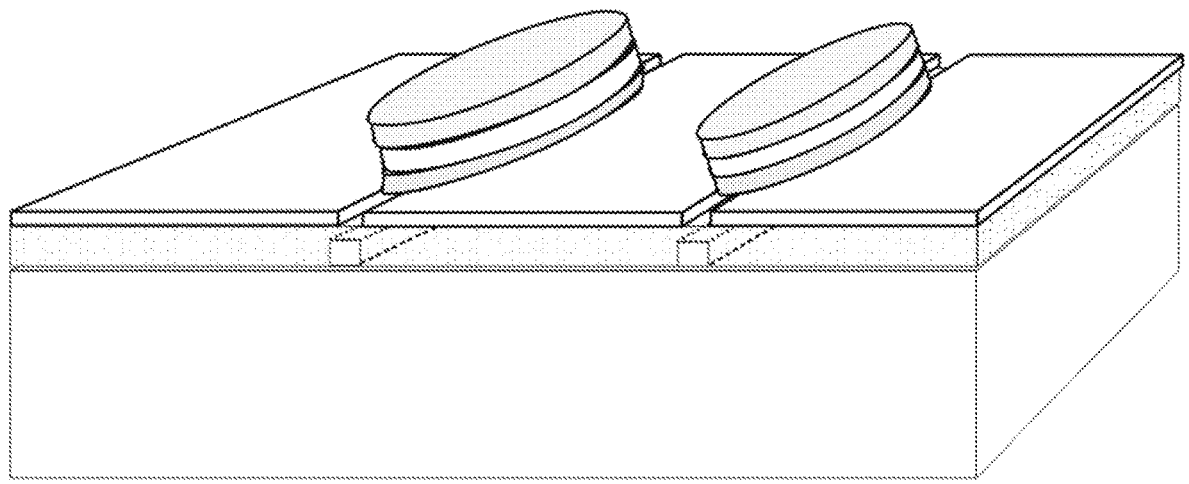
FIG. 32 is a perspective view of another embodiment of an enhancement structure is selectively placed just above and along nanochannels of nanochannel chip, in which a hot spot of each MIM structure is aligned with tortuous nanopores.

Third Approach:

FIG. 32 is a perspective view of another embodiment of an enhancement structure is selectively placed just above and along nanochannels of nanochannel chip, in which a hot spot of each MIM structure is aligned with tortuous nanopores.

In one embodiment, the MIM structure is separated from the roof of the nanochannel with a small gap. There is some advantage to using ellipsoidal MIM structures aligned along the nanochannels. Circular cross section MIM could also be used.

The method of fabrication may include:
1) Fabricate nanochannels and nanopores as usual;
2) Deposit a $Si_3N_4$ blanket blocking layer; and
3) Use negative resist (separated from the nanopores by the $Si_3N_4$ layer) to define slits along the nanochannels. This can be aligned using the existing index contrast;
4) Etch away the nitride layer over the nanochannels and deposit amorphous Si;
5) Deposit new photoresist layer to define MIM; deposit MIM and liftoff; and
6) Use $XeF_2$ to remove Si over each nanochannel. This is a chemically selective isotropic process.

Figure 33:
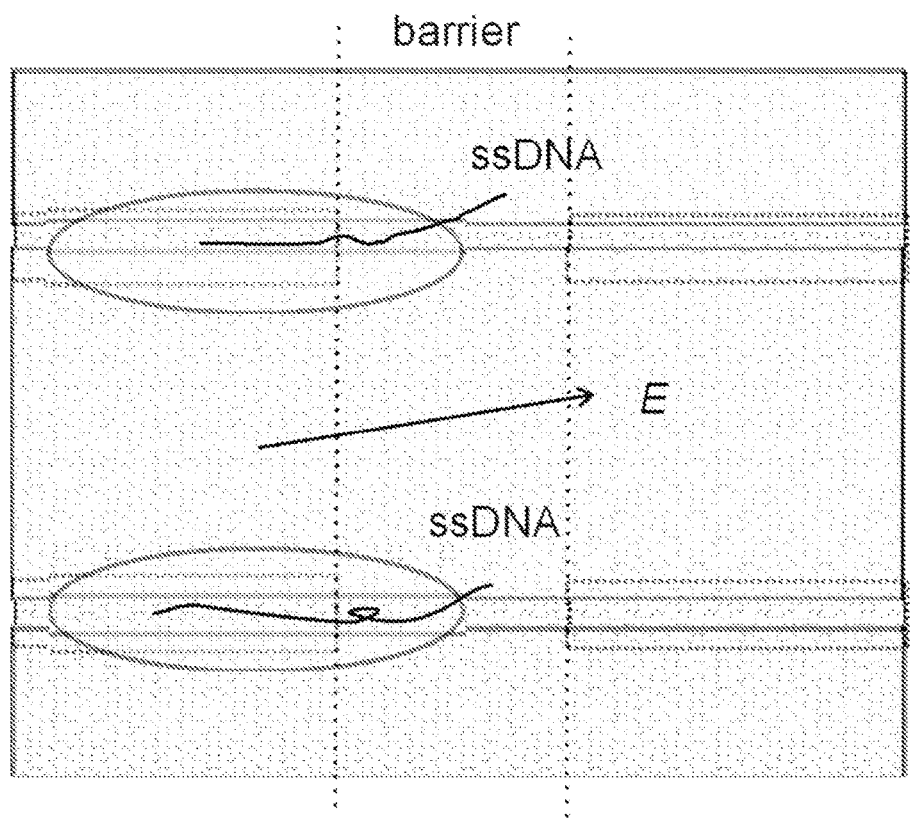
FIG. 33 illustrates a DNA sequencing embodiment of the enhancement structure of FIG. 32, in which an electric field is applied at an angle to the nanochannel axis to thereby force a DNA sample through the nanochannel and toward a corner portion of the associated MIM structure where the enhancement is the greatest.

FIG. 33 illustrates a DNA sequencing embodiment of the enhancement structure of FIG. 32, in which an electric field is applied at an angle to the nanochannel axis to thereby force a DNA sample through the nanochannel and toward a corner portion of the associated MIM structure where the enhancement is the greatest.

In some embodiments, the disclosure provides a method for aligning enhancement structures and tortuous nanopores in the roof of a nanochannel formed from an assembly of sintered nanoparticles in which the method includes cycling thermal conditions after formation of the structure to create nanopores aligned with the edges of the enhancement structures.

Embodiments of the disclosure provide a method for aligning enhancement structures and tortuous nanopores in the roof of a nanochannel formed from an assembly of sintered nanoparticles. The method includes sealing the roof of the nanochannels except in a thin annulus around each enhancement structure. The width of the annulus may be about 1-10 nm. In some embodiments, fabrication of the annulus comprises or consists of: fabricating nanochannels with roofs containing tortuous nanopores; deposit blanket films of the materials and the thicknesses to form the enhancement structure (e.g., which may also seal the roof so photoresist can be applied without filling the nanochannels); defining, with a negative photoresist, an array of apertures and metal lift-off to form a hard mask; etch to form the enhancement structures; use atomic layer deposition to coat the top and sides of the enhancement structures with a sacrificial layer; use a directional etch to remove the sacrificial layer on the top of the enhancement structures and in the spaces between enhancement structures, leaving the sidewall coating of the enhancement structures; deposit a layer of material to seal the nanopores that are not covered by the enhancement structures; selectively remove the sacrificial material from the sidewalls of the enhancement structures; selectively remove the metal mask from the tops of the enhancement structures. In disclosed methods, the metal may be, for example, Cr or Ni.

In another embodiment, the method includes fabricating nanochannels with roofs containing tortuous nanopores as per existing technology; deposit a blanket layer of a first thin-film material to seal all of the tortuous nanopores in the roof; pattern an ARC/negative photoresist layer to allow access to stripes of the first thin-film material over each nanochannel; etch away the first thin-film material in the accessed regions; deposit amorphous silicon to planarize the surface and remove the remaining ARC/photoresist; fabricate enhancement structures over the planarized layer; and selectively remove the amorphous silicon using a $XeF2$ etch. Preferably the first thin-film material is silicon nitride or silicon oxynitride. The enhancement structure may be a metal-insulator-metal structure with dimensions chosen to provide resonances in the vicinity of the pump and Stokes frequencies for Raman scattering from target molecular constituents.

The disclosure provides for integrating a porous layer, a tortuous nanopore, and machined pore and enhancement structures. U.S. Pat. No. 7,825,036 shows fabrication with a porous roof and multilayer structures, and is incorporated by reference. U.S. Pat. No. 8,404,123 shows methods of separating components of a fluid between two nanochannels, and is incorporated by reference. U.S. Pat. No. 9,156,004 shows separating components of a fluid between two nanochannels, on using CVD and ALD to affect transport between two nanochannels and is incorporated by reference. U.S. Pat. No. 9,927,397 shows a sequencing approach with a porous membrane and is incorporated by reference. U.S. Pat. No. 10,060,904 shows control speed of translocation from roof the nanochannel, using electric field to control translocation, long chain molecules incl. DNA) and is incorporated by reference. U.S. Pat. No. 10,184,930 show sequencing without a mesoporous silica layer and is incorporated by reference. U.S. Pat. No. 10,969,364 shows sequencing with mesoporous silica layer and is incorporated by reference. U.S. Pat. No. 10,976,299 shows a device with DNA between two nanochannels and is incorporated by reference.

Prior art has not shown speed of translocation of long chain molecules between two macro-scale chambers as opposed to two nanochannels. At best, prior art has addressed measuring current blockage of DNA through a pore between two chambers.

In some applications the nanochannels are not necessary, rather the porous silica beads can be used to slow DNA transport between sealed chambers, one used as a reservoir and the second as an active chamber that can add single moieties to the chain. An example application is using DNA as a storage material. Each strand is used to preserve digital memory in the sequence of moieties, which are not restricted to the four naturally occurring bases. One chamber is used to add a base at a time to the DNA (the write operation). The two chambers are separated by a nanopore that provides the read operation. During storage of the information the DNA is kept stable in the reservoir chamber. During a read operation the DNA is translocated through the nanopore from the reservoir to the active chamber and sequenced during the translocation. In a write operation an enzyme is added to the active chamber to add a specific moiety to the DNA long chain molecule. After adding a single specified moiety, the DNA is translocated back to the storage chamber.

As will be apparent to those skilled-in-the-art of electronics fabrication, there are often several approaches and process sequences that can the used to reach the same final result. A particular embodiment is described herein; alternatives that are within the common usage are included by reference.

The aim is to fabricate a parallel array of two chamber units (referred to as the storage and active chambers) separated by a nanopore and incorporating an enhancement structure for Raman optical readout.

Figure 34A:
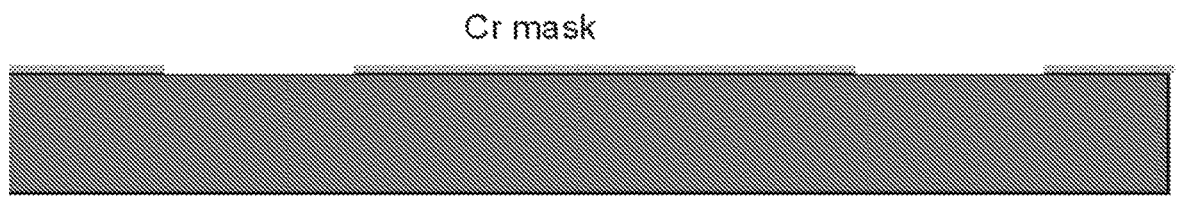
FIGS. 34A-34J illustrate various steps in fabricating a parallel array of two chamber units (referred to as storage and active chambers) separated by a nanopore and incorporating an enhancement structure of the present invention for Raman optical readout.
Figure 34B:
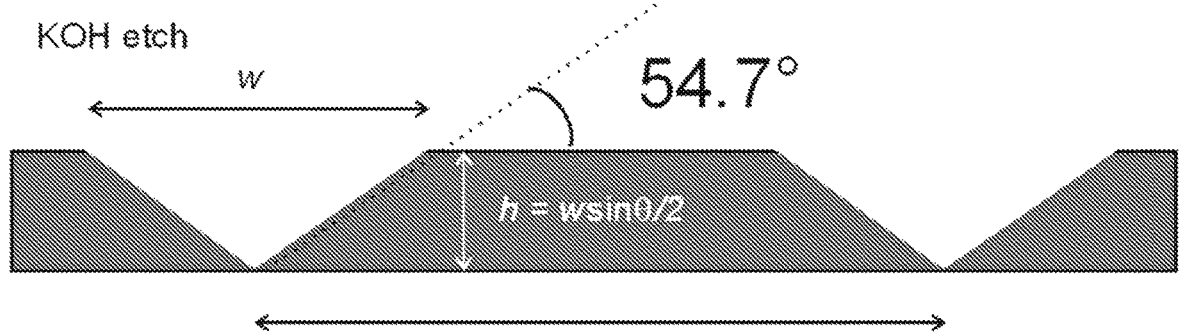
Figure 34C:
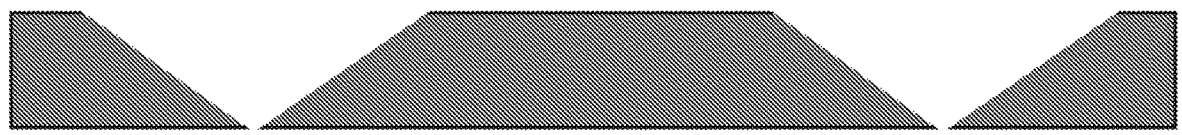
Figure 34D:
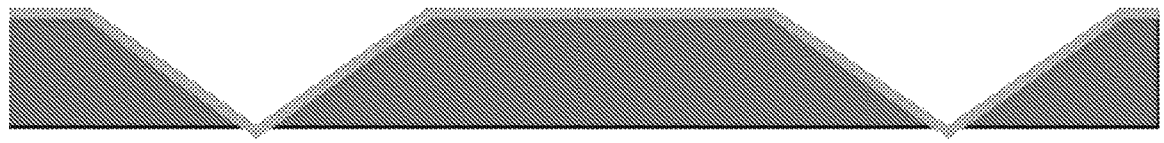
Figure 34E:
Figure 34F:
Figure 34G:
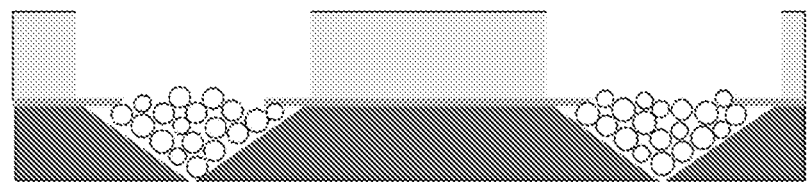
Figure 34H:
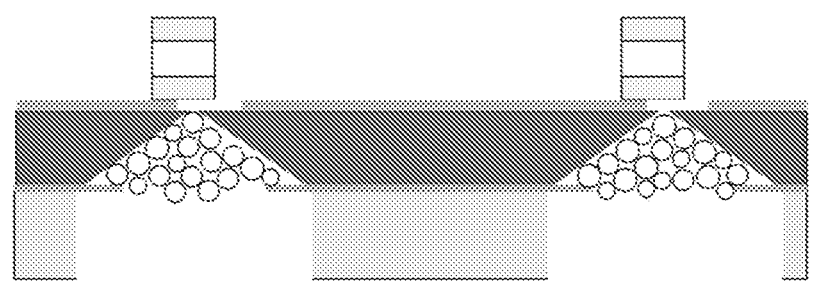
Figure 34I:
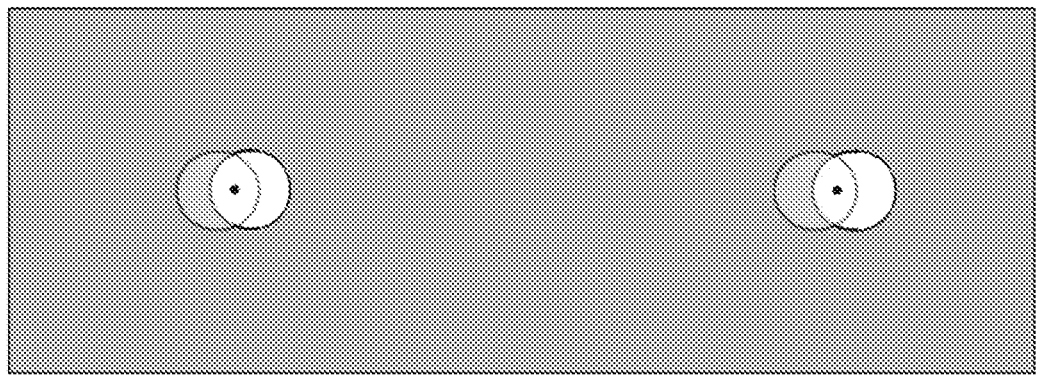

FIGS. 34A-34J illustrate various steps in fabricating a parallel array of two chamber units (referred to as storage and active chambers) separated by a nanopore and incorporating an enhancement structure of the present invention for Raman optical readout. FIG. 34A is a side view, partly in section, showing a chromium (Cr) mask with holes to define pattern. FIG. 34B shows inverted pyramids that result from KOH etching. FIG. 34C shows further etching to form nanopores at the bottom of the inverted pyramids. FIG. 34D shows coating with a thin sacrificial resist layer. FIG. 34E shows silica nanoparticles are spun into the inverted pyramids. FIG. 34F shows the wafer is sintered (~800° in air/oxygen ambient) to remove the resist and sinter the nanoparticles for stability. FIG. 34G shows a thin film is added to trap the nanoparticles if necessary and the storage chambers are defined. FIG. 34H shows handle wafer is added. FIG. 34I is a top view showing the spatial relationship between the sticking layer (i.e., dielectric adhesion layer), the open area, and the enhancement structure.

The method of fabrication starts with a thin crystal silicon layer typically oriented in a <001> direction. For ease of handling this is usually affixed to a handle layer, for example a silicon-on-insulator (SOI) wafer. Pattern a periodic array of pillars in a photoresist layer, deposit a hard mask, for example Cr, and remove the photoresist. Only one dimension is shown in the figures.

FIG. 34A shows the result of this step. Depending on the optical arrangement used for readout, the array can be periodic in either one or two dimensions.

Use KOH etching to form inverted pyramids in the Si with {111} facets. This is a well-known process that relies on the differential etch rates of various facets of Si with the {111} facets having the slowest etch rates. Even though the holes in the Cr are circular, the resulting structures will be rectangular as a result of the Cr etch stop.

FIG. 34B shows that the facets are at θ=54.7° to the <001> facet. Thus the depth of the etch h is related to the top aperture in the silicon w by h=w sin(θ)/2. With continued etching the etch depth becomes h'=p sin(tθ)/2 where p is the pattern period. The depth is controlled by the KOH solution concentration, temperature and etch duration. Real-time monitoring by optical reflection/transmission can be implemented as necessary to ensure repeatable results.

In the example of FIG. 34B, the etch process is stopped shortly before the inverted pyramid breaks through the bottom of the silicon layer.

FIG. 34C shows a directional etch process such as RIE is performed to break through the bottom of the Si layer and form nanopores. If these are intended for current readout, the uniformity of the nanopore size is important. For the optical readout envisioned herein, the tolerance is significantly relaxed since the nanopores control neither the translocation speed through the nanopore, nor the current flow used as a readout mechanism. This will be discussed in detail below.

FIG. 34D shows application of a thin resist layer is applied; this is a sacrificial layer that will be removed subsequently.

FIG. 34E shows the result of spin coating the sample of with silica nanoparticles with a nominal diameter of 50 nm and a size dispersion of ~±20% (represented in the figure by three different size particles). These particles form tortuous nanopores (convoluted pathways with multiple contact points to the DNA) that are used to slow the DNA translocation. FIG. 34E shows silica nanoparticles are spun into the inverted pyramids.

FIG. 34F shows the structure after sintering the wafer from FIG. 34E at ~800° in an oxygen ambient. The resist layer is burned away and the particles are sintered together to provide mechanical stability. FIG. 34F shows the wafer is sintered (~800° in air/oxygen ambient) to remove the resist and sinter the nanoparticles for stability.

In FIG. 34G a thin film has been added to trap the particles in the inverted pyramids and the storage chambers have been defined. The thin film could be, for example, a mesoporous silica film that completely covers the surface of the substrate. FIG. 34G shows a thin film is added to trap the nanoparticles if necessary and the storage chambers are defined.

In FIG. 34H the wafer is inverted so that processing occurs on what was previously the bottom surface of the wafer. If SOI is used, this involves attaching a handle wafer and removing the bottom oxide layer of the SOI. A thin film (blue) is deposited and patterned with ~100 nm diameter apertures. In one embodiment, this film is Si$_3$N$_4$.

FIG. 34H shows handle wafer is added and the fabrication is shifted to the opposite side of the Si. A thin sticking layer is added and patterned to ensure the nanopore at the bottom of the inverted pyramids is open. A sacrificial layer is added to provide a flat surface for processing and the enhancement structures (shown as MIM) are added, offset in the opposite direction.

The apertures are offset with respect to the nanopores at the top of the silicon, shown as black dots in the top view of FIG. 34I. FIG. 34I is a top view showing the spatial relationship between the sticking layer, the open area and the enhancement structure. j) Conceptual cartoon showing the operation. The DNA is represented by the red filaments. DNA is drawn into the active (top) chamber with an applied electric field; emerges under the enhancement structure and passes the Raman hot spot at the bottom of the enhancement structure, providing an opportunity for sequencing. Optionally, biochemistry can be carried out to add a moiety to the end of the DNA strand. The voltage is switched and the DNA can be read again as it passes back into the storage chamber.

Similar to the process sequence above, the apertures are filed with a sacrificial layer that can be selectively removed. Then enhancement structures are deposited, shown as MIM structures. The MIM structures are offset in a different direction from the nanopores at the bottom of the inverted pyramids and the sacrificial layer is removed.

Figure 34J:
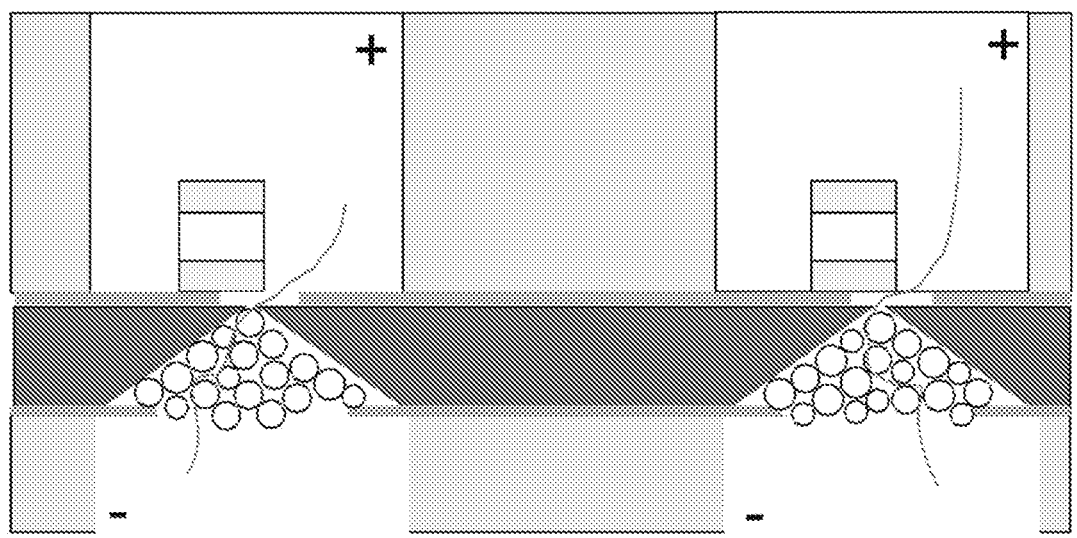

FIG. 34J shows the operation. The DNA is represented by the filaments. A bias is applied between the two chambers to draw the DNA from the storage chamber to the active chamber. The translocation speed is set by the transit through the tortuous nanopores formed by the silica particles, and in independent of the size of the nanopore at the bottom of the inverted pyramid. The DNA enters the active chamber under the enhancement structure and threads past the enhancement structure where it is sequences by Raman scattering as it passes the enhancement structure. In a write operation appropriate biochemistry is performed to add a specific moiety to the DNA strand and the voltage is reversed and the DNA is pulled back into the storage chamber.

It is emphasized that all of the fabrication described is readily available in several generation old semiconductor fabrication. There is no requirement for e-beam or ion-beam lithography, and all of the nanoscale dimensions are achieved with self-alignment processes.

Figure 35:
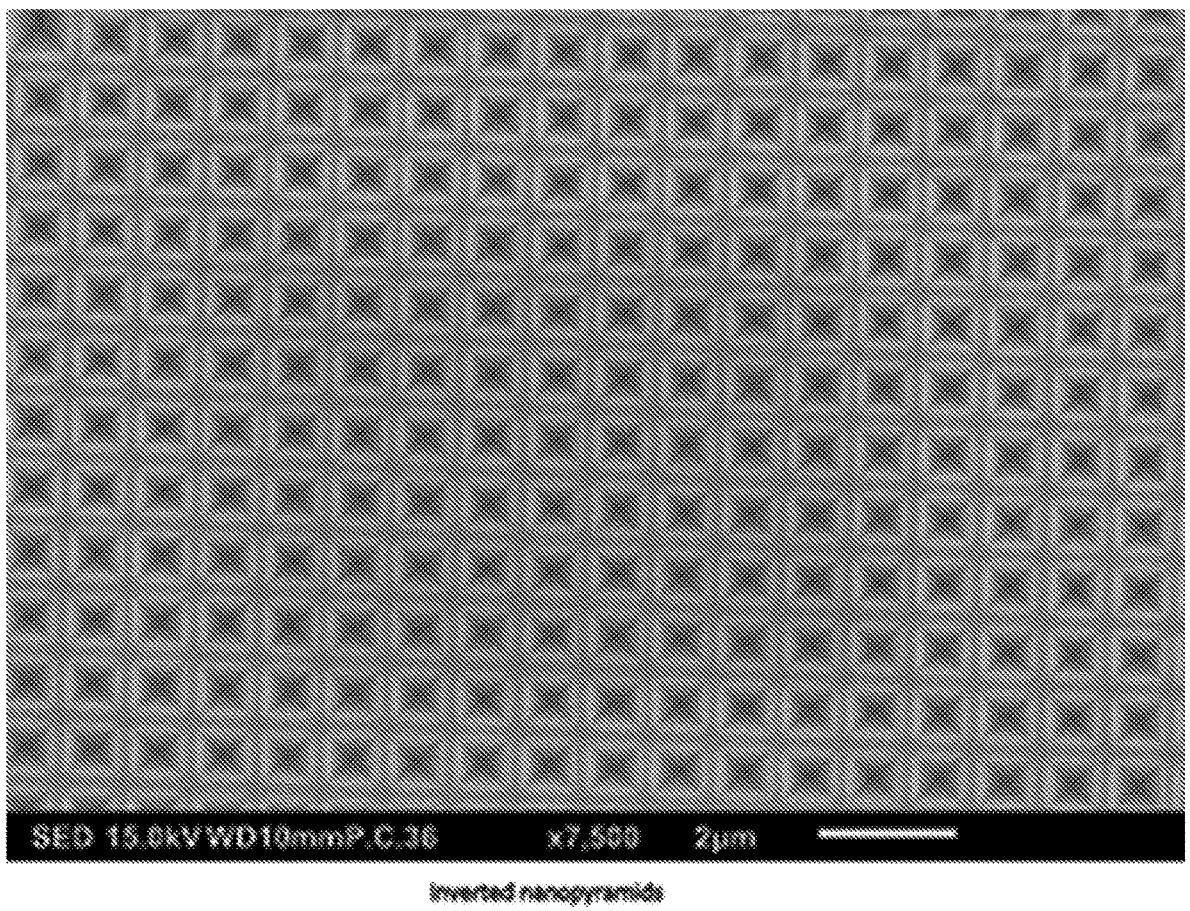
FIG. 35 shows an exemplary fabricated sample of the device formed from the fabrication steps of 34A-34I.

FIG. 35 shows a fabricated sample. The period was 800 nm. This was a thick Si wafer, so the pyramids are not close to reaching the bottom surface of the Si. Interferometric lithography using a 355 nm (third harmonic of a YAG laser) was used to define the pattern. As shown, inverted nanopyramids formed in a silicon substrate using interferometric lithography and KOH etching.

As shown at least in FIGS. 34A 34J, embodiments of the disclosure provide a method for fabricating storage and active chambers for DNA operations. The method includes: providing a faceted Si crystal with a thickness; depositing and a hard mask and patterning the mask with an array of holes with a diameter w and a period p; wet etching with a KOH solution to form inverted faceted pyramids in the Si crystal, wherein the etch parameters and the Si crystal thickness are chosen so that the depth of the inverted pyramids below the original Si crystal surface is slightly less than the thickness; complete etch through Si crystal layer to form array of nanopores; coat surface with a thin resist layer; deposit silica nanoparticles with a mean diameter d and a size dispersion s by spin coating to fill the inverted faceted pyramids; thermally sinter the nanoparticles together and burn out the resist in an oxygen containing ambient; optionally, add a thin film layer to trap the nanoparticles in the inverted faceted pyramids; fabricate walls of the storage chambers using conventional fabrication processes;

prepare second side of the faceted Si crystal for processing; deposit a sticking layer on the second side of the faceted Si crystal; pattern the sticking layer with a sacrificial material that covers the array of nanopores; deposit and pattern an array of enhancement structures, one per nanopore, arranged so that the enhancement structure extends partially over the sticking layer and partially over the sacrificial layer said portion to include the position of the nanopore in the faceted Si crystal; remove the sacrificial layer to expose the nanopore; fabricate the walls of the active chamber and provide individually addressable electrical contact means in both the storage and active chambers.

Embodiments of the disclosure provide a device for DNA manipulation, the device comprising: an array of storage chambers and an array of active chambers on opposite sides of a thin Si crystal membrane; an array of nanopores between opposing storage and active chambers; an ensemble of silica nanoparticles adjacent to the nanopores to slow the DNA translocation between the opposed storage and active chambers; an array of electromagnetic enhancement structures partially suspended over the array of nanopores; electrical means for applying an individually addressable voltage between opposing storage and active chambers; biochemical means for adding moieties to the DNA strand in the active chamber; optical means for detecting Raman scattering signatures of individual moieties on the DNA strand in each chamber as the DNA translocates past the electromagnetic enhancement structure.

DNA Data Storage Using Surface-Enhanced Fluorescence

It should be noted that, in addition to enhancing the Raman signal, the enhancement structures of the present invention also affect other physical phenomena that respond to excitation EM fields, and this includes fluorescence. In fact, the fluorescent signal is dramatically easier to observe, although in general use the signal from an attached fluorophore does not provide the kind of molecular level information that is so powerful for Raman techniques. Nevertheless the ability to probe fluorescent molecules using SERS and enhancement structures consistent with the present disclosure can provide significant benefit in certain applications.

Figure 36:
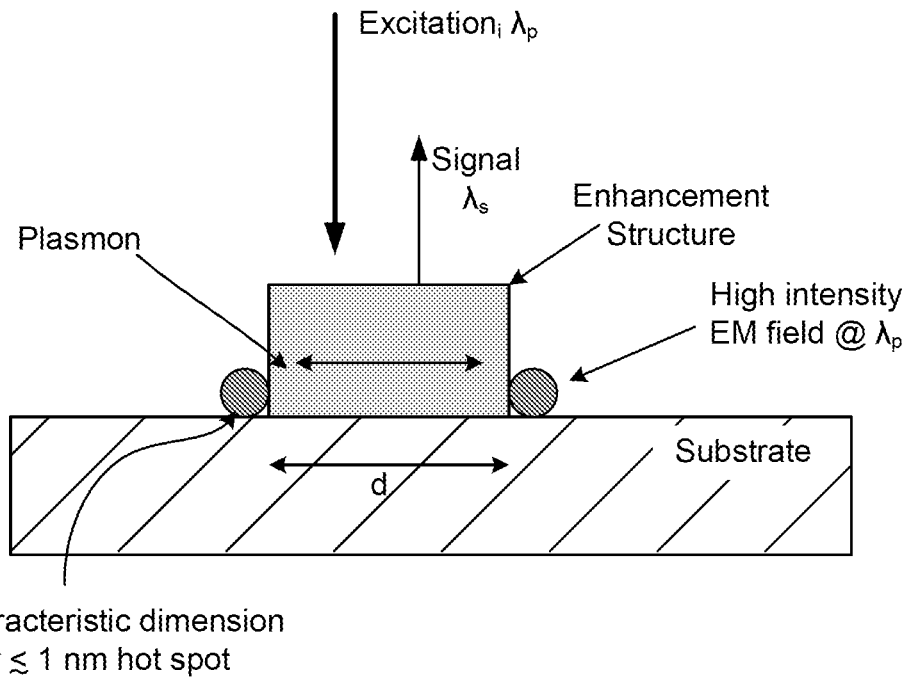
FIGS. 36 and 37 are side and top views of an embodiment of an enhancement structure of the present invention illustrating a metallic structure (illustrated as a single gold disc or pillar) and the associated hot spots, including "hot spot" zones that are relatively small in the Z and r dimensions, but are larger in the θ dimension.

One notable advantage is that enhancement structures can provide exceptionally small spatial resolution, down to a single molecule, such as the exemplary fabricated sample of the device formed from the fabrication steps of 34A-34I, as illustrated in FIG. 36. This is advantageous in the case of identifying each single molecule that make up an ensemble of molecules, for example a linear chain of molecules, for example in the case of nucleic acid chains, for example DNA.

In the case of DNA data storage, for example, small spatial resolution provided by enhancement structures of the present invention facilitates the ability to maximize the data density stored in DNA molecules, or other molecules suitable for data storage. Having single or few molecule resolution could also be advantageous to reduce the computational burden of identifying single unknown molecules from a collection of signals from multiple molecules.

Small spatial resolution can also provide the optimal excitation exposure for observing a single or very few molecules so that sufficient signal is collected for detection and identification, and over-exposure and bleaching of the target molecule can be avoided in the case of larger spot sizes without the use of enhancement structures. This may be particularly true if a target sample is a linear chain of molecules with fluorescent labels, and the linear molecule, for example DNA, transits an excitation zone, the excitation zone being approximately the size of a single molecule or a few molecules (as will be described with regard to FIG. 38), and thus transits at a rate to provide a detectable signal suitable for identifying the molecule, and then leaves the excitation zone so as to minimize the integrated amount of energy and peak power that the identified molecule has experienced.

Figure 37:
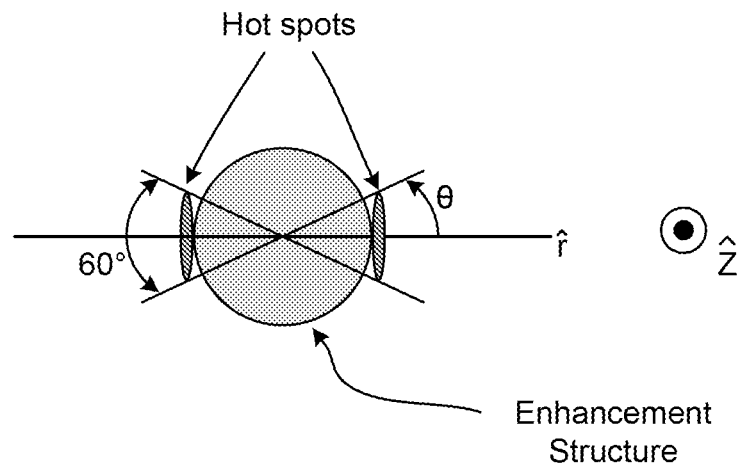

FIGS. 36 and 37 are side and top views of an embodiment of an enhancement structure of the present invention illustrating a metallic structure (illustrated as a single gold disc or pillar) and the associated hot spots, including "hot spot" zones that are relatively small in the z and r dimensions, but are larger in the θ dimension. The design of enhancement structures generally leads to asymmetric enhancement zones, and the design can be changed and optimized to tailor the shape and extent of the enhancement zone for use to an application (see FIGS. 36 and 37).

Figure 38:
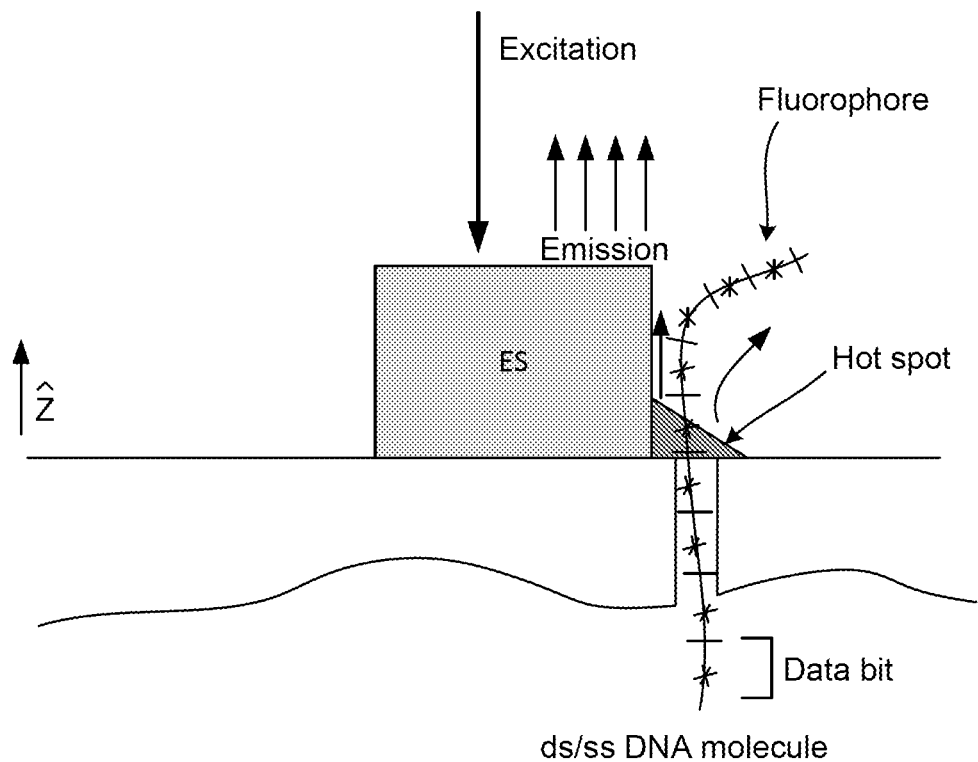
FIGS. 38, 39, and 40 are side (FIGS. 38 and 40) and top (FIG. 39) views of an enhancement structure and a moving probed linear chain of molecules with one or more fluorescent labels, in which the linear molecule (e.g. DNA) transits an excitation zone associated with a hot spot of the enhancement structure, the excitation zone being approximately the size of a single molecule or a few molecules, thereby allowing for DNA data storage capabilities.
Figure 39:
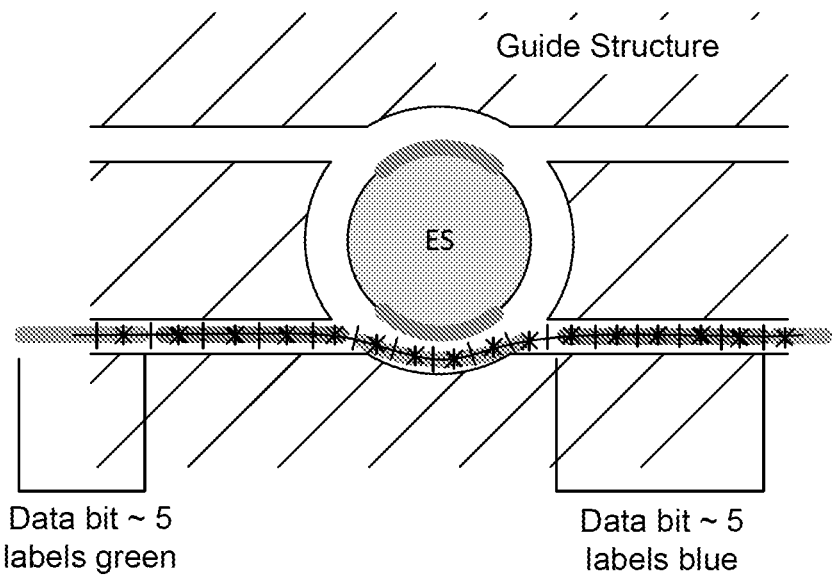
Figure 40:
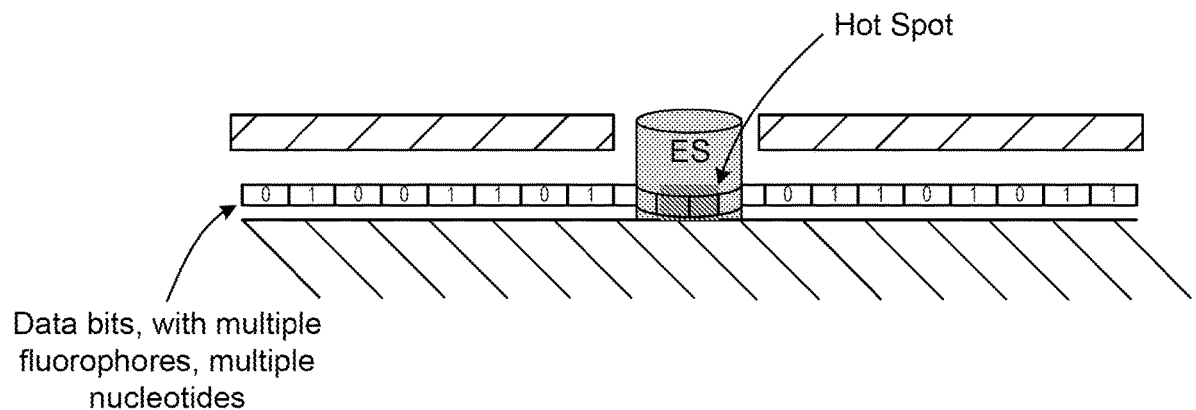

FIGS. 38, 39, and 40 are side (FIGS. 38 and 40) and top (FIG. 39) views of an enhancement structure and a moving probed linear chain of molecules with one or more fluorescent labels, in which the linear molecule (e.g. DNA) transits an excitation zone associated with a hot spot of the enhancement structure, the excitation zone being approximately the size of a single molecule or a few molecules, thereby allowing for DNA data storage capabilities.

In the case of a cylindrically shaped enhancement structure and linear polarized excitation, the hot spot is symmetrically generated at +/−180 deg in θ (see FIG. 37). The angular extent in q can be controlled to some extent with elliptical, rather than circular, structures.

If sufficient signal or data rate can be collected via a single molecule resident in a linear chain like DNA, the transiting through a minimal hot spot dimension, for example in the z dimension, might be employed.

If signal levels are low for a given system or target molecule, and it is desired to collect signal from multiple molecules, or if low data rates are desired, then transiting the hot spot through the θ direction might be desirable (see FIG. 39). This might be the case for example if each data bit is composed of 10, or 50, or 100 nucleotides labeled with fluorophore, and the excitation, hot spot size and enhancement, molecule transit time, exposure energy and peak power, are mutually individually optimized to provide system requirements for DNA data storage.

As previously described herein, techniques have been developed to narrow this angular distribution. Specifically, by varying the thickness of the final $SiO_2$ layer of the MIM structure so that it matches the thickness of the sticking layer only for a narrow angular range and setting the polarization of the pump laser beam to excite the plasma wave just in this position.

For the enhancement of fluorescent signals of linear molecules, in some way labeled with a fluorophore in order to optimize the encoding of data into a DNA molecule, other signal levels might be available or data collection rates might be desired. In this case the optimization of the structures that guide the test molecule containing the data regions of interest, for example a molecule of DNA coded in some way with fluorophores to encode desired data for DNA data storage, as well as the enhancement structure for generating the signal from the encoded data, can be designed in order to optimize the interaction with a hot spot to provide sufficient signal, data rate, longevity, and other key systems requirements.

Figure 41A:
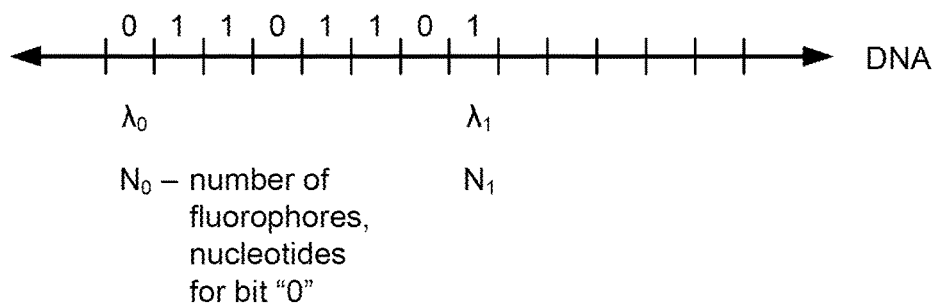
FIGS. 41A and 41B illustrate an alternative embodiment of formatting DNA data blocks in a linear DNA molecule.
Figure 41B:
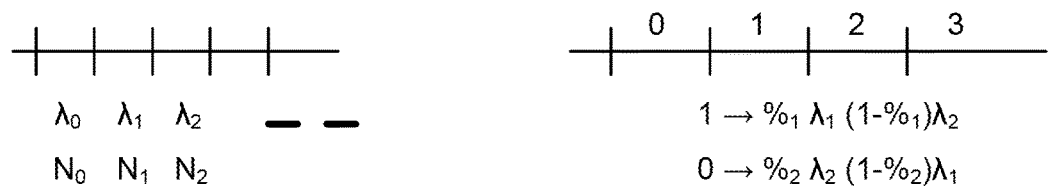

The enhancement factor response of individual enhancement structures are typically wavelength dependent, and can be tailored through design using the underlying physics of the plasmonic excitation the causes the enhancement phenomena. Thus an enhancement structure can be optimized at both the excitation wavelength and emission wavelength, or for multiple excitation and emission wavelengths. This may be advantageous if for example the data is encoded in multiple emission colors (see FIG. 41A), to facilitate more bits per single data block feature. This might include different emission wavelength (color) labels on single molecules, or on multiple molecules, or mixtures of colors on each single data block (see FIG. 41B).

Raman signatures are typically narrow lines corresponding to molecular vibrations/rotations. A typical linewidth is 1- to 5-$cm^{-1}$, determined by the vibrational dephasing time. In contrast, fluorescence linewidths are much broader, 10s to 100s of $cm^{-1}$ due to the broad range of electronic/vibrational levels that contribute to the fluorescence and the much shorter radiative lifetime. This makes tuning of the Stokes (lower energy than the pump photon) less critical in surface-enhanced fluorescence.

With regard to the structure that does not require precise alignment between the hot spot and the nanopore, specifically shown in FIGS. 32 and 33, the idea is to place the MIM structure above the nanopore (only defined to ~ the 100 nm diameter of the MIM), to leave a groove under the nanopore and to extract the DNA with an applied electric field forcing it past the hot spot.

For a data storage application each "bit" could correspond to ~100 fluorophores which would relax the translocation speed requirement by a similar factor. Coupled with the vastly higher fluorescence efficiency, this would make high speed readout a realistic possibility. This could be done with a simple dispersive system and a 1D detector array that can be read out at high speeds. An alternative is to use a set of color filters and a set of single, large area detectors that can operate at MHz or higher speeds.

Figure 43:
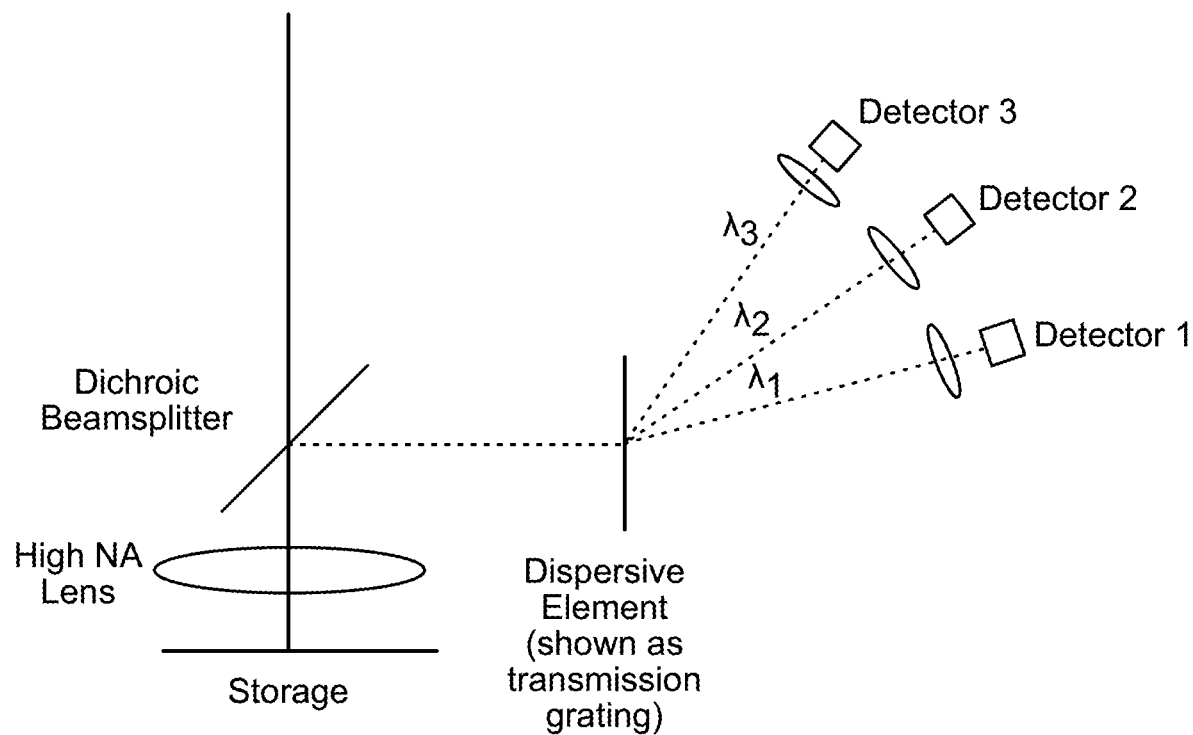
FIG. 43 is a schematic illustrating an optical readout system for use in digital DNA data storage applications, the system including a dispersive element (grating or prism depending on the specific fluorophores), a detector array, a set of dielectric filters to restrict the wavelength range seen by each detector (and minimize crosstalk and scattering), and a lens system to collect the fluorescence.

FIG. 43 is a schematic illustrating an optical readout system for use in digital DNA data storage applications, the system including a dispersive element (grating or prism depending on the specific fluorophores), a detector array, a set of dielectric filters to restrict the wavelength range seen by each detector (and minimize crosstalk and scattering), and a lens system to collect the fluorescence.

It should be noted that the minimization of exposure to a fluorophore label of interest is desired generally in order to avoid photobleaching of the fluorescent label, and thus facilitates the number of times a molecule may be identified or "read". This is particularly advantageous in the case the sample stability is desired, for example in the case of DNA data storage, where multiple reads over an extended time period may be advantageous.

Figure 42:
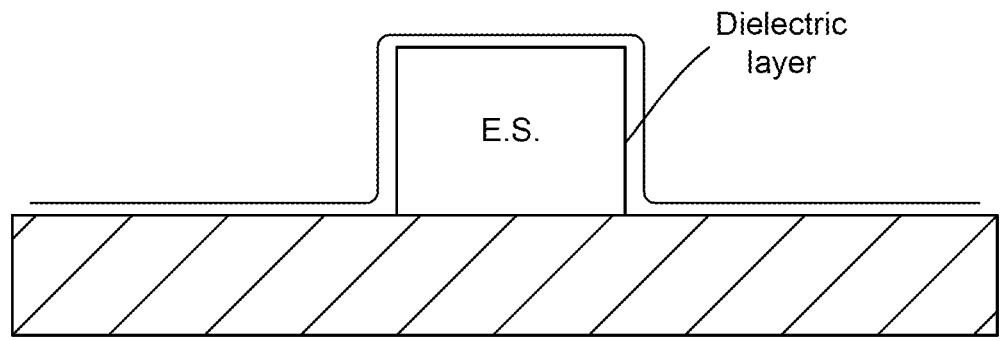
FIG. 42 is a side view of an embodiment of an enhancement structure of the present invention in which a thin layer of a dielectric film is applied, for example by CVD or ALD, in order to dictate a distance of closest approach to a designed hot spot region of the structure to thereby prevent unintended quenching of a fluorophore and to enhance the reproducibility of a signal produced.

It is known in the art that if a fluorophore gets too close to the surface of an enhancement structure under excitation the fluorescent signal from the fluorophore can be quenched. In order to prevent this quenching, and also to enhance the reproducibility of signal produced, a thin layer of a dielectric can be applied, for example by CVD or ALD, in order to dictate the distance of closest approach to a designed hot spot region. FIG. 42 is a side view of an embodiment of an enhancement structure of the present invention in which a thin layer of a dielectric film is applied, for example by CVD or ALD, in order to dictate a distance of closest approach to a designed hot spot region of the structure to thereby prevent unintended quenching of a fluorophore and to enhance the reproducibility of a signal produced.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. An enhancement structure for use in surface-enhanced Raman scattering (SERS) and surface-enhanced fluorescence-based analysis, the structure comprising: a substrate comprising a top surface; an array of nanoscale metal-insulator-metal (MIM) structures arranged on the top surface of the substrate; an array of dielectric adhesion layers deposited between the top surface of the substrate and the array of nanoscale MIM structures; and one or more additional dielectric layers, having a tilted orientation, deposited around at least a periphery of one or more MIM structures.

2. The enhancement structure of claim 1, wherein the array of nanoscale metallic structures comprises at least one of gold (Au), silver (Ag), aluminum (Al), and one or more alloys thereof.

3. The enhancement structure of claim 1, wherein the array of dielectric layers comprises at least one of silicon dioxide ($SiO_2$), magnesium oxide (MgO), silicon nitride ($Si_3N_4$), and aluminum oxide ($Al_2O_3$).

4. The enhancement structure of claim 1, wherein each of the array of dielectric layers has a thickness of less than 10 nm.

5. The enhancement structure of claim 1, wherein each nanoscale MIM structure comprises a bottom surface adhered to the top surface of the substrate via a respective dielectric layer.

6. The enhancement structure of claim 5, wherein at least some dielectric layers have a surface area that is greater than a surface area of a bottom surface of a respective nanoscale MIM structure such that a portion of a dielectric layer extends beyond a perimeter of a bottom surface of a respective nanoscale MIM structure.

7. The enhancement structure of claim 1, wherein a refractive index of the substrate at Raman pump and Raman Stokes wavelengths is at least 1.5.

8. The enhancement structure of claim 1, wherein the substrate comprises glass.

9. The enhancement structure of claim 1, wherein the substrate comprises silicon dioxide ($SiO_2$).

10. The enhancement structure of claim 1, wherein the substrate comprises an amorphous sapphire material.

11. The enhancement structure of claim 1, further comprising a dielectric film layer deposited on the top surface of the substrate, wherein the dielectric film layer comprises a refractive index at Raman pump and Raman Stokes wavelengths greater than 1.5.

12. The enhancement structure of claim 11, wherein the dielectric film layer comprises silicon nitride ($Si_3N_4$) or silicon oxynitride ($Si_xN_yO$).

13. The enhancement structure of claim 11, wherein the dielectric film layer is deposited between the top surface of the substrate and the array of nanoscale MIM structures.

14. The enhancement structure of claim 1, wherein at least some of the array of nanoscale MIM structures have a circular shape.

15. The enhancement structure of claim 1, wherein at least some of the array of nanoscale MIM structures have an elliptical shape with a ratio other than 1:1.

16. The enhancement structure of claim 1, wherein the array of nanoscale MIM structures comprises an array of individual discs.

17. The enhancement structure of claim 1, wherein the array of nanoscale MIM structures comprises an array of pairs of discs.

18. The enhancement structure of claim 17, wherein each pair of discs comprises an outer annular disc and an inner annular disc coaxially aligned with one another.

19. The enhancement structure of claim 1, wherein an electric dipole resonance of the array of nanoscale MIM structures is tuned to match a Raman pump wavelength.

20. The enhancement structure of claim 1, wherein a magnetic dipole resonance of the array of nanoscale MIM structures is tuned to match a Raman Stokes wavelength.

21. The enhancement structure of claim 1, wherein the insulating layer of the MIM structure comprises at least one of silicon dioxide ($SiO_2$), silicon nitride ($Si_3N_4$), and aluminum oxide ($Al_2O_3$).

22. The enhancement structure of claim 1, wherein the metal of the MIM structure comprises at least one of one of gold (Au), silver (Ag), aluminum (Al), and one or more alloys thereof.

23. The enhancement structure of claim 1, wherein at least some dielectric adhesion layers have a surface area that is greater than a surface area of a bottom surface of a respective one of the MIM structures such that a portion of a dielectric adhesion layer extends beyond a perimeter of a bottom surface of a respective MIM structure and is exposed on the top surface of the substrate.

24. The enhancement structure of claim 1, wherein the additional dielectric layer has a varying thickness.

25. The enhancement structure of claim 24, wherein the additional dielectric layer has a first thickness that is greater than a thickness of an underlying dielectric adhesion layer and a second thickness that is less than a thickness of the underlying dielectric adhesion layer.

26. The enhancement structure of claim 1, wherein the additional dielectric layer has a thickness of less than 10 nm.

27. The enhancement structure of claim 25, wherein the additional dielectric layer has a profile that tapers from the first thickness to the second thickness.

28. The enhancement structure of claim 27, wherein the additional dielectric layer is deposited at an angle relative to the top surface of the substrate.

29. The enhancement structure of claim 1, wherein the dielectric adhesion layers comprise at least one of silicon dioxide ($SiO_2$), silicon nitride ($Si_3N_4$), and aluminum oxide ($Al_2O_3$).

30. The enhancement structure of claim 1, wherein the one or more additional dielectric layers comprise at least one of silicon dioxide ($SiO_2$), silicon nitride ($Si_3N_4$), and aluminum oxide ($Al_2O_3$).

31. The enhancement structure of claim 1, wherein the dielectric adhesion layers each comprise a metal oxide.

32. The enhancement structure of claim 31, wherein the metal oxide inhibits loss at Raman pump and Raman Stokes wavelengths.

* * * * *